US009903872B2

United States Patent
(12)
Rohlff

(10) Patent No.: US 9,903,872 B2
(45) Date of Patent: Feb. 27, 2018

(54) IDENTIFICATION OF PROTEIN ASSOCIATED WITH HEPATOCELLULAR CARCINOMA, GLIOBASTOMA AND LUNG CANCER

(71) Applicant: Christian Rohlff, Abingdon (GB)

(72) Inventor: Christian Rohlff, Abingdon (GB)

(73) Assignee: Oxford BioTherapeutics, Ltd., Abingdon (GB)

( * ) Notice: Subject to any disclaimer, the term of this patent is extended or adjusted under 35 U.S.C. 154(b) by 0 days.

(21) Appl. No.: 14/850,358

(22) Filed: Sep. 10, 2015

(65) Prior Publication Data

US 2016/0084840 A1 Mar. 24, 2016

Related U.S. Application Data

(63) Continuation of application No. 12/395,579, filed on Feb. 27, 2009, now abandoned, which is a continuation of application No. PCT/GB2007/050515, filed on Aug. 29, 2007.

(60) Provisional application No. 60/842,429, filed on Sep. 6, 2006.

(30) Foreign Application Priority Data

Aug. 29, 2006 (GB) .................................. 0616967.6

(51) Int. Cl.

*A61K 39/00* (2006.01)
*G01N 33/574* (2006.01)
*C07K 16/28* (2006.01)
*A61K 39/395* (2006.01)

(52) U.S. Cl.

CPC ... *G01N 33/57492* (2013.01); *C07K 16/2803* (2013.01); *G01N 33/57407* (2013.01); *G01N 33/57423* (2013.01); *G01N 33/57438* (2013.01); *A61K 39/39558* (2013.01); *A61K 2039/505* (2013.01); *G01N 2333/70503* (2013.01)

(58) Field of Classification Search

CPC .................... A61K 2039/505; A61K 39/39558

See application file for complete search history.

(56) References Cited

U.S. PATENT DOCUMENTS

| | | | |
|---|---|---|---|
| 6,512,095 B2 | 1/2003 | Baum | |
| 6,596,493 B1 | 7/2003 | Reeves et al. | |
| 7,129,338 B1 | 10/2006 | Ota et al. | |
| 7,153,657 B2 | 12/2006 | Reeves et al. | |
| 7,189,566 B2 | 3/2007 | Botstein et al. | |
| 7,267,960 B2 | 9/2007 | Galibert et al. | |
| 7,368,531 B2 | 5/2008 | Rosen et al. | |
| 7,402,655 B2 | 7/2008 | Baum et al. | |
| 7,411,051 B2 | 8/2008 | Rosen et al. | |
| 7,446,176 B2 | 11/2008 | Ni et al. | |
| 7,608,413 B1 * | 10/2009 | Joseloff | G01N 33/57438 424/130.1 |
| 7,659,385 B2 | 2/2010 | Baum et al. | |
| 7,741,115 B2 | 6/2010 | Baum et al. | |
| 7,807,392 B1 | 10/2010 | Domon et al. | |
| 7,833,712 B2 | 11/2010 | Reeves et al. | |
| 7,842,291 B1 | 11/2010 | Ruben et al. | |
| 7,842,467 B1 * | 11/2010 | Heidbrink | G01N 33/57415 435/7.1 |
| 7,888,497 B2 | 2/2011 | Bentwich et al. | 536/24.5 |
| 8,048,992 B2 | 11/2011 | Kurosawa et al. | 530/387.1 |
| 2006/0240441 A1 | 10/2006 | Taylor et al. | 435/6 |
| 2009/0023142 A1 | 1/2009 | Cheung | 435/6 |
| 2009/0053243 A1 | 2/2009 | Kurosawa et al. | 424/174.1 |
| 2009/0203538 A1 | 8/2009 | Sugioka et al. | 506/9 |
| 2009/0317392 A1 | 12/2009 | Nakamura et al. | 424/139.1 |
| 2010/0227771 A1 | 9/2010 | Najari et al. | 506/9 |
| 2011/0183866 A1 * | 7/2011 | Clarke | C12N 5/0693 506/9 |
| 2012/0046451 A1 | 2/2012 | Kurosawa et al. | 530/387.3 |
| 2012/0093826 A1 * | 4/2012 | Terrett | A61K 33/24 424/143.1 |

FOREIGN PATENT DOCUMENTS

| | | | |
|---|---|---|---|
| EP | 1498424 | A | 1/2005 |
| EP | 1860119 | A | 11/2007 |
| EP | 1918299 | A | 5/2008 |
| EP | 2133362 | A | 12/2009 |
| EP | 2196474 | A | 6/2010 |
| EP | 1464709 | A | 3/2012 |
| JP | 2005147798 | A | 6/2005 |
| JP | 2006317220 | A | 11/2006 |
| JP | 2007186492 | A | 7/2007 |
| WO | 1999/028462 | A | 6/1999 |
| WO | 1999/057132 | A | 11/1999 |
| WO | 2000/008158 | A | 2/2000 |
| WO | 2000/028032 | A | 5/2000 |
| WO | 2000/029435 | A | 5/2000 |
| WO | 2000/032776 | A | 6/2000 |

(Continued)

OTHER PUBLICATIONS

Kitamura et al. (Biochem. Biophys. Res. Commun. Jun. 12, 2009; 383 (4):480-4).*
Watabe et al. (Histol. Histopathol. Oct. 2003; 18 (4): 1321-9).*
Bergers et al. (Current Opinion in Genetics and Development. 2000; 10: 120-127).*
Kelland (Eur. J. Cancer. Apr. 2004; 40 (6): 827-836).*
Saijo et al. (Cancer Sci. Oct. 2004; 95 (10): 772-776).*
Dennis (Nature. Aug. 7, 2006; 442: 739-741).*
Gura (Science. 1997; 278: 1041-1042).*
Stancoviski et al. (Proceedings of the National Academy of Science USA. 1991; 88: 8691-8695).*

(Continued)

*Primary Examiner* — Stephen Rawlings
(74) *Attorney, Agent, or Firm* — Klauber & Jackson LLC

(57) ABSTRACT

The present invention provides methods and compositions for screening, diagnosis and prognosis of HCC, glioblastoma and lung cancer, for monitoring the effectiveness of HCC, glioblastoma and lung cancer treatment, and for drug development.

4 Claims, 18 Drawing Sheets

(56) References Cited

FOREIGN PATENT DOCUMENTS

| | | | | |
|---|---|---|---|---|
| WO | 2000/056889 | A | | 9/2000 |
| WO | 2001/068848 | A | | 9/2001 |
| WO | 2002/014557 | A | | 2/2002 |
| WO | 2002/018424 | A | | 3/2002 |
| WO | 2002/066643 | A | | 8/2002 |
| WO | 2004/074320 | A | | 9/2004 |
| WO | 2005/012530 | A | | 2/2005 |
| WO | 2005/032495 | A | | 4/2005 |
| WO | 2006/049854 | A | | 5/2006 |
| WO | 2006/090750 | A | | 8/2006 |
| WO | WO2006089091 | A2 | | 8/2006 |
| WO | WO2008026010 | A1 | * | 8/2006 |
| WO | 2007/074832 | A | | 7/2007 |
| WO | 2008/007648 | A | | 1/2008 |
| WO | 2008/021290 | A | | 2/2008 |
| WO | 2008/053049 | A | | 5/2008 |
| WO | 2008/066655 | A | | 6/2008 |
| WO | 2008/142693 | A | | 11/2008 |
| WO | 2008/143639 | A | | 11/2008 |
| WO | 2009/029883 | A | | 3/2009 |
| WO | 2009/040782 | A | | 4/2009 |
| WO | 2009/147549 | A | | 12/2009 |
| WO | 2010/088187 | A | | 8/2010 |
| WO | 2010/102175 | A | | 9/2010 |

OTHER PUBLICATIONS

Heller et al. (Oncogene. Feb. 9, 2006; 25 (6): 959-68).*

Kikuchi et al. (Cancer Sci. Jun. 2012; 103 (6): 1051-7).*

Fukami et al., "Promoter methylation of the TSLC1 gene in advanced lung tumors and various cancer cell lines", Int J Cancer, 2003, 107:53-59.

Reymond et al., "Expression and functional proteomics studies in colorectal cancer", Pathology—Research and Practice, 2004, 200:119-127.

Joseph et al., "Differences in expression of pro-caspases in small cell and non-small cell lung carcinoma", Biochemical and Biophysical Research Communications, 1999, vol. 262, pp. 381-387.

Toyooka et al., "DNA methylation profiles of lung tumors", Molecular Cancer Therapeutics, 2001, vol. 1, pp. 61-67.

Tsujiuchi T, et al., "Expression and DNA methylation patterns of Tslc1 and Dal-1 genes in hepatocellular carcinomas induced by N-nitrosodiethylamine in rats.", Cancer Sci., 2007, pp. 943-948, vol. 98, No. 7.

Tsukioka F, et al., "Expression and localization of the cell adhesion molecule SgIGSF during regeneration of the olfactory epithelium in mice.", Acta Histochem. Cytochem., 2007, pp. 43-52, vol. 40, No. 2.

Uchino K, et al., "Clinical implication and prognostic significance of the tumor suppressor TSLC1 gene detected in adenocarcinoma of the lung.", Cancer, 2003, pp. 1002-1007, vol. 98, No. 5.

Urase K, et al., "Expression of RA175 mRNA, a new member of the immunoglobulin superfamily, in developing mouse brain.", Neuroreport, 2001, pp. 3217-3221, vol. 12, No. 15.

Usami Y, et al., "Tumor suppressor in lung cancer-1 as a novel ameloblast adhesion molecule and its downregulation in ameloblastoma.", Pathol. Int., 2007, pp. 68-75, vol. 57, No. 2.

Van Der Weyden L, et al., "Loss of TSLC1 causes male infertility due to a defect at the spermatid stage of spermatogenesis.", Mol. Cell Biol., 2006, pp. 3595-3609, vol. 26, No. 9.

Wakayama T, et al., "Cloning and characterization of a novel mouse immunoglobulin superfamily gene expressed in early spermatogenic cells.", Mol. Reprod. Dev., 2001, pp. 158-164, vol. 60, No. 2.

Wakayama T, et al., "Expression and functional characterization of the adhesion molecule spermatogenic immunoglobulin superfamily in the mouse testis.", Biology of Reproduction, 2003, pp. 1755-1763, vol. 68, No. 5.

Wakayama T, et al., "Heterophilic binding of the adhesion molecules poliovirus receptor and immunoglobulin superfamily 4A in the interaction between mouse spermatogenic and Sertoli cells.", Biol. Reprod., 2007, pp. 1081-1090, vol. 76, No. 6.

Wakayama T, et al., "Role of the spermatogenic-Sertoli cell interaction through cell adhesion molecule-1 (CADM1) in spermatogenesis.", Anat. Sci. Int., 2009, pp. 112-121, vol. 84, No. 3.

Wang CY, et al., "Preparation and characterization of monoclonal antibodies recognizing three distinct differentiation antigens (BL1, BL2, BL3) on human B lymphocytes.", J. Immunol., 1984, pp. 684-691, vol. 133, No. 2.

Watabe K, et al, "Distinct roles for the SgIGSF adhesion molecule and c-kit receptor tyrosine kinase in the interaction between mast cells and the mesentery.", Biochem. Biophys. Res. Commun., 2004, pp. 782-788, vol. 324, No. 2.

Watabe K, et al., "IGSF4: a new intercellular adhesion molecule that is called by three names, TSLC1, SgIGSF and SynCAM, by virtue of its diverse function.", Histol. Histopathol., 2003, pp. 1321-1329, vol. 18.

Williams YN, et al., "Cell adhesion and prostate tumor-suppressor activity of TSLL2/IGSF4C, an immunoglobulin superfamily molecule homologous to TSLC1/IGSF4.", Oncogene, 2006, pp. 1446-1453, vol. 25, No. 10.

Wilting SM, et al, "Chromosomal signatures of a subset of high-grade premalignant cervical lesions closely resemble invasive carcinomas.", Cancer Res., 2009, pp. 647-655, vol. 69.

Worsham MJ, et al., "Epigenetic events of disease progression in head and neck squamous cell carcinoma.", Arch. Otolaryngol, Head Neck Surg., 2006, pp. 668-677, vol. 132, No. 6.

Yageta M, et al., "Direct association of TSLC1 and DAL-1, two distinct tumor suppressor proteins in lung cancer.", Cancer Res., 2002, pp. 5129-5133, vol. 62.

Yamada D, et al., "Disruption of spermatogenic cell adhesion and male infertility in mice lacking TSLC1/IGSF4, an immunoglobulin superfamily cell adhesion molecule.", Mol. Cell Biol., 2006, pp. 3610-3624, vol. 26, No. 9.

Yamagata M, et al "Synaptic adhesion molecules.", Curr. Opin. Cell Biol., 2003, pp. 621-632, vol. 15, No. 5.

Yang W, et al., "Human lung mast cells adhere to human airway smooth muscle, in part, via tumor suppressor in lung cancer-1.", J. Immunol., 2006, pp. 1238-1243, vol. 176, No. 2.

Yang YX., et al., "Involvement of tumor suppressor in lung cancer 1 gene expression in cervical carcinogenesis.", Int. J. Gynecol. Cancer, 2006, pp. 1868-1872, vol. 16, No. 5.

Zelano J, et al., "Altered expression of nectin-like adhesion molecules in the peripheral nerve after sciatic nerve transection.", Neurosci., Lett., 2009, pp. 28-33, vol. 449, No. 1.

Zalano J, et al., "Down-regulation of mRNAs for synaptic adhesion molecules neuroligin-2 and -3 and synCam1 in spinal motoneurons after axotomy.", J. Comp. Neurol., 2007, pp. 308-318, vol. 503, No. 2.

Zelano J, et al., "SynCAM1 expression correlates with restoration of central synapses on spinal motoneurons after two different models of peripheral nerve injury.", J. Comp. Neurol., 2009, pp. 670-682, vol. 517, No. 5.

Zhang J, et al., "DNA methylation in anal intraepithelial lesions and anal squamous cell carcinoma.", Clin. Cancer Res., 2005, pp. 6544-6549, vol. 11.

Zhiling T, et al., "Mutations in the gene encoding CADM1 are associated with autism spectrum disorder.", Biochem. Biophys. Res. Commun., 2008, pp. 926-929, vol. 377, No. 3.

Zhou L, et al., "Frquent hypermethylation of RASSF1A and TSLC1, and high viral load of Epstein-Barr Virus DNA in nasopharyngeal carcinoma and matched turmor-adjacent tissues.", Neoplasia, 2005, pp. 809-815, vol. 7, No. 9.

Zhou Y, et al., "Nectin-like molecule 1 is a protein 4.1N associated protein and recruits proteins 4.1N from cytoplasm to the plasma membrane.", Biochem. Biophys. Acta., 2005, pp. 142-154, vol. 1669, No. 2.

Garrow K, et al., "Cell adhesion molecules at the synapse.", Frontiers in Bioscience, 2006, pp. 2400-2419, vol. 11.

Kitamura et al., "Frequent overexpression of CADM1/IGSF4 in lung adenocarcinoma", Biochem. Biophys. Res. Comm, 2009, pp. 480-484 vol. 383, No. 4.

(56) References Cited

OTHER PUBLICATIONS

Kikuchi S, et al, "Hypermethylation of the TSLC1/IGSF4 promoter is associated with tobacco smoking and a poor prognosis in primary nonsmall cell lung carcinoma.", Cancer, 2006, pp. 1751-1758, vol. 106, No. 8.
Kikuchi S, et al., "Promoter methylation of DAL-1/4.1B predicts poor prognosis in non-small cell lung cancer.", Clin. Cancer Res., 2005, pp. 2954-2961, vol. 11, No. 8.
Kitamura Y, "MITF and SgIGSF: an essential transcription factor and its target adhesion molecule for development and survival of mast cells.", Novartis Found Symp., 2005, pp. 4-11, discussion 11-4, 95-9, vol. 271.
Knowles DM, et al., "A new human B-lymphocyte surface antigen (Bl 2) detectable by a hybridoma monoclonal antibody: distribution on benign and malignant lymphoid cells.", Blood, 1983, pp. 191-199, vol. 62.
Kuramochi M, et al., "TSLC1 is a tumor-suppressor gene in human non-small-cell lung cancer.", Nat. Genet, 2001, pp. 427-430, vol. 27, No. 4.
Li J, et al., "IGSF4 promoter methylation and expression silencing in human cervical cancer.", Gynecol. Oncol., 2005, pp. 150-158, vol. 96, No. 1.
Li M, et al., "The study on methylation of gene IGSF4 promoter in acute leukemia cells.", Zhongguo Shi Yan Xue Ye Xue Za Zhi, 2004, pp. 125-127, vol. 12, No. 2, Abstract only.
Lindsey JC, et al., "Identification of tumour-specific epigenetic events in medulloblastoma development by hypermethylation profiling." Carcinogenesis, 2004, pp. 661-668, vol. 25, No. 5.
Lung HL, et al., "Fine mapping of the 11q22-23 tumor suppressive region and involvement of TSLC1 in nasopharyngeal carcinoma.", Int. J. Cancer, 2005, pp. 628-635, vol. 112, No. 4.
Lung HL, et al., "TSLC1 is a tumor suppressor gene associated with metastasis in nasopharyngeal carcinoma.", Cancer Res., 2006, p. 9385-9392, vol. 66.
Lusis E, et al., "Meningioma: an update.", Curr. Opin. Neural., 2004, pp. 687-692, vol. 17, No. 6.
Mao X, et al., "Re-expression of TSLC1 in a non-small-cell lung cancer cell line induces apoptosis and inhibits tumor growth.", Oncogene, 2004, pp. 5632-5642, vol. 23.
Mao X, et al., "The cytoplasmic domain is critical to the tumor suppressor activity of TSLC1 in non-small cell lung cancer.", Cancer Res., 2003, pp. 7979-7985, vol. 63.
Masuda M, et al., "CADM1 interacts with Tiam1 and promotes invasive phenotype of human T-cell leukemia virus type I (HTLV-I) transformed cells and adult T-cell leukemia (ATL) cells.", J. Biol. Chem., 2010, pp. 15511-15522, vol. 285, No. 20.
Masuda M, et al., "The tumor suppressor protein TSLC1 is involved in cell-cell adhesion.", J. Biol. Chem., 2002, pp. 31014-31019, vol. 277, No. 34.
Masuda M, et al., "Tumor suppressor in lung cancer (TSLC)1 suppresses epithelial cell scattering and tubulogenesis.", J. Biol. Chem., 2005, pp. 42164-42171, vol. 280, No. 51.
Maurel P, et al., "Nectin-like proteins mediate axon Schwann cell interactions along the internode and are essential for myelination.", J. Cell Biol., 2007, pp. 861-874, vol. 178, No. 5.
Missler M, "Synaptic cell adhesion goes functional.", Trends Neurosci., 2003, pp. 176-178, vol. 26, No. 4.
Momoi T, et al., "Genetic factors and epigenetic factors for autism: endoplasmic reticulum stress and impaired synaptic function.", Cell Biol. Int., 2009, pp. 13-19, vol. 34, No. 1.
Mori E, et al., "Number of mast cells in the peritoneal cavity of mice: influence of microphthalmia transcription factor through transcription of newly found mast cell adhesion molecule, spermatogenic immunoglobulin superfamily.", Am. J. Pathol., 2004, vol. 165, No. 2.
Murakami Y, "Functional cloning of a tumor suppressor gene, TSLC1, in human non-small cell lung cancer.", Oncogene, 2002, pp. 6936-6948, vol. 21, No. 45.
Murakami Y, "Involvement of a cell adhesion molecule, TSLC1/IGSF4, in human oncogenesis.", Cancer Sci., 2005, pp. 543-552, vol. 96, issue 9.
Murakami Y, et al, "Involvement of a Tumor Suppressor Protein CADM1/TSLC1 in Human Non-small Cell Lung Cancer.", Haigan, 2009, pp. 910-916, vol. 49, No. 6., Abstract only.
Murakami Y, et al., "Involvement of a Tumor Suppressor TSLC1/CADM1 in Lung Tumorigenesis in Human and the Gene-deficient Mice: C6-03.", J. Thoracic Oncology, 2007, p. S376, vol. 2, Issue 8.
Nam Ci, et al., "Postsynaptic assembly induced by neurexin-neuroligin interaction and neurotransmitter.", Proc. Natl., Acad. Sci. USA, 2005, pp. 6137-6142, vol. 102, No. 17.
Ochiai H, et al, "Bmi1 is a MYCN target gene that regulates tumorigenesis through repression of KIF1Bbeta and TSLC1 in neuroblastoma.", Oncogene, 2010, pp. 2681-2690, vol. 29, No. 18.
Ohta Y, et al., "Spatiotemporal patterns of expression of IGSF4 in developing mouse nervous system.", Brain Res. Dev, Brain Res., 2005, pp. 23-31, vol. 156, No. 1.
Patino-Lopez G, et al., "Human class-I restricted T cell associated molecule is highly expressed in the cerebellum and is a marker for activated NKT and CD8+ T lymphocytes.", J. Neuroimmunol., 2006, pp. 145-155, vol. 171, Nos. 1-2.
Paulsson K, et al., "Methylation of tumour suppressor gene promoters in the presence and absence of transcriptional silencing in high hyperdiploid acute lymphoblastic leukaemia.", British J. Haematology, 2009, pp. 838-847, vol. 144, issue 6.
Pletcher MT, et al., "Identification of tumor suppressor candidate genes by physical and sequence mapping of the TSLC1 region of human chromosome 11q23.", Gene, 2001, pp. 181-189, vol. 273.
Qin L, et al., "The growth inhibition effects of TSLC1 gene on human hepatocyte carcinoma cell line HepG2.", Zhonghua Gan Zang Bing Za Zhi, 2007, pp. 509-512, vol. 15, No. 7, Abstract only.
Rohrs S, et al., "Hypomethylation and expression of BEX2, IGSF4 and TIMP3 indicative of MLL translocations in Acute Myeloid Leukemia.", Mol. Cancer, 2009, p. 86, vol. 8.
Sara Y, et al., "Selective capability of SynCAM and neuroligin for functional synapse assembly.", J. Neurosci., 2005, pp. 260-270, vol. 25, No. 1.
Sasaki H, et al., "Overexpression of a cell adhesion molecule, TSLC1, as a possible molecular marker for acute-type adult T-cell leukemia.", Blood, 2005, pp. 1204-1213, vol. 105.
Shimizu K, et al., "Aberrant DNA methylation of the 5' upstream region of Tslc1 gene in hamster pancreatic tumors.", Biochem. Biophys. Res. Commun., 2007, pp. 522-526, vol. 353, No. 2.
Shimizu K, et al., "Reduced expression of the Tslc1 gene and its aberrant DNA methylation in rat lung tumors.", Biochem. Biophys. Biophys. Res. Commun., 2006, pp. 358-362, vol. 347, No. 1.
Shingai T, et al., "Implications of nectin-like molecule-2/IGSF4/RA175/SgIGSF/TSLC1/SynCAM1 in cell-cell adhesion and transmembrane protein localization in epithelial cells.", J. Biol. Chem., 2003, pp. 35421-35427, vol. 278, No. 37.
Soejima K, et al., "DNA methyltransferase 3b contributes to oncogenic transformation induced by SV40T antigen and activated Ras.", Oncogene, 2003, pp. 4723-4733, vol. 22.
Steenbergen RD, et al., "HPV-mediated transformation of the anogenital tract.", J. Clin. Virol., 2005, pp. S25-S33, vol. 32, suppl. 1.
Steenbergen RDM, "TSLC1 gene silencing in cervical cancer cell lines and cervical neoplasia.", J. Natl. Cancer Inst., 2004, pp. 294-305, vol. 96, No. 4.
Stephen JK, et al., "DNA hypermethylation profiles in squamous cell carcinoma of the vulva.", Int. J. Gynecol. Pathol., 2009, pp. 63-75, vol. 28, No. 1.
Surace EL, et al., "Loss of tumor suppressor in lung cancer-1 (TSLC1) expression in meningioma correlates with increased malignancy grade and reduced patient survival.", J. Neuropathol. Exp. Neurol., 2004, pp. 1015-1027, vol. 63, No. 10.
Surace EL, et al., "Tslc1 (nectin-like molecule-2) is essential for spermatozoa motility and male fertility.", J. Androl., 2006, pp. 816-825, vol. 27, No. 6.

(56) References Cited

OTHER PUBLICATIONS

Sussan TE, et al., "Tumor suppressor in lung cancer 1 (TSLC1) alters tumorigenic growth properties and gene expression.", Mol. Cancer, 2005, p. 28, vol. 4.
Tamara G, "Promoter methylation status of tumor suppressor and tumor-related genes in neoplastic and non-neoplastic gastric epithelia.", Histol. Histopathol., 2004, pp. 221-228, vol. 19, No. 1.
Tamura G, "Alterations of tumor suppressor and tumor-related genes in the development and progression of gastric cancer.", World J. Gastroenterol., 2006, pp. 192-198, vol. 12, No. 2.
Tanabe Y, et al.,"Brain proteins with PDZ domains associated with RA175/SynCAM.", Neurosci, Res., 2007, p. S239, vol. 58, suppl. 1.
Tanabe Y, et al., "Neuronal RA175/SynCAM1 isoforms are processed by tumor necrosis factor-alpha-converting enzyme (TACE)/ADAM17-like proteases.", Neurosci. Lett., 2008, pp. 16-21, vol. 444, No. 1.
Terada N, et al., "Involvement of a membrane skeletal protein, 4.1G, for Sertoli/germ cell interaction.", Reproduction, 2010, pp. 883-892, vol. 139.
Thivolet J, et al., "Cells in the epidermotropic lymphomas (mycosis fungoides and Sézary syndrome. Study using monoclonal antibodies.", Nouv. Presse Med., 1982, pp. 3033-3038, vol. 11, No. 41, Abstract only.
Alagaratnam S, et al, "TPD52, a candidate gene from genomic studies, is overexpressed in testicular germ cell tumours.", Mol. Cell Endocrinol., 2009, pp. 75-80, vol. 306, Nos. 1-2.
Allinen M, et al., "Analysis of 11q21-24 loss of heterozygosity candidate target genes in breast cancer: indications of TSLC1 promoter hypermethylation.", Genes Chromosomes & Cancer, 2002, pp. 384-389. vol. 34, issue 4.
Apostolidou S, et al., "DNA methylation analysis in liquid-based cytology for cervical cancer screening.", Int. J. Cancer, 2009, pp. 2995-3002, vol. 125, No. 12.
Arase N, et al., "Heterotypic interaction of CRTAM with Necl2 induces cell adhesion on activated NK cells and CD8 + T cells.", Int. Immunol., 2005, pp. 1227-1237, vol. 17, No. 9.
Bax Da, et al., "Molecular and phenotypic characterisation of paediatric glioma cell lines as models for preclinical drug development.", PLoS One, 2009, e5209, vol. 4, No. 4.
Berginc G, et al., "MS-MLPA Reveals Progressive Age-Dependent Promoter Methylation of Tumor Suppressor Genes and Possible Role of IGSF4 Gene in Colorectal Carcinogenesis of Microsatellite Instable Tumors.", Cancer Invest., 2010, pp. 94-102, vol. 28, No. 1.
Biederer T, "Bioinformatic characterization of the SynCAM family of immunoglobulin-like domain-containing adhesion molecules.", Genomics, 2006, pp. 139-150, vol. 87, No. 1.
Biederer T, "Progress from the postsynaptic side: signaling in synaptic differentiation.", Sci. STKE, 2005, p. pe9, vol. 274.
Biederer T, et al., "SynCAM, a synaptic adhesion molecule that drives synapse assembly.", Science, 2002, pp. 1525-1531, vol. 297, No. 5586.
Boles KS, et al., "The tumor suppressor TSLC1/NECL-2 triggers NK-cell and CD8+ T-cell responses through the cell-surface receptor CRTAM.", Blood, 2005, pp. 779-786, vol. 106.
Breillat C, et al., "Characterization of SynCAM surface trafficking using a SynCAM derived ligand with high homophilic binding affinity.", Biochem. Biophys, Res. Commun., 2007, pp. 655-659, vol. 359, No. 3.
Chowers I, et al., "Identification of novel genes preferentially expressed in the retina using a custom human retina cDNA microarray.", Invest. Ophthalmol. Vis. Sci., 2003, pp. 3732-3741, vol. 44, No. 9.
Database UniprotKB, 2007, accession No. Q9BY67, Q86WB8, Q8N2F4.
Duenas-Gonzalez A, et al., "Epigenetics of cervical cancer. An overview and therapeutic perspectives.", Mol. Cancer, 2005, p. 38, vol. 4.
Erlich M, et al., "Quantitative analysis of associations between DNA hypermethylation, hypomethylation, and DNMT RNA levels in ovarian tumors.", Oncogene, 2006, pp. 2636-2645, vol. 25, No. 18.
Fox MA, et al., "Seeking long-term relationship: axon and target communicate to organize synaptic differentiation.", J. Neurochem., 2006, pp. 1215-1231, vol. 97, No. 5.
Fu L, et al., "Frequent concomitant epigenetic silencing of the stress-responsive tumor suppressor gene CADM1, and its interacting partner DAL-1 in nasal NK/T-cell lymphoma.", Int. J. Cancer, 2009, pp. 1572-1578, vol. 124, No. 7.
Fujita E, et al., "Distribution of RA175/TSLC1/SynCAM, a member of the immunoglobulin superfamily, in the developing nervous system.", Brain Res. Dev. Brain Res., 2005, pp. 199-209, vol. 154, No. 2.
Fujita E, et al., "Oligo-astheno-teratozoospermia in mice lacking RA175/TSLC1/SynCAM/IGSF4A, a cell adhesion molecule in the immunoglobulin superfamily.", Mol. Cell Biol., 2006, pp. 718-726, vol. 26, No. 2.
Fujita E, et al., "RA175, which is the mouse ortholog of TSLC1, a tumor suppressor gene in human lung cancer, is a cell adhesion molecule.", Exp. Cell Res., 2003, pp. 57-66, vol. 287, No. 1.
Fukami T, et al., "Identification of the Tslc1 gene, a mouse orthologue of the human tumor suppressor TSLC1 gene.", Gene, 2002, pp. 7-12, vol. 295, No. 1.
Fukami T, et al., "Promoter methylation of the TSLC1 gene in advanced lung tumors and various cancer cell lines.", Int. J. Cancer, 2003, pp. 53-59, vol. 107.
Fukuhara H, et al., "Association of a lung tumor suppressor TSLC1 with MPP3, a human homologue of *Drosophila* tumor suppressor Dig.", Oncogene, 2003, pp. 6160-6165, vol. 22.
Fukuhara H, et al, "Promoter methylation of TSLC1 and tumor suppression by its gene product in human prostate cancer.", Jpn. J. Cancer Res., 2002, pp. 605-609, vol. 93.
Furuno T, et al., "The spermatogenic Ig superfamily/synaptic cell adhesion molecule mast-cell adhesion molecule promotes interaction with nerves.", J. Immunol., 2005, pp. 6934-6942, vol. 174, No. 11.
Galibert L, et al., "Nectin-like protein 2 defines a subset of T-cell zone dendritic cells and is a ligand for class-I-restricted T-cell-associated molecule.", J. Biol. Chem., 2005, pp. 21955-21964, vol. 280, No. 23.
Giangreco A, et al., "Necl2 regulates epidermal adhesion and wound repair.", Development, 2009, pp. 3505-3514, vol. 136.
Gomyo H, et al., "A 2-Mb sequence-ready contig map and a novel immunoglobulin superfamily gene IGSF4 in the LOH region of chromosome 11q23.2.", Genomics, 1999, pp. 139-146, vol. 62, No. 2.
Goto A, et al., "Loss of TSLC1 expression in lung adenocarcinoma: relationships with histological subtypes, sex and prognostic significance.", Cancer Sci., 2005, pp. 480-486, vol. 96, No. 8.
Gustafson KS, et al., "DNA methylation profiling of cervical squamous intraepithelial lesions using liquid-based cytology specimens: an approach that utilizes receiver-operating characteristic analysis.", Cancer, 2004, pp. 259-268, vol. 102, No. 4.
Hagiyama M, "Expression of a soluble isoform of cell adhesion molecule 1 in the brain and its involvement in directional neurite outgrowth.", Am. J. Pathol., 2009, pp. 2278-2289, vol. 174, No. 6.
Hasstedt SJ, et al., "Cell adhesion molecule 1: a novel risk factor for venous thrombosis.", Blood, 2009, pp. 3084-3019, vol. 114, No. 14.
Heller G, et al., "Expression and methylation pattern of TSLC1 cascade genes in lung carcinomas.", Oncogene, 2006, pp. 959-968, vol. 25.
Honda T, et al., "Hypermethylation of the TSLC1 gene promoter in primary gastric cancers and gastric cancer cell lines.", Jpn. J. Cancer Res., 2002, pp. 857-860, vol. 93.
Hori RT, "The minimal Tumor Suppressor in Lung Cancer-1 promoter is restrained by an inhibitory region.", Mol. Biol. Rep., 2010, pp. 1979-1985, vol. 37, No. 4.
Houshmandi SS, et al., "Tumor suppressor in lung cancer-1 (TSLC1) functions as a glioma tumor suppressor.", Neurology, 2006, pp. 1863-1866, vol. 67.

(56) References Cited

OTHER PUBLICATIONS

Hoy JL, et al., "SynCAM1 recruits NMDA receptors via protein 4.1B.", Mol. Cell Neurosci., 2009, pp. 466-483, vol. 42, No. 4.
Hui Ab, et al., "Epigenetic inactivation of TSLC1 gene in nasopharyngeal carcinoma.", Molecular Carcinogenesis, 2003, pp. 170-178, vol. 38, issue 4.
Ito A, et al., "Contribution of the SgIGSF adhesion molecule to survival of cultured mast cells in vivo.", Biochem. Biophys. Res. Commun., 2004, pp. 200-206, vol. 319, No. 1.
Ito A, et al., "Direct interaction between nerves and mast cells mediated by the SgIGSF/SynCAM adhesion molecule.", J. Pharmacol. Sci., 2006, pp. 1-5, vol. 102, No. 1.
Ito A, et al., "Expression of cell adhesion molecule 1 in malignant pleural mesothelioma as a cause of efficient adhesion and growth on mesothelium.", Laboratory Investigation, 2008, pp. 504-514, vol. 88.
Ito A, et al., "Involvement of the SgIGSF/Necl-2 adhesion molecule in degranulation of mesenteric mast cells.", J. Neuroimmunol., 2007, pp. 209-213, vol. 184, Nos. 1-2.
Ito A, et al., "SgIGSF is a novel biliary-epithelial cell adhesion molecule mediating duct/ductule development.", Hepatology, 2007, pp. 684-694, vol. 45, No. 3.
Ito A, et al., "SgIGSF: a new mast-cell adhesion molecule used for attachment to fibroblasts and transcriptionally regulated by MITF.", Blood, 2003, pp. 2601-2608, vol. 101.
Ito T, et al., "Involvement of TSLC1 in progression of esophageal squamous cell carcinoma.", Cancer Res., 2003, pp. 6320-6326, vol. 63.
Jansen M, et al, "Aberrant methylation of the 5' CpG island of TSLC1 is common in pancreatic ductal adenocarcinoma and is first manifest in high-grade PanlNs.", Cancer Biol. Ther., 2002, pp. 293-296, vol. 1, No. 3.
Kakunaga S, et al., "Nectin-like molecule-1/TSLL1/SynCAM3: a neural tissue-specific immunoglobulin-like cell-cell adhesion molecule localizing at non-junctional contact sites of presynaptic nerve terminals, axons and glia cell processes.", J. Cell Sci., 2005, pp. 1267-1277, vol. 118.
Kanduri M, et al, "Differential genome-wide array-based methylation profiles in prognostic subsets of chronic lymphocytic leukemia.", Blood, 2010, pp. 296-305, vol. 115, No. 2.
Kawano S, et al., "Silencing of ErbB3/ErbB2 Signaling by Immunoglobulin-like Necl-2.", J. Biol. Chem., 2009, pp. 23793-23805, vol. 284, No. 35.
Kijanka G, et al., "Human IgG antibody profiles differentiate between symptomatic patients with and without colorectal cancer.", Gut, 2009, pp. 69-78, vol. 59.

* cited by examiner

Figure 1A

Peptide source: 1D-GE, Hepatocellular carcinoma

```
OGTA025a (SEQ ID No: 1)   MASVVLPSGSQCAAAAAAAAPPGLRLRLLLLLFSAAALIPTGDGQNLFTK 50
OGTA025b (SEQ ID No: 2)   MASVVLPSGSQCAAAAAAAAPPGLRLRLLLLLFSAAALIPTGDGQNLFTK 50
                          **************************************************

OGTA025a (SEQ ID No: 1)   DVTVIEGEVATISCQVNKSDDSVIQLLNPNRQTIYFRDFRPLKDSRFQLL 100
OGTA025b (SEQ ID No: 2)   DVTVIEGEVATISCQVNKSDDSVIQLLNPNRQTIYFRDFRPLKDSRFQLL 100
                          **************************************************

OGTA025a (SEQ ID No: 1)   NFSSSELKVSLTNVSISDEGRYFCQLYTDPPQESYTTITVLVPPRNLMID 150
OGTA025b (SEQ ID No: 2)   NFSSSELKVSLTNVSISDEGRYFCQLYTDPPQESYTTITVLVPPRNLMID 150
                          **************************************************

OGTA025a (SEQ ID No: 1)   IQKDTAVEGEEIEVNCTAMASKPATTIRWFKGNTELKGKSEVEEWSDMYT 200
OGTA025b (SEQ ID No: 2)   IQRDTAVEGEEIEVNCTAMASKPATTIRWFKGNTELKGKSEVEEWSDMYT 200
                          **************************************************

OGTA025a (SEQ ID No: 1)   VTSQLMLKVHKEDDGVPVICQVEHPAVTGNLQTQRYLEVQYKPQVHIQMT 250
OGTA025b (SEQ ID No: 2)   VTSQLMLKVHKEDDGVPVICQVEHPAVTGNLQTQRYLEVQYKPQVHIQMT 250
                          **************************************************

OGTA025a (SEQ ID No: 1)   YPLQGLTREGDALELTCEAIGKPQPVMVTWVRVDDEMPQHAVLSGPNLFI 300
OGTA025b (SEQ ID No: 2)   YPLQGLTREGDALELTCEAIGKPQPVMVTWVRVDDEMPQHAVLSGPNLFI 300
                          **************************************************

OGTA025a (SEQ ID No: 1)   NNLNKTDNGTYRCEASNIVGKAHSDYMLYVYDTTATTEPAVHGLTQLPNS 350
OGTA025b (SEQ ID No: 2)   NNLNKTDNGTYRCEASNIVGKAHSDYMLYVYDPPTTIPPPTTTTTTTTTT 350
                          ********************************..:*  *..   *  ..:

OGTA025a (SEQ ID No: 1)   AEELDSEDLSDSRAGEEGSIRAVDHAVIGGVVAVVVFAMLCLLIILGRYF 400
OGTA025b (SEQ ID No: 2)   TTTILT-IITDSRAGEEGSIRAVDHAVIGGVVAVVVFAMLCLLIILGRYF 399
                          :  : :   ::***************************************

OGTA025a (SEQ ID No: 1)   ARHKGTYFTHEAKGADDAADADTAIINAEGGQNNSEEKKEYFI 443
OGTA025b (SEQ ID No: 2)   ARHKGTYFTHEAKGADDAADADTAIINAEGGQNNSEEKKEYFI 442
                          *******************************************
```

Mass Match Peptides (bold):

CEASNIVGK [SEQ ID NO: 5], GTYFTHEAK [SEQ ID NO: 7], QTIYFR [SEQ ID NO: 8], SDDSVIQLLNPNR [SEQ ID NO: 9]

Tandem Peptides (underline):

SDDSVIQLLNPNR [SEQ ID NO: 9]

Figure 1B

Peptide source: 1D-GE, Glioblastoma

```
OGTA025a (SEQ ID No: 1)  MASVVLPSGSQCAAAAAAAAPPGLRLRLLLLLFSAAALIPTGDGQNLFTK 50
OGTA025b (SEQ ID No: 2)  MASVVLPSGSQCAAAAAAAAPPGLRLRLLLLLFSAAALIPTGDGQNLFTK 50
                         **************************************************

OGTA025a (SEQ ID No: 1)  DVTVIEGEVATISCQVNKSDDSVIQLLNPNRQTIYFRDFRPLKDSRFQLL 100
OGTA025b (SEQ ID No: 2)  DVTVIEGEVATISCQVNKSDDSVIQLLNPNRQTIYFRDFRPLKDSRFQLL 100
                         **************************************************

OGTA025a (SEQ ID No: 1)  NFSSSELKVSLTNVSISDEGRYFCQLYTDPPQESYTTITVLVPPRNLMID 150
OGTA025b (SEQ ID No: 2)  NFSSSELKVSLTNVSISDEGRYFCQLYTDPPQESYTTITVLVPPRNLMID 150
                         **************************************************

OGTA025a (SEQ ID No: 1)  IQKDTAVEGEEIEVNCTAMASKPATTIRWFKGNTELKGKSEVEEWSDMYT 200
OGTA025b (SEQ ID No: 2)  IQKDTAVEGEEIEVNCTAMASKPATTIRWFKGNTELKGKSEVEEWSDMYT 200
                         **************************************************

OGTA025a (SEQ ID No: 1)  VTSQLMLKVHKEDDGVPVICQVEHPAVTGNLQTQRYLEVQYKPQVHIQMT 250
OGTA025b (SEQ ID No: 2)  VTSQLMLKVHKEDDGVPVICQVEHPAVTGNLQTQRYLEVQYKPQVHIQMT 250
                         **************************************************

OGTA025a (SEQ ID No: 1)  YPLQGLTREGDALELTCEAIGKPQPVMVTWVRVDDEMPQHAVLSGPNLFI 300
OGTA025b (SEQ ID No: 2)  YPLQGLTREGDALELTCEAIGKPQPVMVTWVRVDDEMPQHAVLSGPNLFI 300
                         **************************************************

OGTA025a (SEQ ID No: 1)  NNLNKTDNGTYRCEASNIVGKAHSDYMLYVYDTTATTEPAVHGLTQLPNS 350
OGTA025b (SEQ ID No: 2)  NNLNKTDNGTYRCEASNIVGKAHSDYMLYVYDPPTTIPPPTTTTTTTTTT 350
                         ********************************..:*  *..   *  ..:

OGTA025a (SEQ ID No: 1)  AEELDSEDLSDSRAGEEGSIRAVDHAVIGGVVAVVVFAMLCLLIILGRYF 400
OGTA025b (SEQ ID No: 2)  TTTILT-IITDSRAGEEGSIRAVDHAVIGGVVAVVVFAMLCLLIILGRYF 399
                         :  :  :   ::**************************************

OGTA025a (SEQ ID No: 1)  ARHKGTYFTHEAKGADDAADADTAIINAEGGQNNSEEKKEYFI 443
OGTA025b (SEQ ID No: 2)  ARHKGTYFTHEAKGADDAADADTAIINAEGGQNNSEEKKEYFI 442
                         *******************************************
```

Mass Match Peptides (bold):

AGEEGSIR [SEQ ID NO: 4]
CEASNIVGK [SEQ ID NO: 5]
DFRPLK [SEQ ID NO: 6]
QTIYFR [SEQ ID NO: 8]
SDDSVIQLLNPNR [SEQ ID NO: 9]

Tandem Peptides (underline):

SDDSVIQLLNPNR [SEQ ID NO: 9]

Figure 1C

Peptide Source: iTRAQ, Lung Cancer

```
OGTA025a (SEQ ID No: 1)   MASVVLPSGSQCAAAAAAAAPPGLRLRLLLLLFSAAALIPTGDGQNLFTK 50
OGTA025b (SEQ ID No: 2)   MASVVLPSGSQCAAAAAAAAPPGLRLRLLLLLFSAAALIPTGDGQNLFTK 50
                          **************************************************

OGTA025a (SEQ ID No: 1)   DVTVIEGEVATISCQVNKSDDSVIQLLNPNRQTIYFRDFRPLKDSRFQLL 100
OGTA025b (SEQ ID No: 2)   DVTVIEGEVATISCQVNKSDDSVIQLLNPNRQTIYFRDFRPLKDSRFQLL
100
                          **************************************************

OGTA025a (SEQ ID No: 1)   NFSSSELKVSLTNVSISDEGRYFCQLYTDPPQESYTTITVLVPPRNLMID 150
OGTA025b (SEQ ID No: 2)   NFSSSELKVSLTNVSISDEGRYFCQLYTDPPQESYTTITVLVPPRNLMID 150
                          **************************************************

OGTA025a (SEQ ID No: 1)   IQKDTAVEGEEIEVNCTAMASKPATTIRWFKGNTELKGKSEVEEWSDMYT 200
OGTA025b (SEQ ID No: 2)   IQRDTAVEGEEIEVNCTAMASKPATTIRWFKGNTELKGKSEVEEWSDMYT 200
                          **************************************************

OGTA025a (SEQ ID No: 1)   VTSQLMLKVHKEDDGVPVICQVEHPAVTGNLQTQRYLEVQYKPQVHIQMT 250
OGTA025b (SEQ ID No: 2)   VTSQLMLKVHKEDDGVPVICQVEHPAVTGNLQTQRYLEVQYKPQVHIQMT 250
                          **************************************************

OGTA025a (SEQ ID No: 1)   YPLQGLTREGDALELTCEAIGKPQPVMVTWVRVDDEMPQHAVLSGPNLFI 300
OGTA025b (SEQ ID No: 2)   YPLQGLTREGDALELTCEAIGKPQPVMVTWVRVDDEMPQHAVLSGPNLFI 300
                          **************************************************

OGTA025a (SEQ ID No: 1)   NNLNKTDNGTYRCEASNIVGKAHSDYMLYVYDTTATTEPAVHGLTQLPNS 350
OGTA025b (SEQ ID No: 2)   NNLNKTDNGTYRCEASNIVGKAHSDYMLYVYDPPTTIPPPTTTTTTTTTT 350
                          ********************************..:*  *..   *  ..:

OGTA025a (SEQ ID No: 1)   AEELDSEDLSDSRAGEEGSIRAVDHAVIGGVVAVVVFAMLCLLIILGRYF 400
OGTA025b (SEQ ID No: 2)   TTTILT-IITDSRAGEEGSIRAVDHAVIGGVVAVVVFAMLCLLIILGRYF 399
                          :   : :   ::**************************************

OGTA025a (SEQ ID No: 1)   ARHKGTYFTHEAKGADDAADADTAIINAEGGQNNSEEKKEYFI 443
OGTA025b (SEQ ID No: 2)   ARHKGTYFTHEAKGADDAADADTAIINAEGGQNNSEEKKEYFI 442
                          *******************************************
```

Mass Match Peptides (bold):

Tandem Peptides (underline):

AGEEGSIR [SEQ ID NO: 4]

Figure 1D

Peptide Source: 1D-GE, Lung Cancer

```
OGTA025a (SEQ ID No: 1)   MASVVLPSGSQCAAAAAAAAPPGLRLRLLLLLFSAAALIPTGDGQNLFTK 50
OGTA025b (SEQ ID No: 2)   MASVVLPSGSQCAAAAAAAAPPGLRLRLLLLLFSAAALIPTGDGQNLFTK 50
                          **************************************************

OGTA025a (SEQ ID No: 1)   DVTVIEGEVATISCQVNKSDDSVIQLLNPNRQTIYFRDFRPLKDSRFQLL 100
OGTA025b (SEQ ID No: 2)   DVTVIEGEVATISCQVNKSDDSVIQLLNPNRQTIYFRDFRPLKDSRFQLL 100
                          **************************************************

OGTA025a (SEQ ID No: 1)   NFSSSELKVSLTNVSISDEGRYFCQLYTDPPQESYTTITVLVPPRNLMID 150
OGTA025b (SEQ ID No: 2)   NFSSSELKVSLTNVSISDEGRYFCQLYTDPPQESYTTITVLVPPRNLMID 150
                          **************************************************

OGTA025a (SEQ ID No: 1)   IQKDTAVEGEEIEVNCTAMASKPATTIRWFKGNTELKGKSEVEEWSDMYT 200
OGTA025b (SEQ ID No: 2)   IQKDTAVEGEEIEVNCTAMASKPATTIRWFKGNTELKGKSEVEEWSDMYT 200
                          **************************************************

OGTA025a (SEQ ID No: 1)   VTSQLMLKVHKEDDGVPVICQVEHPAVTGNLQTQRYLEVQYKPQVHIQMT 250
OGTA025b (SEQ ID No: 2)   VTSQLMLKVHKEDDGVPVICQVEHPAVTGNLQTQRYLEVQYKPQVHIQMT 250
                          **************************************************

OGTA025a (SEQ ID No: 1)   YPLQGLTREGDALELTCEAIGKPQPVMVTWVRVDDEMPQHAVLSGPNLFI 300
OGTA025b (SEQ ID No: 2)   YPLQGLTREGDALELTCEAIGKPQPVMVTWVRVDDEMPQHAVLSGPNLFI 300
                          **************************************************

OGTA025a (SEQ ID No: 1)   NNLNKTDNGTYRCEASNIVGKAHSDYMLYVYDTTATTEPAVHGLTQLPNS 350
OGTA025b (SEQ ID No: 2)   NNLNKTDNGTYRCEASNIVGKAHSDYMLYVYDPPTTIPPPTTTTTTTTTT 350
                          ********************************..:*  *..   *  ..:

OGTA025a (SEQ ID No: 1)   AEELDSEDLSDSRAGEEGSIRAVDHAVIGGVVAVVVFAMLCLLIILGRYF 400
OGTA025b (SEQ ID No: 2)   TTTILT-IITDSRAGEEGSIRAVDHAVIGGVVAVVVFAMLCLLIILGRYF 399
                          :  : :  ::****************************************

OGTA025a (SEQ ID No: 1)   ARHKGTYFTHEAKGADDAADADTAIINAPGGQNNSEEKKEYFI 443
OGTA025b (SEQ ID No: 2)   ARHKGTYFTHEAKGADDAADADTAIINAPGGQNNSEEKKEYFI 442
                          *******************************************
```

Figure 1E

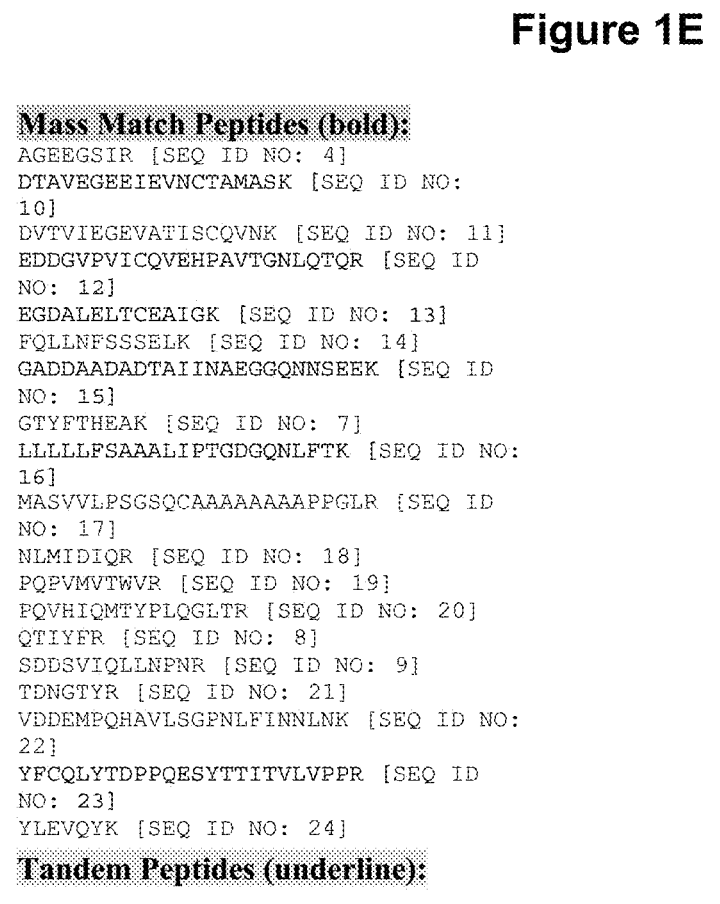

Mass Match Peptides (bold):

AGEEGSIR [SEQ ID NO: 4]
DTAVEGEEIEVNCTAMASK [SEQ ID NO: 10]
DVTVIEGEVATISCQVNK [SEQ ID NO: 11]
EDDGVPVICQVEHPAVTGNLQTQR [SEQ ID NO: 12]
EGDALELTCEAIGK [SEQ ID NO: 13]
FQLLNFSSSELK [SEQ ID NO: 14]
GADDAADADTAIINAEGGQNNSEEK [SEQ ID NO: 15]
GTYFTHEAK [SEQ ID NO: 7]
LLLLLFSAAALIPTGDGQNLFTK [SEQ ID NO: 16]
MASVVLPSGSQCAAAAAAAAPPGLR [SEQ ID NO: 17]
NLMIDIQR [SEQ ID NO: 18]
PQPVMVTWVR [SEQ ID NO: 19]
PQVHIQMTYPLQGLTR [SEQ ID NO: 20]
QTIYFR [SEQ ID NO: 8]
SDDSVIQLLNPNR [SEQ ID NO: 9]
TDNGTYR [SEQ ID NO: 21]
VDDEMPQHAVLSGPNLFINNLNK [SEQ ID NO: 22]
YFCQLYTDPPQESYTTITVLVPPR [SEQ ID NO: 23]
YLEVQYK [SEQ ID NO: 24]

Tandem Peptides (underline):

| Teratocarcinoma | | | | | |
|---|---|---|---|---|---|
| **Subcellular location** | **Signal level** | | | | |
| | Very Low | Low | Medium | High | Very High |
| Membrane | | | | | |
| Whole Cell | | | | | |

Figure 4

OGTA025 sequence used for immunization (SEQ ID No: 3):

MRAWIFFLLCLAGRALTQNLFTKDVTVIEGEVATISCQVNKSDDSVIQLLNPNRQTIYFRDFRPLKDSRFQLL
NFSSSELKVSLTNVSISDEGRYFCQLYTDPPQESYTTITVLVPPRNLMIDIQRDTAVEGEEIEVNCTAMASKP
ATTIRWFKGNTELKGKSEVEEWSDMYTVTSQLMLKVHKEDDGVPVICQVEHPAVTGNLQTQRYLEVQYKPQVH
IQMTYPLQGLTREGDALELTCEAIGKPQPVMVTWVRVDDEMPQHAVLSGPNLFINNLNKTDNGTYRCEASNIV
GKAHSDYMLYVYDSRAGEEGSIRAVDASHHHHHH*

IDENTIFICATION OF PROTEIN ASSOCIATED WITH HEPATOCELLULAR CARCINOMA, GLIOBASTOMA AND LUNG CANCER

CROSS REFERENCE TO RELATED APPLICATIONS

The present application is a Continuation of U.S. application Ser. No. 12/395,579, filed Feb. 27, 2009, now abandoned, which in turn claims priority from PCT Application No. PCT/GB2007/050515 filed Aug. 29, 2007, which in turn, claims priority from Great Britain Application No. 0616967.6 filed Aug. 29, 2006 and U.S. Provisional Application Ser. No. 60/842,429 filed Sep. 6, 2006. Applicants claim the benefits of 35 U.S.C. § 120 as to the U.S. Application and the PCT application and priority under 35 U.S.C. § 119 as to the said Great Britain and U.S. Provisional applications, and the entire disclosures of all applications are incorporated herein by reference in their entireties.

INTRODUCTION

The present invention relates to the identification of a membrane protein associated with hepatocellular carcinoma (HCC), glioblastoma and lung cancer which has utility as a marker for HCC, glioblastoma and lung cancer and HCC and lung cancer metastases and which also forms a biological target against which therapeutic antibodies (or other affinity reagents such as Affibodies, Nanobodies or Unibodies) or other pharmaceutical agents can be made.

BACKGROUND OF THE INVENTION

Hepatocellular Carcinoma (HCC)

Hepatocellular carcinoma (HCC) arises from the main cells of the liver (the hepatocytes) and accounts for around 80% of all cases of liver cancer. It is usually confined to the liver and is associated with cirrhosis in 50% to 80% of patients. Hepatocellular carcinoma is about 3 times more common in males than in females. Chronic infection with hepatitis B virus (HBV) or hepatitis C virus (HCV) is a major cause of HCC and is responsible for making liver cancer the most common cancer in many parts of the world. In the United States, hepatitis C infection is responsible for about 50% to 60% of all liver cancers and hepatitis B is responsible for another 20%. Exposure to Aflatoxins is also a cause of HCC, mostly in warmer and tropical countries.

Liver cancer accounts for about 5.8% of all cancer cases globally (about 626,000 cases) and 8.9% of deaths per year (about 598,000). It is the 3rd most common cause of cancer-related death in both men and women worldwide. HCC is predominantly found in Asia and Africa, which account for 80% of cases. In the USA, there are approximately 18,500 new cases of HCC and 16,000 deaths per year.

About 85% of people diagnosed with liver cancer are between 45 and 85 years of age. About 4% are between 35 and 44 years of age and only 2.4% are younger than 35.

Hepatocellular Carcinoma Diagnosis:

Since symptoms of liver cancer often do not appear until the disease is advanced, only a small number of liver cancers are found in the early stages and can be removed with surgery. Many signs and symptoms of liver cancer are relatively nonspecific—that is, they can be caused by other cancers or by non-cancerous diseases. Imaging tests such as ultrasound, computed tomography (CT), magnetic resonance imaging (MRI) and angiography are commonly used to diagnose HCC. Other diagnostic tools include laparoscopy, biopsy, alpha-fetoprotein (AFP) blood test, liver function tests (LFTs), a prothrombin time (PT) and tests for hepatitis B and C.

Hepatocellular Carcinoma Staging:

HCC has four stages, stage I to stage IV according to the American Joint Committee on Cancer (AJCC) TNM system. HCC can be classified as localized resectable, localized unresectable or advanced. The overall 5-year relative survival rate from liver cancer is about 9%. One reason for this low survival rate is that most patients with liver cancer also have cirrhosis of the liver, which itself can be fatal (people with liver cancer and class C cirrhosis are generally too sick for any treatment and usually die in a few months). The 5 year survival for localized resectable HCC following surgery is between 40% and 70%. For advanced HCC there is no standard treatment and the 5 year survival rate is less than 5%. Survival continues to drop after diagnosis and treatment so that by 10 years it is half of what it was at 5 years.

Hepatocellular Carcinoma Treatment:

Treatment of liver cancer depends on the size of the tumor and whether the patient has cirrhosis. At this time, surgery, either by resection or liver transplantation, offers the only chance to cure a liver cancer. People without cirrhosis can do well with surgical removal of the tumor. However, in many cases, it might not be possible to safely remove a localized liver cancer. Less than 30% of the patients having explorative surgery are able to have their cancer completely removed by surgery. Partial hepatectomy results in a 5-year survival of 30% to 40%. If there is cirrhosis, or a very large tumor, most experts recommend liver transplantation as the main treatment. The 5-year survival for liver transplantation patients is around 70% but the opportunities for liver transplantation are limited.

Other treatments include radiofrequency ablation (RFA), ethanol ablation, cryosurgery, hepatic artery embolization, chemoembolization or three-dimensional conformal radiation therapy (3DCRT). Chemotherapy can also be used but shrinks fewer than 1 in 5 tumors. This may be improved by hepatic artery infusion (HAI). Chemotherapeutic agents used include Adriamycin, VP-16, Cisplatinum, Mitomycin, 5-FU and Leucovorin.

The prognosis for any treated primary liver cancer patient with progressing, recurring, or relapsing disease is poor. Treatment of liver cancer that returns after initial therapy depends on many factors, including the site of the recurrence, the type of initial treatment, and the functioning of the liver. Patients with localized resectable disease that recurs in the same spot may be eligible for further surgery.

Glioblastoma

Glioblastoma, also known as glioblastoma multiforme, may develop from a diffuse astrocytoma or an anaplastic astrocytoma but more commonly presents de novo without evidence of a less malignant precursor. Histologically, this tumor is an anaplastic, cellular glioma composed of poorly differentiated, often pleomorphic astrocytic tumor cells with marked nuclear atypia and brisk mitotic activity. Glioblastoma primarily affects the cerebral hemispheres. CNS tumors are associated with characteristic patterns of altered oncogenes, altered tumor-suppressor genes, and chromosomal abnormalities.

Glioblastoma accounts for approximately 12% to 15% of all brain tumors (which account for 85% to 90% of all primary central nervous system (CNS) tumors). New cases for CNS tumors in USA are approximately 18,800 (6.6 per 100,000 persons) per year, with around 12,800 (4.7 per 100,000 persons) deaths. This type of cancer accounts for approximately 1.3% of all cancers and 2.2% of all cancer-related deaths in the USA. Worldwide, there are approximately 176,000 new cases of brain and other CNS tumors per year, with an estimated mortality of 128,000. In general, the incidence of primary brain tumors is higher in whites than in blacks, and mortality is higher in males than in females. The peak incidence occurs between the ages of 45 and 70 years.

Primary brain tumors rarely spread to other areas of the body, but they can spread to other parts of the brain and to the spinal axis. Most patients with central nervous system (CNS) neoplasms do not live long enough to develop metastatic disease.

Glioblastoma Diagnosis:

Computed tomography (CT) and magnetic resonance imaging (MRI) have complementary roles in the diagnosis of CNS neoplasms. Angiography can also be used in diagnosis. In post-therapy imaging, single-photon emission computed tomography (SPECT) and positron emission tomography (PET) may be useful in differentiating tumor recurrence from radiation necrosis. A definite diagnosis is then made by performing a biopsy.

Glioblastoma Staging:

Glioblastomas are among the most aggressively malignant human neoplasms, with a mean total length of disease in patients with primary glioblastoma of less than 1 year. On the WHO classification of nervous system tumors from grade I to grade IV, glioblastoma is classified as grade IV. The 5-year survival rate for patients with glioblastoma aged over 45 is 2% or less.

Glioblastoma Treatment:

The cure rate for glioblastoma is very low with standard local treatment. The first step in most cases is surgical removal by craniotomy of as much of the tumor as is safe without destroying normal function. Glioblastomas are not cured by surgery because cells from the tumor get too far into the normal surrounding brain tissue. However, surgery reduces the pressure of the tumor against the rest of the brain and can prolong life even though all of the tumor can't be removed.

Radiation therapy (external beam radiation, interstitial radiotherapy, 3D conformal therapy, stereotactic radiosurgery or brachytherapy) can increase the cure rate or prolong disease-free survival. Radiation therapy may also be useful in the treatment of recurrences in patients initially treated with surgery alone. Therapy can involve surgically implanted carmustine-impregnated polymer combined with postoperative external-beam radiation therapy (EBRT).

Chemotherapy is usually given along with or following radiation therapy and may prolong survival. Chemotherapeutic agents used include temozolomide, BCNU (carmustine) and cisplatin. Growth factor inhibitors erlotinib (Tarceva) and gefitinib (Iressa) have been shown to shrink tumors in some patients.

Novel biologic therapies under clinical evaluation for patients with brain tumors include dendritic cell vaccination, tyrosine kinase receptor inhibitors, farnesyl transferase inhibitors, viral-based gene therapy, and oncolytic viruses.

Lung Cancer

Lung cancer is the most common form of cancer worldwide (accounting for about 12% of cancer cases) and the main cause of death from cancer (accounting for about 18% of deaths). Global incidence of lung cancer is over 1,300,000 per year, with the number of deaths over 1,100,000. In the USA, there are about 170,000 new cases per year (about 13% of all cancers), with about 160,000 deaths (about 28% of cancer deaths). Lung cancer is much more prevalent among men than women. Nearly 70% of people diagnosed with lung cancer are older than 65; fewer than 3% of all cases are found in people under the age of 45. Around 15% of all lung cancers are small cell type (SCLC), which tend to spread widely through the body, while the remaining 85% are non-small cell (NSCLC). It has been estimated that approximately US $9.6 billion is spent in the USA each year on treating lung cancer.

Lung Cancer Diagnosis

Lung cancer is a life-threatening disease because it often metastasises even before it can be detected on a chest x-ray. Usually symptoms of lung cancer do not appear until the disease is in an advanced stage. So far, there is no screening test that has been shown to improve a person's chance for a cure. Imaging tests such as a chest x-ray, CT scan, MRI scan or PET scan may be used to detect lung cancer. Tests to confirm the diagnosis are then performed and include sputum cytology, needle biopsy, bronchoscopy, endobronchial ultrasound and complete blood count (CBC).

Lung Cancer Staging

Nearly 60% of people diagnosed with lung cancer die within one year of diagnosis; 75% die within 2 years. The 5-year survival rate for people diagnosed with NSCLC is about 15%; for SCLC the 5-year survival rate is about 6%. NSCLC is staged using the American Joint Committee on Cancer (AJCC) TNM system—Stage 0-Stage IV. The 5-year survival rates by stage are as follows: stage I: 47%; stage II; 26%; stage III: 8% and stage IV: 2%. SCLC has a 2-stage system—limited stage and extensive stage. About two thirds of SCLC patients have extensive disease at diagnosis. If SCLC is found very early and is localised to the lung alone, the 5-year survival rate is around 21%, but only 6% of patients fall into this category. Where the cancer has spread, the 5-year survival is around 11%. For patients with extensive disease, the 5-year survival is just 2%.

Lung Cancer Treatment

Surgery is the only reliable method to cure NSCLC. Types of surgery include lobectomy, pneumonectomy, segmentectomy and video-assisted thoracic surgery (for small tumours). External beam radiation therapy is sometimes used as the primary treatment, especially if the patient's health is too poor to undergo surgery. Radiation therapy can also be used after surgery. Chemotherapy may be given as the primary treatment or as an adjuvant to surgery. Targeted therapy using epidermal growth factor receptor (EGFR) antagonists such as gefitinib or erlotinib can also be given after other treatments have failed. Antiangiogenic drugs, such as bevacizumab, have been found to prolong survival of patients with advanced lung cancer. Photodynamic therapy is also being researched as a treatment for lung cancer.

The main treatment for SCLC is chemotherapy, either alone or in combination with external beam radiation therapy and very rarely, surgery.

Chemotherapeutic agents used for NSCLC and SCLC include cisplatin, carboplatin, mitomycin C, ifosfamide, vinblastine, gemcitabine, etoposide, vinorelbine, paclitaxel, docetaxel and irinotecan.

Therapeutic Challenges

The major challenges in treatment of the above mentioned cancers are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells, e.g. ones which are expressed on the surface of the tumour cells so that they can be attacked by promising new approaches like immunotherapeutics and targeted toxins.

SUMMARY OF THE INVENTION

The present invention provides methods and compositions for screening, diagnosis, prognosis and therapy of HCC, glioblastoma and lung cancer, for HCC, glioblastoma and lung cancer patients' stratification, for monitoring the effectiveness of HCC, glioblastoma and lung cancer treatment, and for drug development for treatment of HCC, glioblastoma and lung cancer.

We have used mass spectrometry to identify peptides generated by gel electrophoresis and tryptic digest of membrane proteins extracted from HCC and glioblastoma tissue samples. Peptide sequences were compared to existing protein and cDNA databases and the corresponding gene sequences identified. The protein of the invention has not been previously reported to originate from HCC, glioblastoma or lung cancer cell membranes and represents a protein of new diagnostic and therapeutic value.

Thus, a first aspect of the invention provides methods for diagnosis of HCC, glioblastoma and lung cancer that comprises analysing a sample of liver, glioblastoma or lung tissue eg by gel electrophoresis or other appropriate protein separation technique to detect the protein of the invention. These methods are also suitable for screening, prognosis, monitoring the results of therapy, drug development and discovery of new targets for drug treatment.

A second aspect of the invention provides methods of treating HCC, glioblastoma and lung cancer, comprising administering to a patient a therapeutically effective amount of a compound that modulates (e.g., upregulates or downregulates) or complements the expression or the biological activity (or both) of the protein of the invention in patients having HCC, glioblastoma or lung cancer, in order to (a) prevent the onset or development of HCC, glioblastoma or lung cancer; (b) prevent the progression of HCC, glioblastoma or lung cancer; or (c) ameliorate the symptoms of HCC, glioblastoma or lung cancer.

A third aspect of the invention provides methods of screening for compounds that modulate (e.g., upregulate or downregulate) the expression or biological activity of the protein of the invention.

A fourth aspect of the invention provides monoclonal and polyclonal antibodies or other affinity reagents such as Affibodies, Nanobodies or Unibodies capable of immunospecific binding to the protein of the invention.

Thus, in a fifth aspect, the present invention provides a method for screening for and/or diagnosis of HCC, glioblastoma and lung cancer in a human subject, which method comprises the step of identifying the presence or absence of the protein of the invention, in a biological sample obtained from said human subject.

In a sixth aspect, the present invention provides a method for monitoring and/or assessing HCC, glioblastoma and lung cancer treatment in a human subject, which comprises the step of identifying the presence or absence of the protein of the invention, in a biological sample obtained from said human subject.

In a seventh aspect, the present invention provides a method for identifying the presence or absence of metastatic HCC or lung cancer cells in a biological sample obtained from a human subject, which comprises the step of identifying the presence or absence of the protein of the invention.

In an eighth aspect, the present invention provides a method for monitoring and/or assessing HCC, glioblastoma and lung cancer treatment in a human subject, which comprises the step of determining whether the protein of the invention is increased/decreased in a biological sample obtained from a patient.

The biological sample used can be from any source such as a serum sample or a tissue sample, e.g. liver, glioblastoma or lung tissue. For instance, when looking for evidence of metastatic HCC or lung cancer, one would look at major sites of HCC or lung cancer metastasis, e.g. the lungs and bones for HCC and the brain, liver, bones and adrenal glands for lung cancer.

Other aspects of the present invention are set out below and in the claims herein.

BRIEF DESCRIPTION OF THE FIGURES

FIG. 1A-1E shows the amino acid sequences of the two isoforms of the protein of the invention. The tryptics detected experimentally by mass spectrometry are highlighted—mass match peptides are shown in bold, tandem peptides are underlined.

FIG. 4 shows the sequence of the protein of the invention used for immunization (this includes a synthetic signal sequence for secretion).

DETAILED DESCRIPTION OF THE INVENTION

Figure 2A:
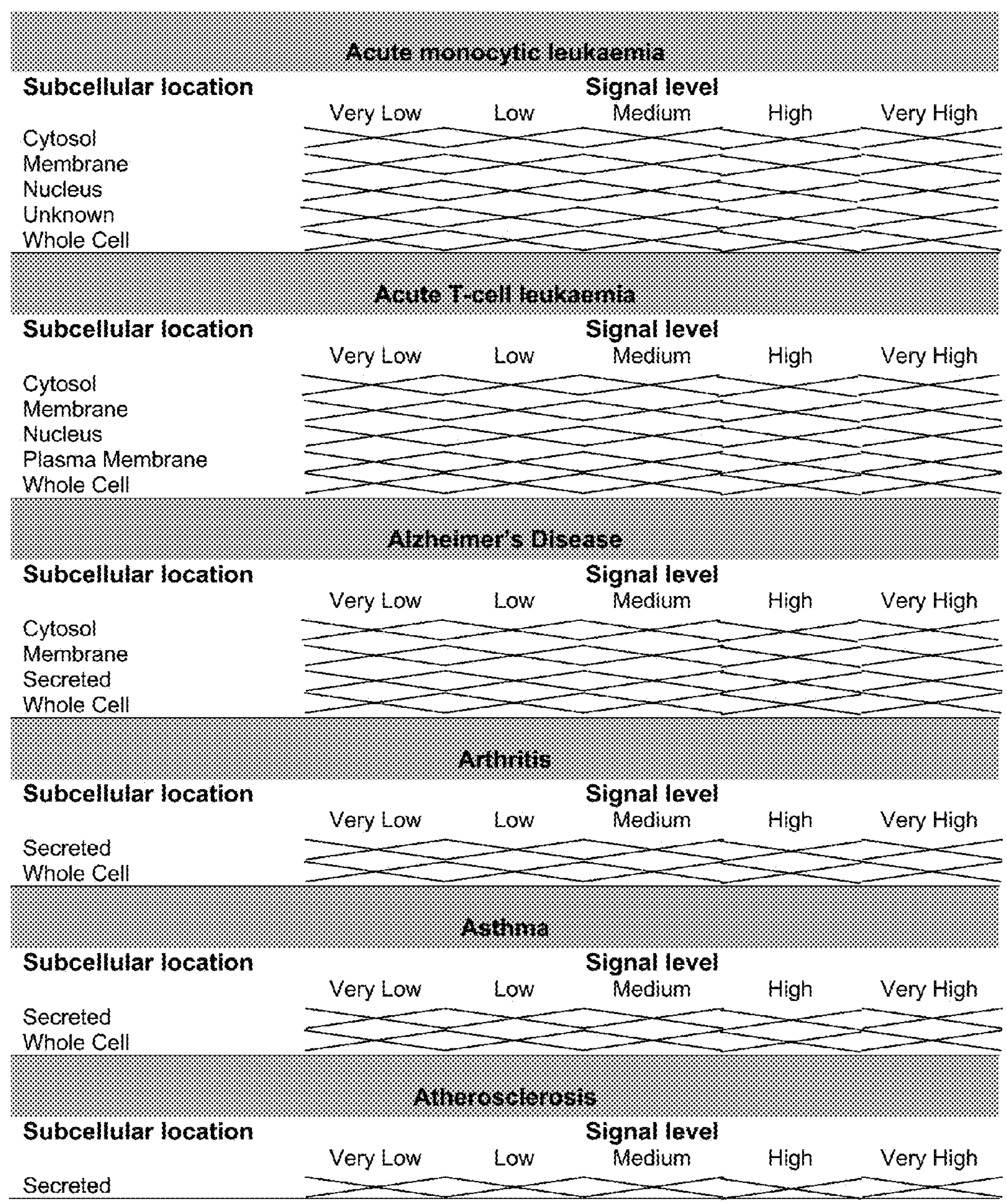
FIG. 2A-2J shows the Protein Index for the protein of the invention.
Figure 2B:
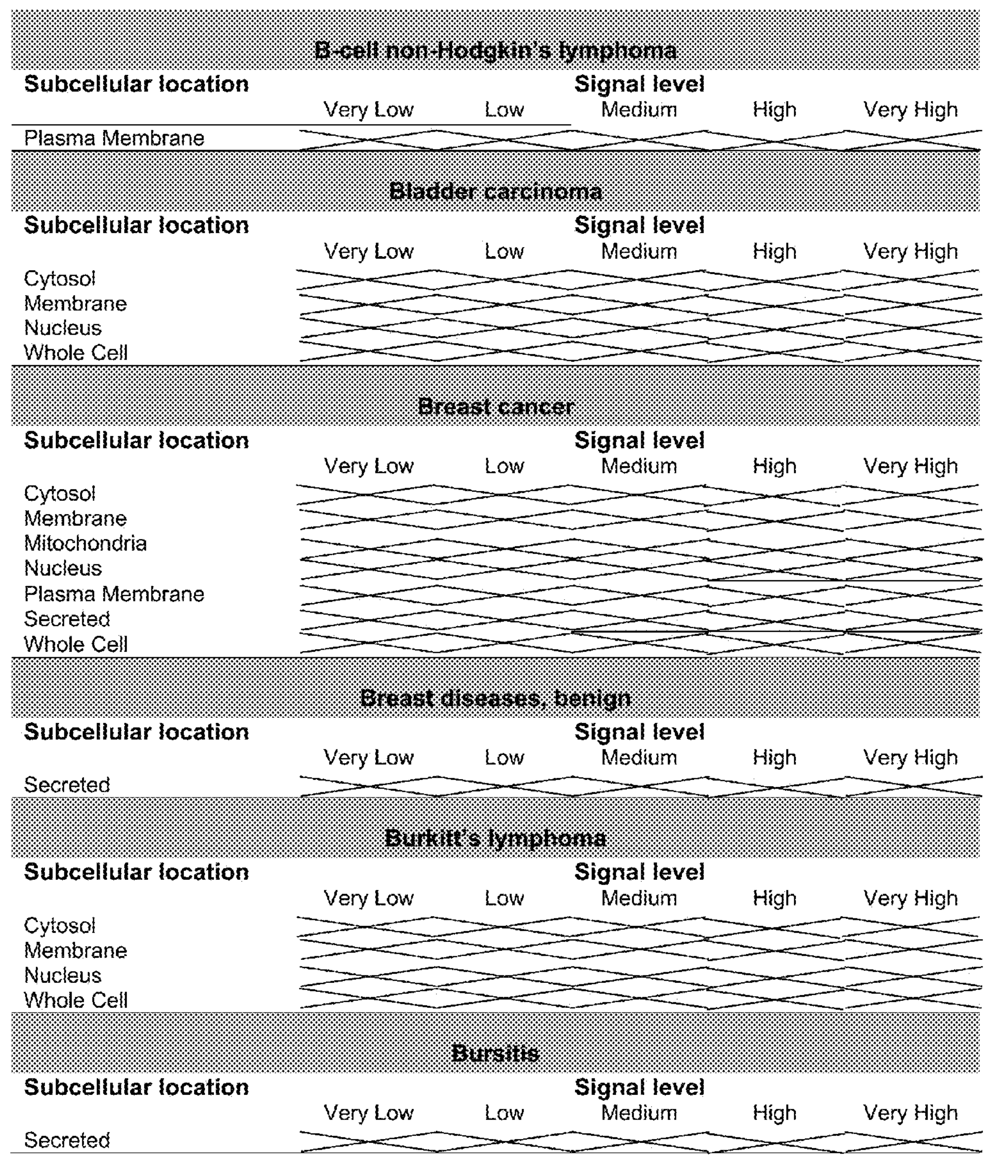
Figure 2C:
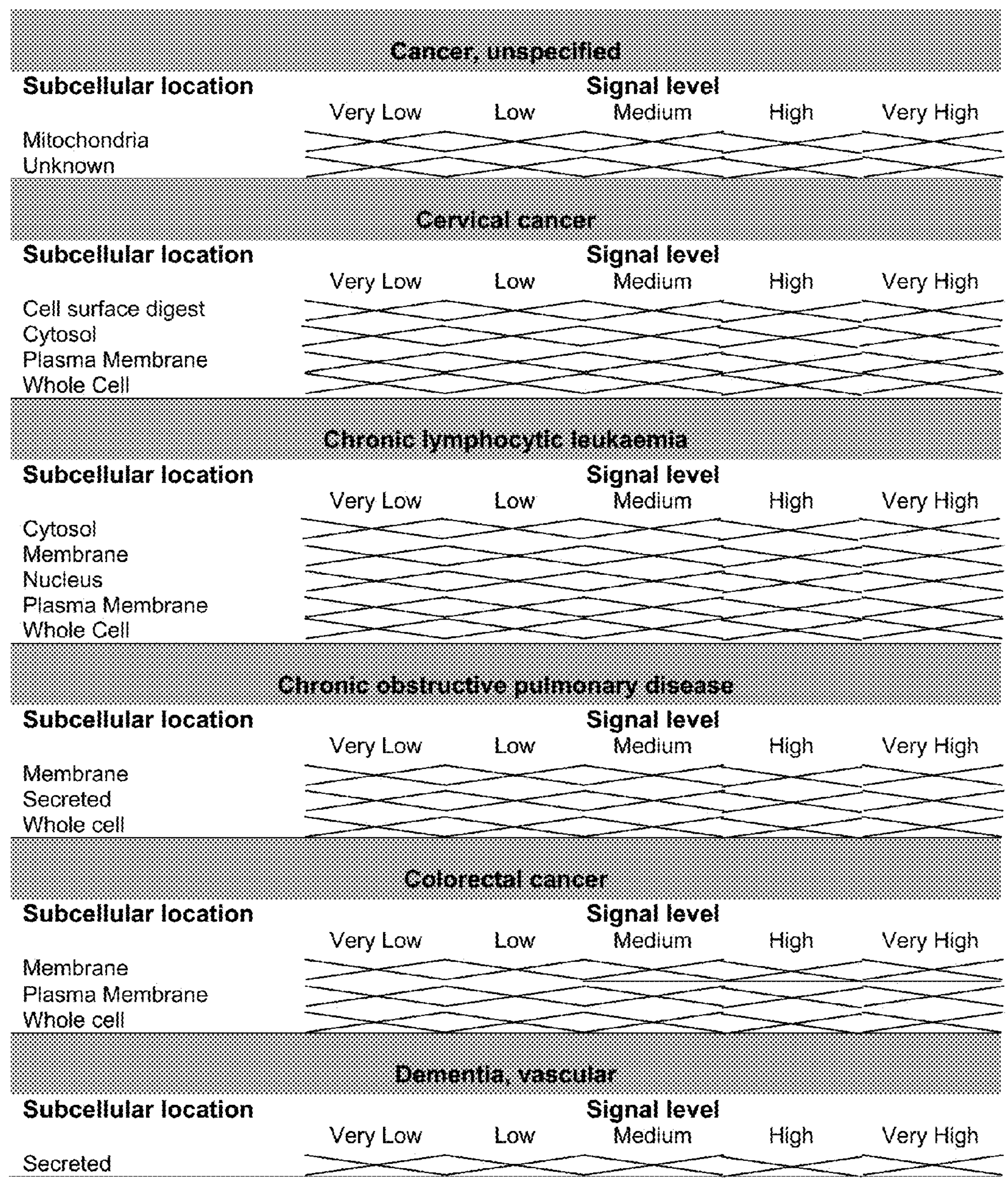
Figure 2D:
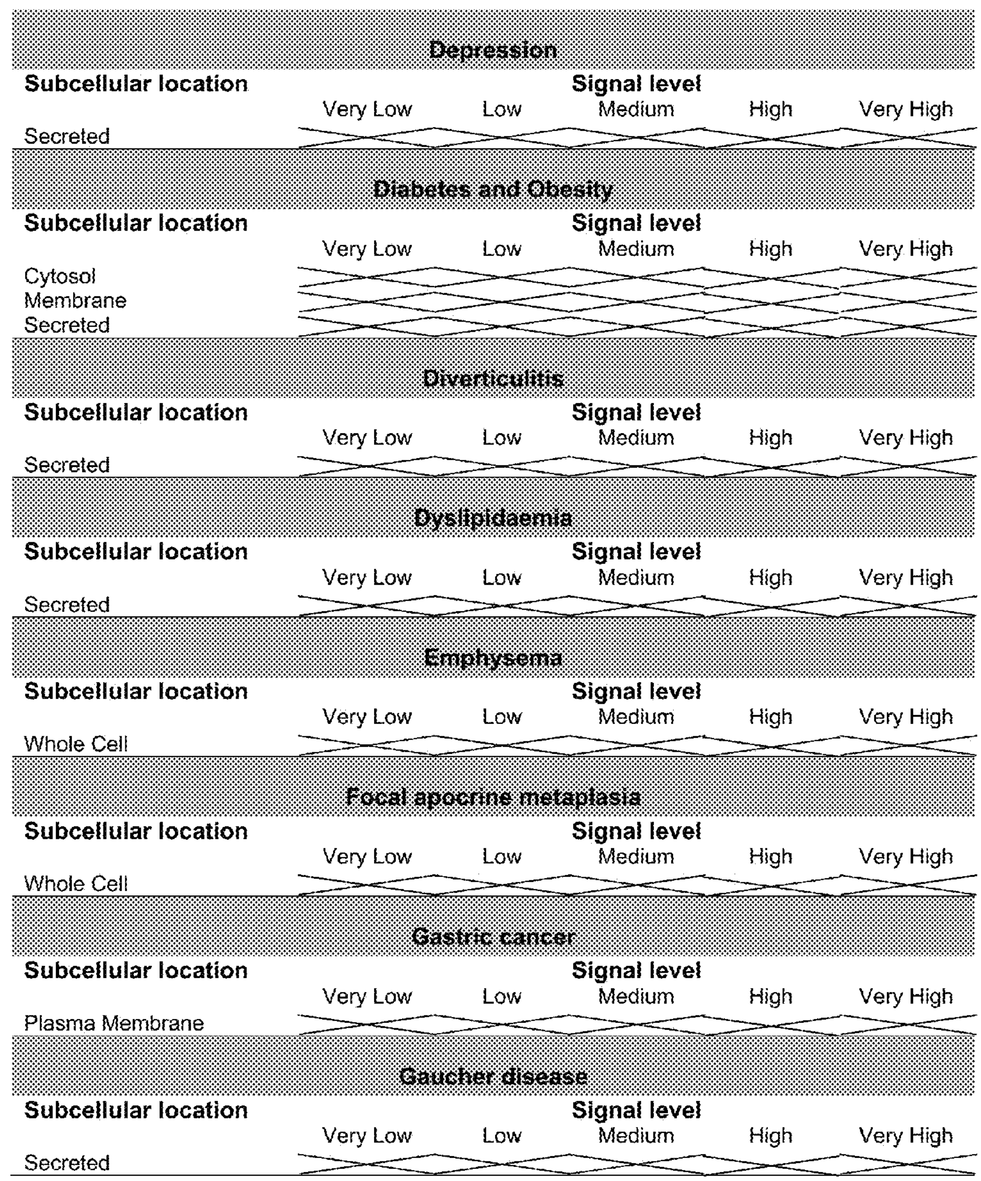
Figure 2E:
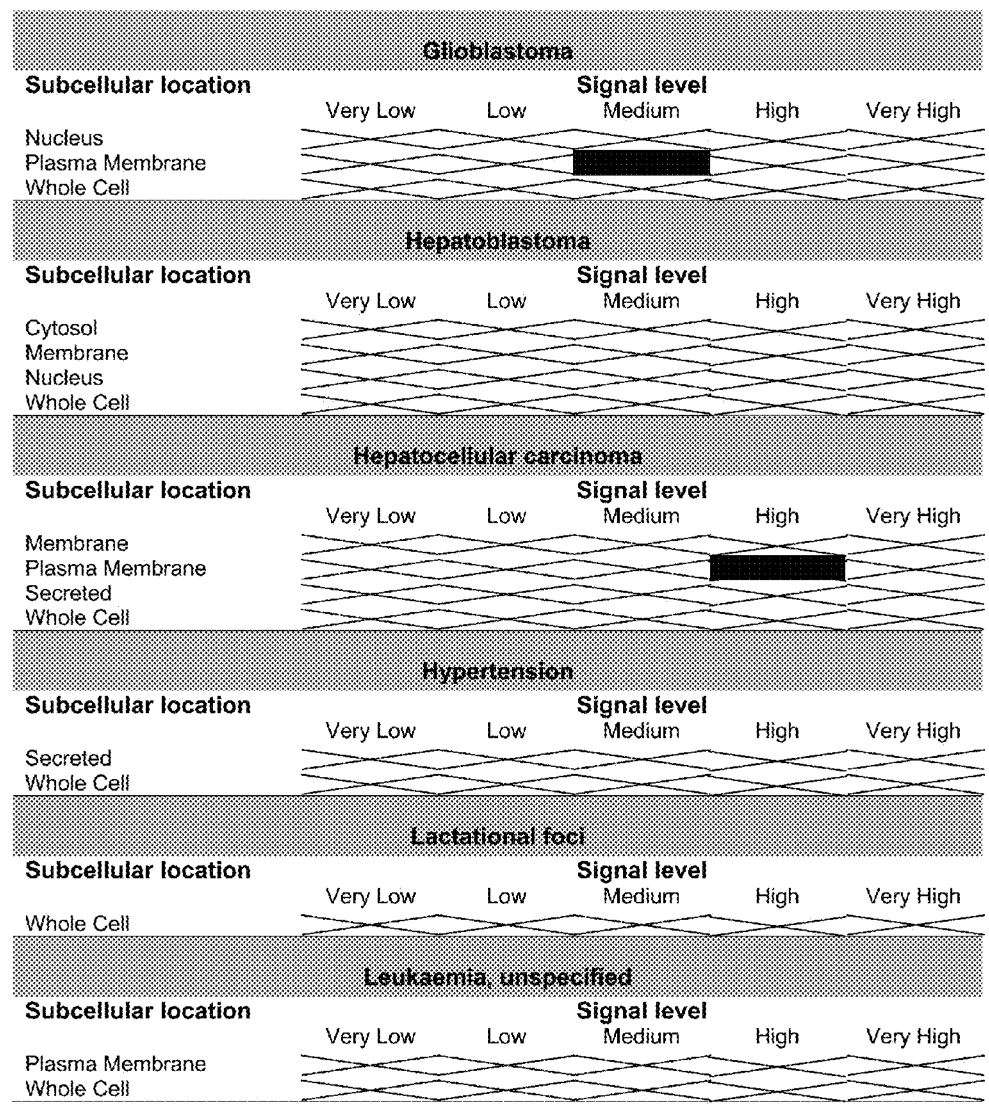
Figure 2F:
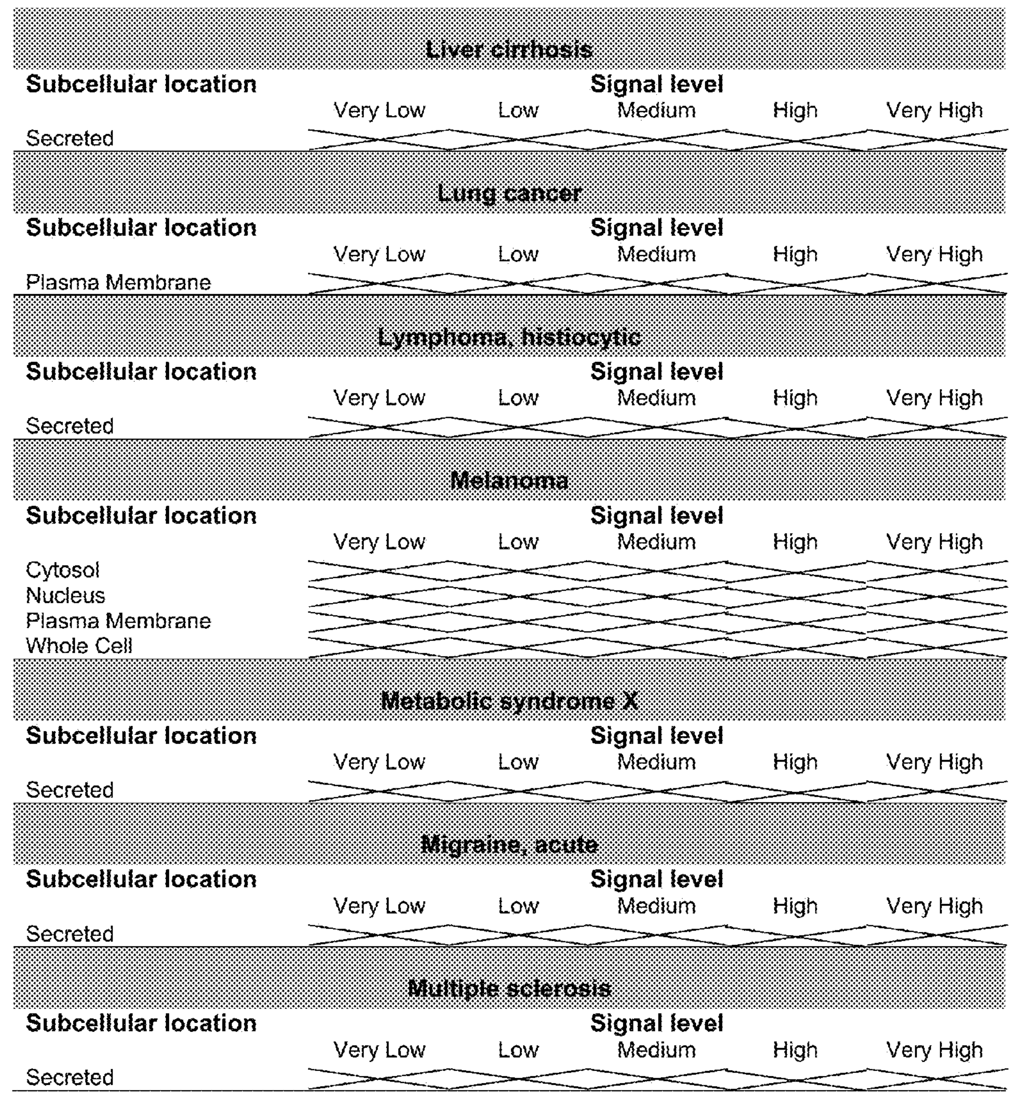
Figure 2G:
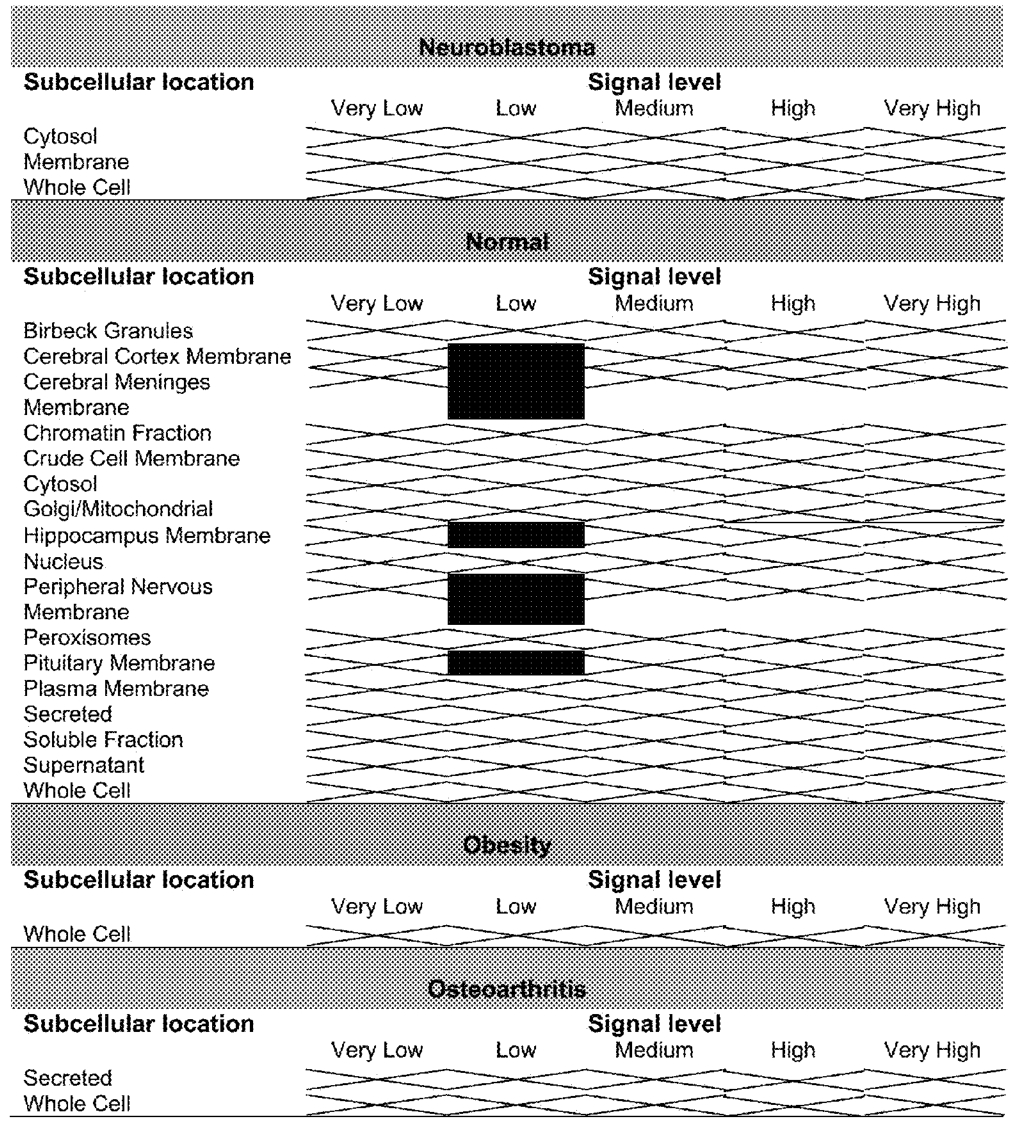
Figure 2H:
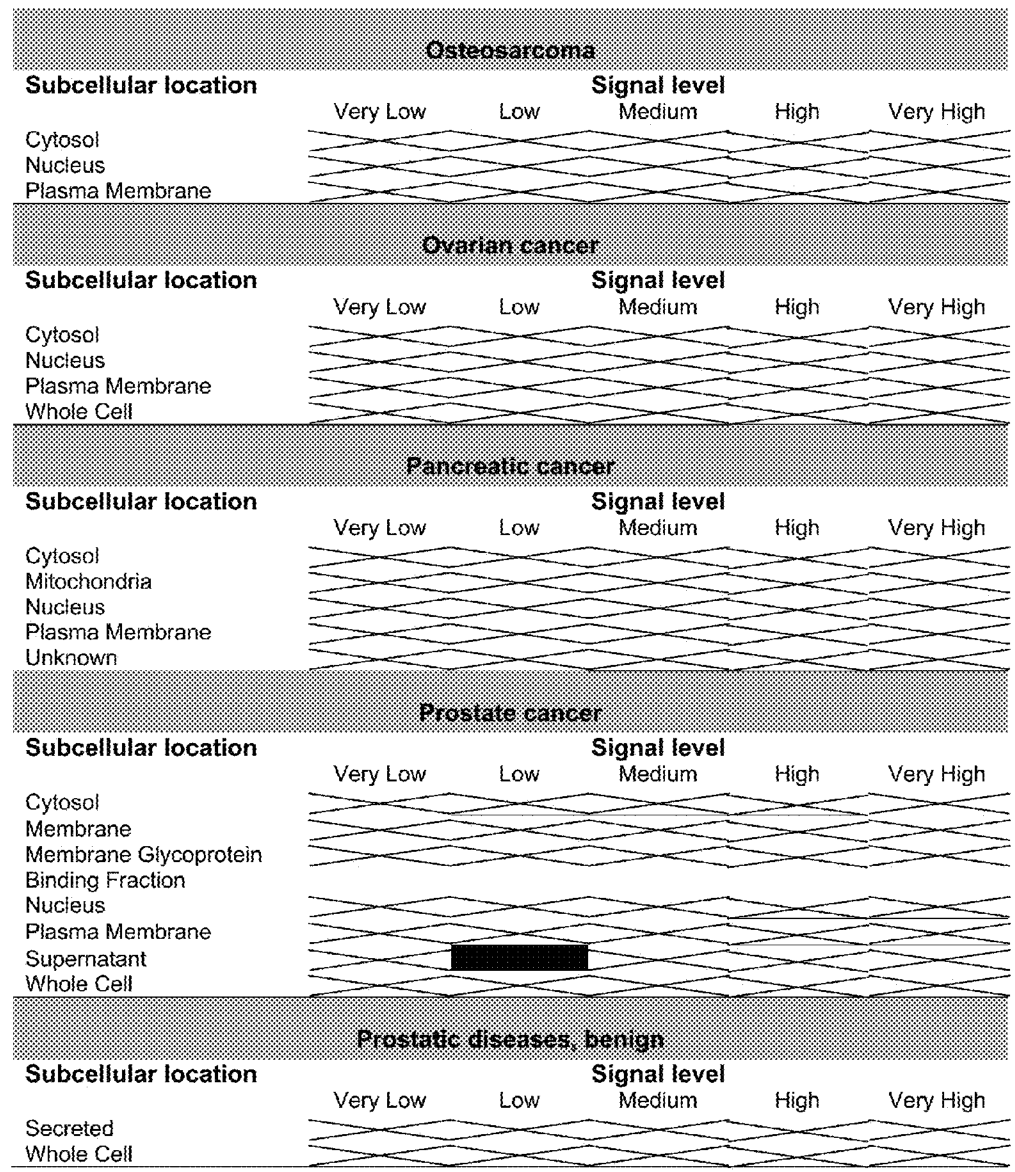
Figure 2I:
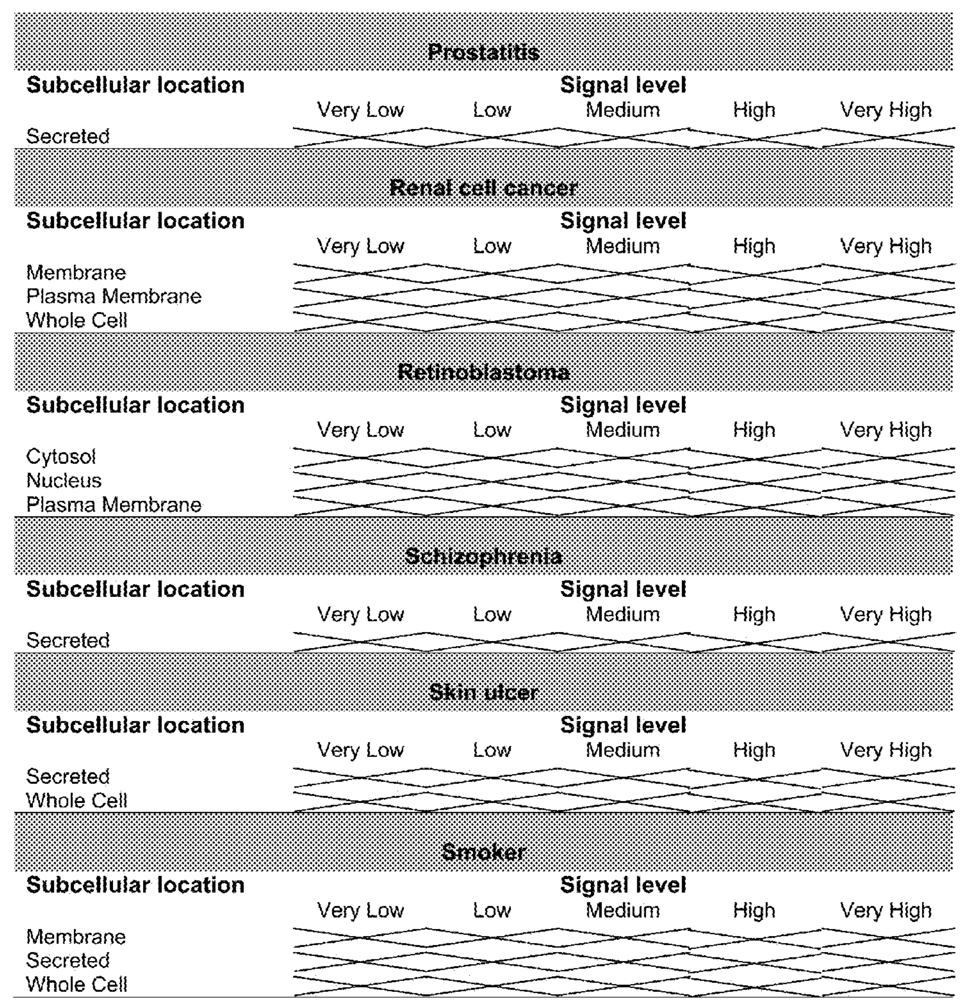
Figure 2J:
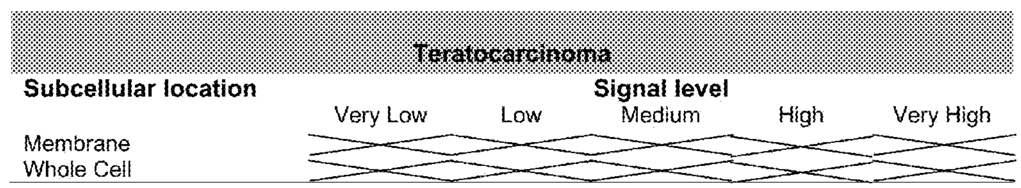

The invention described in detail below provides methods and compositions for clinical screening, diagnosis and prognosis of HCC, glioblastoma and lung cancer in a mammalian subject for identifying patients most likely to respond to a particular therapeutic treatment, for monitoring the results of HCC, glioblastoma and lung cancer therapy, for drug screening and drug development. The invention also encompasses the administration of therapeutic compositions to a mammalian subject to treat or prevent HCC, glioblastoma and lung cancer. The mammalian subject may be a non-human mammal, but is preferably human, more preferably a human adult, i.e. a human subject at least 21 (more preferably at least 35, at least 50, at least 60, at least 70, or at least 80) years old. For clarity of disclosure, and not by way of limitation, the invention will be described with respect to the analysis of liver, glioblastoma and lung tissue. However, as one skilled in the art will appreciate, the assays and techniques described below can be applied to other types of patient samples, including body fluids (e.g. blood, urine or saliva), a tissue sample from a patient at risk of having HCC, glioblastoma and lung cancer (e.g. a biopsy such as a liver, brain or lung biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

OGTA025

In one aspect of the invention, one-dimensional electrophoresis is used to analyze HCC, glioblastoma or lung cancer tissue samples from a subject, preferably a living subject, in order to measure the expression of the protein of the invention for screening or diagnosis of HCC, glioblastoma or lung cancer, to determine the prognosis of a HCC, glioblastoma or lung cancer patient, to monitor the effectiveness of HCC, glioblastoma or lung cancer therapy, or for drug development.

As used herein, the term "Protein of the invention", or "OGTA025", refers to the protein illustrated in FIG. 1 in all its isoforms, in particular in its two different isoforms detected experimentally by 1D electrophoresis of liver and glioblastoma tissue samples (OGTA025a (SEQ ID No: 1) and OGTA025b (SEQ ID No: 2)). Protein derivatives of these sequences may also be useful for the same purposes as described herein.

This protein has been identified in membrane protein extracts of liver and glioblastoma tissue samples from HCC and glioblastoma patients, through the methods and apparatus of the Preferred Technology (1D gel electrophoresis and tryptic digest of membrane protein extracts). Peptide sequences were compared to the SWISS-PROT and trEMBL databases (held by the Swiss Institute of Bioinformatics (SIB) and the European Bioinformatics Institute (EBI)), and the following entries: Q8N2F4 and Q9BY67 were identified. Peptide sequences were also compared to the Ensembl database (a joint project between EMBL-EBI and the Sanger Institute) and the following entry: ENSG00000182985, IGSF4, was identified.

According to SWISS-PROT, IGSF4 is a membrane glycoprotein with an extracellular domain homologous to those of immunoglobulin superfamily proteins. It may act as a tumor antigen recognized by activated NK or CD8+ T cells; it triggers NK-cell and CD8+ T-cell responses through the cell-surface receptor class-I-restricted T-cell-associated molecule, CRTAM (a receptor primarily expressed on activated cytotoxic lymphocytes). When present on antigen presenting cells, it regulates IL-22 expression by activated CD8+ T-cells. The IGSF4/CRTAM molecular pair could regulate a large panel of cell/cell interactions both within and outside of the immune system.

OGTA025 is also indicated to be expressed in lung cancer. Quantitative reverse transcriptase polymerase chain reaction (RT-PCR) results (see Example 2 and FIG. 3) showed high mRNA expression of OGTA025 in lung cancer, particularly small cell lung cancer. mRNA expression is an indication of OGTA025 protein expression. Fluorescence-activated cell sorting (FACS) analysis (see Example 5 and FIG. 5) indicated that a number of the OGTA025 antibodies generated in Example 3 bind well to NCI-H69 lung cancer cells. Immunohistochemistry experiments (see Example 6) also showed strong staining in a vast majority of tumour cells in 5/7 small cell lung cancer samples.

The protein of the invention is useful as are fragments e.g. antigenic or immunogenic fragments thereof and derivatives thereof. Antigenic or immunogenic fragments will typically be of length 12 amino acids or more e.g. 20 amino acids or more e.g. 50 or 100 amino acids or more. Fragments may be 10% or more of the length of the full protein e.g. 25% or more e.g. 50% or 75% or 90% or 95% or more of the length of the full protein.

Antigenic or immunogenic fragments will be capable of eliciting a relevant immune response in a patient. DNA encoding the protein of the invention is also useful as are fragments thereof e.g. DNA encoding fragments of the protein of the invention such as immunogenic fragments thereof. Fragments of nucleic acid (e.g. DNA) encoding the protein of the invention may be 10% or more of the length of the full coding region e.g. 25% or more e.g. 50% or 75% or 90% or 95% or more of the length of the full coding region. Fragments of nucleic acid (e.g. DNA) may be 36 nucleotides or more e.g. 60 nucleotides or more e.g. 150 or 300 nucleotides or more in length.

Derivatives of the protein of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. For example derivatives may have sequence identity of 80% or more e.g. 90% or more e.g. 95% or more as compared with the reference sequence over the full length of the reference sequence. Derivatives will typically have essentially the same biological function as the protein from which they are derived. Derivatives will typically be comparably antigenic or immunogenic to the protein from which they are derived.

Tables 1a, 1b and 1c below illustrate the different occurrences of OGTA025 as detected by 1D gel electrophoresis and mass spectrometry of membrane protein extracts of liver, glioblastoma and lung cancer tissue samples from HCC, glioblastoma and lung cancer patients respectively. The first column provides the molecular weight, the second column gives information on the subfractionation protocol used, if any (see Example 1 below), and the last column provides a list of the sequences observed by mass spectrometry and the corresponding SEQ ID Nos.

Table 2 below illustrates the different occurrences of OGTA025 as detected by iTRAQ and mass spectrometry of membrane protein extracts of lung tissue samples from lung cancer patients. The first column provides the sample number, the second column gives information on the iTRAQ experiment number for that sample and the last column provides a list of the sequences observed by mass spectrometry and the corresponding SEQ ID Nos.

TABLE 1a

| HCC | | |
|---|---|---|
| MW (Da) | Subfractionation | Tryptics identified [SEQ ID No] |
| 68904 | | DFRPLK [6], QTIYFR [8], SDDSVIQLLNPNR [9] |
| 88086 | MonoQ Aqueous | AGEEGSIR [4], CEASNIVGK [5], DFRPLK [6], QTIYFR [8], SDDSVIQLLNPNR [9] |

TABLE 1b

| Glioblastoma | | |
|---|---|---|
| MW (Da) | Subfractionation | Tryptics identified [SEQ ID No] |
| 75255 | | CEASNIVGK [5], GTYFTHEAK [7], QTIYFR [8], SDDSVIQLLNPNR [9] |
| 89534 | | QTIYFR [8], SDDSVIQLLNPNR [9] |

TABLE 1c

| Lung cancer | | |
|---|---|---|
| MW (Da) | Subfractionation | Tryptics identified [SEQ ID No] |
| 72723 | | DVTVIEGEVATISCQVNK [11], EDDGVPVICQVEHPAVTGNLQTQR [12], EGDALELTCEAIGK [13], GTYFTHEAK [7], PQPVMVTVWR [19], PQVHIQMTYPLQGLTR [20], QTIYFR [8], SDDSVIQLLNPNR [9], TDNGTYR [21], YLEVQYK [24] |
| 85000 | | DTAVEGEEIEVNCTAMASK [10], DVTVIEGEVATISCQVNK [11], EGDALELTCEAIGK [13], FQLLNFSSSELK [14], LLLLLFSAAALIPTGDGQNLFTK [16], MASVVLPSGSQCAAAAAAAAPPGLR [17], NLMIDIQR [18], PQPVMVTWVR [19], PQVHIQMTYPLQGLTR [20], SDDSVIQLLNPNR [9], YFCQLYTDPPQESYTTITVLVPPR [23] |

TABLE 2

| Lung cancer iTRAQ | | |
|---|---|---|
| Sample no. | Experiment no. | Tryptics identified [SEQ ID No] |
| Sample 1 | Experiment 1 | AGEEGSIR [4], |

For OGTA025, the detected level obtained upon analyzing tissue from subjects having HCC, glioblastoma or lung cancer relative to the detected level obtained upon analyzing tissue from subjects free from HCC, glioblastoma and lung cancer will depend upon the particular analytical protocol and detection technique that is used. Accordingly, the present invention contemplates that each laboratory will establish a reference range in subjects free from HCC, glioblastoma and lung cancer according to the analytical protocol and detection technique in use, as is conventional in the diagnostic art. Preferably, at least one control positive tissue sample from a subject known to have HCC, glioblastoma or lung cancer or at least one control negative tissue sample from a subject known to be free from HCC, glioblastoma and lung cancer (and more preferably both positive and negative control samples) are included in each batch of test samples analysed.

OGTA025 can be used for detection, prognosis, diagnosis, or monitoring of HCC, glioblastoma and lung cancer or for drug development. In one embodiment of the invention, tissue from a subject (e.g., a subject suspected of having HCC, glioblastoma or lung cancer) is analysed by 1D electrophoresis for detection of OGTA025. An increased abundance of OGTA025 in the tissue from the subject relative to tissue from a subject or subjects free from HCC, glioblastoma and lung cancer (e.g., a control sample) or a previously determined reference range indicates the presence of HCC, glioblastoma or lung cancer.

In relation to variants, fragments, immunogenic fragments or antigenic fragments of OGTA025:

for HCC applications: preferably these comprise one or more of the sequences identified as tryptic sequences in the 3rd column of Table 1a;

for glioblastoma applications: preferably these comprise one or more of the sequences identified as tryptic sequences in the 3rd column of Table 1b.

OGTA025 may, in particular, be characterized as an isoform having a MW substantially as recited (eg +/−10%, particularly +/−5% of the value) in column 1 of any of the rows of Tables 1a or 1b.

The present invention additionally provides: (a) a preparation comprising isolated OGTA025; (b) a preparation comprising one or more fragments of OGTA025; and (c) antibodies or other affinity reagents such as Affibodies, Nanobodies or Unibodies that bind to OGTA025, to said fragments, or both to OGTA025 and to said fragments. As used herein, OGTA025 is “isolated” when it is present in a preparation that is substantially free of contaminating proteins, i.e., a preparation in which less than 10% (preferably less than 5%, more preferably less than 1%) of the total protein present is contaminating protein(s). A contaminating protein is a protein having a significantly different amino acid sequence from that of isolated OGTA025, as determined by mass spectral analysis. As used herein, a “significantly different” sequence is one that permits the contaminating protein to be resolved from OGTA025 by mass spectral analysis, performed according to the Reference Protocol.

OGTA025 can be assayed by any method known to those skilled in the art, including but not limited to, the Preferred Technology described herein, kinase assays, enzyme assays, binding assays and other functional assays, immunoassays, and western blotting. In one embodiment, OGTA025 is separated on a 1-D gel by virtue of its MW and visualized by staining the gel. In one embodiment, OGTA025 is stained with a fluorescent dye and imaged with a fluorescence scanner. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

Alternatively, OGTA025 can be detected in an immunoassay. In one embodiment, an immunoassay is performed by contacting a sample from a subject to be tested with an anti-OGTA025 antibody (or other affinity reagent such as an Affibody, Nanobody or Unibody) under conditions such that immunospecific binding can occur if OGTA025 is present, and detecting or measuring the amount of any immunospecific binding by the affinity reagent. Anti-OGTA025 affinity reagents can be produced by the methods and techniques taught herein.

OGTA025 may be detected by virtue of the detection of a fragment thereof eg an immunogenic or antigenic fragment thereof. Fragments may have a length of at least 10, more typically at least 20 amino acids eg at least 50 or 100 amino acids eg at least 200 amino acids.

In one embodiment, binding of antibody (or other affinity reagent such as an Affibody, Nanobody or Unibody) in tissue sections can be used to detect aberrant OGTA025 localization or an aberrant level of OGTA025. In a specific embodiment, an antibody (or other affinity reagent such as an Affibody, Nanobody or Unibody) to OGTA025 can be used to assay a patient tissue (e.g., liver, glioblastoma or lung tissue) for the level of OGTA025 where an aberrant level of OGTA025 is indicative of HCC, glioblastoma or lung cancer. As used herein, an “aberrant level” means a level that is increased compared with the level in a subject free from HCC, glioblastoma and lung cancer or a reference level.

Any suitable immunoassay can be used, including, without limitation, competitive and non-competitive assay systems using techniques such as western blots, radioimmunoassays, ELISA (enzyme linked immunosorbent assay), “sandwich” immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, OGTA025 can be detected in a fluid sample (e.g., blood, urine, or saliva) by means of a two-step sandwich assay. In the first step, a capture reagent (e.g., an anti-OGTA025 antibody or other affinity reagent such as an Affibody, Nanobody or Unibody) is used to capture OGTA025. The capture reagent can optionally be immobilized on a solid phase. In the second step, a directly or indirectly labeled detection reagent is used to detect the captured OGTA025. In one embodiment, the detection reagent is a lectin. Any lectin can be used for this purpose that preferentially binds to OGTA025 rather than to other isoforms that have the same core protein as OGTA025 or to other proteins that share the antigenic determinant recognized by the affinity reagent. In a preferred embodiment, the chosen lectin binds OGTA025 with at least 2-fold greater affinity, more preferably at least 5-fold greater affinity, still more preferably at least 10-fold greater affinity, than to said other isoforms that have the same core protein as OGTA025 or to said other proteins that share the antigenic determinant recognized by the affinity reagent. Based on the present description, a lectin that is suitable for detecting OGTA025 can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent such as an Affibody, Nanobody or Unibody), e.g., an antibody that immunospecifically detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding OGTA025, a related gene, or related nucleic acid sequences or subsequences, including complementary sequences, can also be used in hybridization assays. A nucleotide encoding OGTA025, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding OGTA025, or for differential diagnosis of subjects with signs or symptoms suggestive of HCC, glioblastoma or lung cancer. In particular, such a hybridization assay can be carried out by a method comprising contacting a subject's sample containing nucleic acid with a nucleic acid probe capable of hybridizing to a DNA or RNA that encodes OGTA025, under conditions such that hybridization can occur, and detecting or measuring any resulting hybridization.

The invention also provides diagnostic kits, comprising an anti-OGTA025 antibody (or other affinity reagent such as an Affibody, Nanobody or Unibody). In addition, such a kit may optionally comprise one or more of the following: (1) instructions for using the anti-OGTA025 affinity reagent for diagnosis, prognosis, therapeutic monitoring or any combination of these applications; (2) a labeled binding partner to the affinity reagent; (3) a solid phase (such as a reagent strip) upon which the anti-OGTA025 affinity reagent is immobilized; and (4) a label or insert indicating regulatory approval for diagnostic, prognostic or therapeutic use or any combination thereof. If no labeled binding partner to the affinity reagent is provided, the anti-OGTA025 affinity reagent itself can be labeled with a detectable marker, e.g., a chemiluminescent, enzymatic, fluorescent, or radioactive moiety.

The invention also provides a kit comprising a nucleic acid probe capable of hybridizing to RNA encoding OGTA025. In a specific embodiment, a kit comprises in one or more containers a pair of primers (e.g., each in the size range of 6-30 nucleotides, more preferably 10-30 nucleotides and still more preferably 10-20 nucleotides) that under appropriate reaction conditions can prime amplification of at least a portion of a nucleic acid encoding OGTA025, such as by polymerase chain reaction (see, e.g., Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of OGTA025 or a nucleic acid encoding OGTA025, e.g., for use as a standard or control.

Use in Clinical Studies

The diagnostic methods and compositions of the present invention can assist in monitoring a clinical study, e.g. to evaluate drugs for therapy of HCC, glioblastoma or lung cancer. In one embodiment, candidate molecules are tested for their ability to restore OGTA025 levels in a subject having HCC, glioblastoma or lung cancer to levels found in subjects free from HCC, glioblastoma and lung cancer or, in a treated subject, to preserve OGTA025 levels at or near non-HCC, non-glioblastoma or non-lung cancer values.

In another embodiment, the methods and compositions of the present invention are used to screen candidates for a clinical study to identify individuals having HCC, glioblastoma or lung cancer; such individuals can then be excluded from the study or can be placed in a separate cohort for treatment or analysis.

Production of Protein of the Invention and Corresponding Nucleic Acid

A DNA of the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined. Furthermore, databases of known genes are searched for homology using the thus obtained terminal nucleotide sequences as queries. The entire nucleotide sequence of a clone revealed to be novel as a result is determined. In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from liver, glioblastoma or lung tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of OGTA025 or DNA encoding the above polypeptide consisting of an amino acid sequence derived from the amino acid sequence of OGTA025 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of OGTA025 and DNA hybridizing under stringent conditions to the DNA and encoding a polypeptide (protein) having biological activity (function) equivalent to the function of the polypeptide consisting of the amino acid sequence of OGTA025. Under such conditions, an example of such DNA capable of hybridizing to DNA comprising the nucleotide sequence that encodes the amino acid sequence of OGTA025 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

Where it is provided for use with the methods of the invention OGTA025 is preferably provided in isolated form. More preferably the OGTA025 polypeptide has been purified to at least to some extent. OGTA025 polypeptide may be provided in substantially pure form, that is to say free, to a substantial extent, from other proteins. OGTA025 polypeptide can also be produced using recombinant methods, synthetically produced or produced by a combination of these methods. OGTA025 can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

Recombinant OGTA025 polypeptide may be prepared by processes well known in the art from genetically engineered host cells comprising expression systems. Accordingly, the present invention also relates to expression systems which comprise an OGTA025 polypeptide or nucleic acid, to host cells which are genetically engineered with such expression systems and to the production of OGTA025 polypeptide by recombinant techniques. For recombinant OGTA025 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N Y, 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127, 3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda] phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an lpp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRa promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the OGTA025 polypeptide to allow secretion of the translated protein into the lumen of the endoplasmic reticulum, the periplasmic space or the extracellular environment. These signals may be endogenous to the OGTA025 polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If an OGTA025 polypeptide is to be expressed for use in cell-based screening assays, it is preferred that the polypeptide be produced at the cell surface. In this event, the cells may be harvested prior to use in the screening assay. If the OGTA025 polypeptide is secreted into the medium, the medium can be recovered in order to isolate said polypeptide. If produced intracellularly, the cells must first be lysed before the OGTA025 polypeptide is recovered.

OGTA025 polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an OGTA025 polypeptide can be used to deplete a sample comprising an OGTA025 polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the OGTA025 polypeptide when the polypeptide has been denatured during isolation and or purification. In the context of the present invention, OGTA025 polypeptide can be obtained from a biological sample from any source, such as and without limitation, a blood sample or tissue sample, e.g. a liver, glioblastoma or lung tissue sample.

OGTA025 polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

An additional sequence that may provide stability during recombinant production may also be used. Such sequences may be optionally removed as required by incorporating a cleavable sequence as an additional sequence or part thereof. Thus, an OGTA025 polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to OGTA025

According to those in the art, there are three main types of affinity reagent—monoclonal antibodies, phage display antibodies and small molecules such as Affibodies, Domain Antibodies (dAbs), Nanobodies or Unibodies. In general in applications according to the present invention where the use of antibodies is stated, other affinity reagents (e.g. Affibodies, domain antibodies, Nanobodies or Unibodies) may be employed.

Production of Antibodies to OGTA025

According to the invention OGTA025, an OGTA025 analog, an OGTA025-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental *Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody." Antibodies of the invention include, but are not limited to polyclonal, monoclonal, bispecific, humanized or chimeric antibodies, single chain antibodies, Fab fragments and $F(ab')_2$ fragments, fragments produced by a Fab expression library, anti-idiotypic (anti-Id) antibodies, and epitope-binding fragments of any of the above. The immunoglobulin molecules of the invention can be of any class (e.g., IgG, IgE, IgM, IgD and IgA) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Specific binding between an antibody or other binding agent and an antigen means a binding affinity of at least $10^6$ $M^{-1}$. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$ or about $10^{10}$ $M^{-1}$ to about $10^{11}$ $M^{-1}$.

Affinity is calculated as $K_d=k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c=K(n-r)$:

where r=moles of bound ligand/mole of receptor at equilibrium;

c=free ligand concentration at equilibrium;

K=equilibrium association constant; and n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1\times10^{-6}$ moles/liter, is more preferably at least about $1\times10^{-7}$ moles/liter, is even more preferably at least about $1\times10^{-8}$ moles/liter, is yet even more preferably at least about $1\times10^{-9}$ moles/liter, and is most preferably at least about $1\times10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding OGTA025 are publicly available. In another embodiment, methods known to those skilled in the art are used to produce antibodies that recognize OGTA025, an OGTA025 analog, an OGTA025-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of OGTA025 are produced. In a specific embodiment, hydrophilic fragments of OGTA025 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of OGTA025, one may assay generated hybridomas for a product which binds to an OGTA025 fragment containing such domain. For selection of an antibody that specifically binds a first OGTA025 homolog but which does not specifically bind to (or binds less avidly to) a second OGTA025 homolog, one can select on the basis of positive binding to the first OGTA025 homolog and a lack of binding to (or reduced binding to) the second OGTA025 homolog. Similarly, for selection of an antibody that specifically binds OGTA025 but which does not specifically bind to (or binds less avidly to) a different isoform of the same protein (such as a different glycoform having the same core peptide as OGTA025), one can select on the basis of positive binding to OGTA025 and a lack of binding to (or reduced binding to) the different isoform (e.g., a different glycoform). Thus, the present invention provides an antibody (preferably a monoclonal antibody) that binds with greater affinity (preferably at least 2-fold, more preferably at least 5-fold, still more preferably at least 10-fold greater affinity) to OGTA025 than to a different isoform or isoforms (e.g., glycoforms) of OGTA025.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to OGTA025, a fragment of OGTA025, an OGTA025-related polypeptide, or a fragment of an OGTA025-related polypeptide. For example, one way is to purify polypeptides of interest or to synthesize the polypeptides of interest using, e.g., solid phase peptide synthesis methods well known in the art. See, e.g., Guide to Protein Purification, Murray P. Deutcher, ed., *Meth. Enzymol. Vol* 182 (1990); Solid Phase Peptide Synthesis, Greg B. Fields ed., *Meth. Enzymol. Vol* 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. The Preferred Technology described herein provides isolated OGTA025 suitable for such immunization. If OGTA025 is purified by gel electrophoresis, OGTA025 can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

For preparation of monoclonal antibodies (mAbs) directed toward OGTA025, a fragment of OGTA025, an OGTA025-related polypeptide, or a fragment of an OGTA025-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g., human-mouse chimeras). A chimeric antibody is a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539;

Jones et al., 1986, Nature 321:552-525; Verhoeyan et al. (1988) Science 239:1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g., all or a portion of OGTA025. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12: 899-903).

The antibodies of the present invention can also be generated by the use of phage display technology to produce and screen libraries of polypeptides for binding to a selected target. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims. In particular, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121:210.

The invention provides functionally active fragments, derivatives or analogs of the anti-OGTA025 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, $F(ab')_2$ fragments and Fab fragments. Antibody fragments which recognize specific epitopes may be generated by known techniques. $F(ab')_2$ fragments consist of the variable region, the light chain constant region and the CH1 domain of the heavy chain and are generated by pepsin digestion of the antibody molecule. Fab fragments are generated by reducing the disulfide bridges of the $F(ab')_2$ fragments. The invention also provides heavy chain and light chain dimers of the antibodies of the invention, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of OGTA025, e.g., for imaging this protein, measuring levels thereof in appropriate physiological samples, in diagnostic methods, etc.

Production of Affibodies to OGTA025

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261: 199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to OGTA025

References to antibodies herein embrace references to Domain Antibodies. Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to OGTA025

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells.

Production of Unibodies to OGTA025

UniBody is a new proprietary antibody technology that creates a stable, smaller antibody format with an anticipated longer therapeutic window than current small antibody formats. IgG4 antibodies are considered inert and thus do not interact with the immune system. Genmab modified fully human IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to disease targets and the UniBody therefore binds univalently to only one site on target cells. This univalent binding does not stimulate cancer cells to grow like bivalent antibodies might and opens the door for treatment of some types of cancer which ordinary antibodies cannot treat.

The UniBody is about half the size of a regular IgG4 antibody. This small size can be a great benefit when treating some forms of cancer, allowing for better distribution of the molecule over larger solid tumors and potentially increasing efficacy.

Fabs typically do not have a very long half-life. UniBodies, however, were cleared at a similar rate to whole IgG4 antibodies and were able to bind as well as whole antibodies and antibody fragments in pre-clinical studies. Other antibodies primarily work by killing the targeted cells whereas UniBodies only inhibit or silence the cells.

Further details of Unibodies may be obtained by reference to patent WO2007/059782, which is herein incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g., PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCT based methods, etc.

In addition, techniques developed for the production of "chimeric antibodies" (Morrison et al., 1984, Proc. Natl. Acad. Sci. 81:851-855; Neuberger et al., 1984, *Nature* 312:604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, 2nd Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, *Gene* 45:101; Cockett et al., 1990, *Bio/Technology* 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) may be utilized.

As discussed above, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. OGTA025) as immunogen. Humanisation typically involves grafting CDRs identified thereby into human framework regions. Normally some subsequent retromutation to optimize the conformation of chains is required. Such processes are known to persons skilled in the art.

Expression of Affibodies

The construction of affibodies has been described elsewhere (Ronnmark J, Gronlund H, Uhlé n, M., Nygren P. A°, Human immunoglobulin A (IgA)-specific ligands from combinatorial engineering of protein A, 2002, Eur. J. Biochem. 269, 2647-2655.), including the construction of affibody phage display libraries (Nord, K., Nilsson, J., Nilsson, B., Uhlé n, M. & Nygren, P. A°, A combinatorial library of an α-helical bacterial receptor domain, 1995, *Protein Eng.* 8, 601-608. Nord, K., Gunneriusson, E., Ringdahl, J., Sta° hl, S., Uhlé n, M. & Nygren, P. A°, Binding proteins selected from combinatorial libraries of an α-helical bacterial receptor domain, 1997, Nat. Biotechnol. 15, 772-777.)

The biosensor analyses to investigate the optimal affibody variants using biosensor binding studies has also been described elsewhere (Ronnmark J, Gronlund H, Uhleˆ n, M., Nygren P. A°, Human immunoglobulin A (IgA)-specific ligands from combinatorial engineering of protein A, 2002, *Eur. J. Biochem.* 269, 2647-2655.).

Conjugated Affinity Reagents

In a preferred embodiment, anti-OGTA025 affinity reagents such as antibodies or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$. $^{68}Ga$ may also be employed.

Anti-OGTA025 antibodies or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2$^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

Diagnosis of HCC, Glioblastoma and Lung Cancer

In accordance with the present invention, test samples of liver, glioblastoma or lung tissue, serum, plasma or urine obtained from a subject suspected of having or known to have HCC, glioblastoma or lung cancer can be used for diagnosis or monitoring. In one embodiment, a change in the abundance of OGTA025 in a test sample relative to a control sample (from a subject or subjects free from HCC, glioblastoma and lung cancer) or a previously determined reference range indicates the presence of HCC, glioblastoma or lung cancer. In another embodiment, the relative abundance of OGTA025 in a test sample compared to a control sample or a previously determined reference range indicates a subtype of HCC, glioblastoma or lung cancer (e.g. fibrolamellar HCC or squamous cell lung carcinoma). In yet another embodiment, the relative abundance of OGTA025 in a test sample relative to a control sample or a previously determined reference range indicates the degree or severity of HCC, glioblastoma or lung cancer (e.g. the likelihood for metastasis). In any of the aforesaid methods, detection of OGTA025 may optionally be combined with detection of one or more of additional biomarkers for HCC, glioblastoma or lung cancer. Any suitable method in the art can be employed to measure the level of OGTA025, including but not limited to the Preferred Technology described herein, kinase assays, immunoassays to detect and/or visualize OGTA025 (e.g., Western blot, immunoprecipitation followed by sodium dodecyl sulfate polyacrylamide gel electrophoresis, immunocytochemistry, etc.). In a further embodiment, a change in the abundance of mRNA encoding OGTA025 in a test sample relative to a control sample or a previously determined reference range indicates the presence of HCC, glioblastoma or lung cancer. Any suitable hybridization assay can be used to detect OGTA025 expression by detecting and/or visualizing mRNA encoding the OGTA025 (e.g., Northern assays, dot blots, in situ hybridization, etc.).

In another embodiment of the invention, labeled antibodies (or other affinity reagents such as Affibodies, Nanobodies or Unibodies), derivatives and analogs thereof, which specifically bind to OGTA025 can be used for diagnostic purposes to detect, diagnose, or monitor HCC, glioblastoma and lung cancer. Preferably, HCC, glioblastoma or lung cancer is detected in an animal, more preferably in a mammal and most preferably in a human.

Screening Assays

The invention provides methods for identifying agents (e.g., candidate compounds or test compounds) that bind to OGTA025 or have a stimulatory or inhibitory effect on the expression or activity of OGTA025. The invention also provides methods of identifying agents, candidate compounds or test compounds that bind to an OGTA025-related polypeptide or an OGTA025 fusion protein or have a stimulatory or inhibitory effect on the expression or activity of an OGTA025-related polypeptide or an OGTA025 fusion protein. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-

6382; and Felici, 1991, J. Mol. Biol. 222:301-310), each of which is incorporated herein in its entirety by reference.

In one embodiment, agents that interact with (i.e., bind to) OGTA025, an OGTA025 fragment (e.g. a functionally active fragment), an OGTA025-related polypeptide, a fragment of an OGTA025-related polypeptide, or an OGTA025 fusion protein are identified in a cell-based assay system. In accordance with this embodiment, cells expressing OGTA025, a fragment of an OGTA025, an OGTA025-related polypeptide, a fragment of the OGTA025-related polypeptide, or an OGTA025 fusion protein are contacted with a candidate compound or a control compound and the ability of the candidate compound to interact with the OGTA025 is determined. If desired, this assay may be used to screen a plurality (e.g. a library) of candidate compounds. The cell, for example, can be of prokaryotic origin (e.g., *E. coli*) or eukaryotic origin (e.g., yeast or mammalian). Further, the cells can express OGTA025, a fragment of OGTA025, an OGTA025-related polypeptide, a fragment of the OGTA025-related polypeptide, or an OGTA025 fusion protein endogenously or be genetically engineered to express OGTA025, a fragment of OGTA025, an OGTA025-related polypeptide, a fragment of the OGTA025-related polypeptide, or an OGTA025 fusion protein. In certain instances, OGTA025, a fragment of OGTA025, an OGTA025-related polypeptide, a fragment of the OGTA025-related polypeptide, or an OGTA025 fusion protein or the candidate compound is labeled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between OGTA025 and a candidate compound. The ability of the candidate compound to interact directly or indirectly with OGTA025, a fragment of OGTA025, an OGTA025-related polypeptide, a fragment of an OGTA025-related polypeptide, or an OGTA025 fusion protein can be determined by methods known to those of skill in the art. For example, the interaction between a candidate compound and OGTA025, an OGTA025-related polypeptide, a fragment of an OGTA025-related polypeptide, or an OGTA025 fusion protein can be determined by flow cytometry, a scintillation assay, immunoprecipitation or western blot analysis.

In another embodiment, agents that interact with (i.e., bind to) OGTA025, an OGTA025 fragment (e.g., a functionally active fragment), an OGTA025-related polypeptide, a fragment of an OGTA025-related polypeptide, or an OGTA025 fusion protein are identified in a cell-free assay system. In accordance with this embodiment, a native or recombinant OGTA025 or fragment thereof, or a native or recombinant OGTA025-related polypeptide or fragment thereof, or an OGTA025-fusion protein or fragment thereof, is contacted with a candidate compound or a control compound and the ability of the candidate compound to interact with OGTA025 or the OGTA025-related polypeptide, or the OGTA025 fusion protein is determined. If desired, this assay may be used to screen a plurality (e.g. a library) of candidate compounds. Preferably, OGTA025, an OGTA025 fragment, an OGTA025-related polypeptide, a fragment of an OGTA025-related polypeptide, or an OGTA025-fusion protein is first immobilized, by, for example, contacting OGTA025, an OGTA025 fragment, an OGTA025-related polypeptide, a fragment of an OGTA025-related polypeptide, or an OGTA025 fusion protein with an immobilized antibody (or other affinity reagent such as an Affibody, Nanobody or Unibody) which specifically recognizes and binds it, or by contacting a purified preparation of OGTA025, an OGTA025 fragment, an OGTA025-related polypeptide, a fragment of an OGTA025-related polypeptide, or an OGTA025 fusion protein with a surface designed to bind proteins. OGTA025, an OGTA025 fragment, an OGTA025-related polypeptide, a fragment of an OGTA025-related polypeptide, or an OGTA025 fusion protein may be partially or completely purified (e.g., partially or completely free of other polypeptides) or part of a cell lysate. Further, OGTA025, an OGTA025 fragment, an OGTA025-related polypeptide, a fragment of an OGTA025-related polypeptide may be a fusion protein comprising OGTA025 or a biologically active portion thereof, or OGTA025-related polypeptide and a domain such as glutathionine-S-transferase. Alternatively, OGTA025, an OGTA025 fragment, an OGTA025-related polypeptide, a fragment of an OGTA025-related polypeptide or an OGTA025 fusion protein can be biotinylated using techniques well known to those of skill in the art (e.g., biotinylation kit, Pierce Chemicals; Rockford, Ill.). The ability of the candidate compound to interact with OGTA025, an OGTA025 fragment, an OGTA025-related polypeptide, a fragment of an OGTA025-related polypeptide, or an OGTA025 fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of OGTA025 or is responsible for the post-translational modification of OGTA025. In a primary screen, a plurality (e.g., a library) of compounds are contacted with cells that naturally or recombinantly express: (i) OGTA025, an isoform of OGTA025, an OGTA025 homolog, an OGTA025-related polypeptide, an OGTA025 fusion protein, or a biologically active fragment of any of the foregoing; and (ii) a protein that is responsible for processing of OGTA025, the OGTA025 isoform, the OGTA025 homolog, the OGTA025-related polypeptide, the OGTA025 fusion protein, or fragment in order to identify compounds that modulate the production, degradation, or post-translational modification of OGTA025, the OGTA025 isoform, the OGTA025 homolog, the OGTA025-related polypeptide, the OGTA025 fusion protein or fragment. If desired, compounds identified in the primary screen can then be assayed in a secondary screen against cells naturally or recombinantly expressing OGTA025. The ability of the candidate compound to modulate the production, degradation or post-translational modification of OGTA025, isoform, homolog, OGTA025-related polypeptide, or OGTA025 fusion protein can be determined by methods known to those of skill in the art, including without limitation, flow cytometry, a scintillation assay, immunoprecipitation and western blot analysis.

In another embodiment, agents that competitively interact with (i.e., bind to) OGTA025, an OGTA025 fragment, an OGTA025-related polypeptide, a fragment of an OGTA025-related polypeptide, or an OGTA025 fusion protein are identified in a competitive binding assay. In accordance with this embodiment, cells expressing OGTA025, an OGTA025 fragment, an OGTA025-related polypeptide, a fragment of an OGTA025-related polypeptide, or an OGTA025 fusion protein are contacted with a candidate compound and a compound known to interact with OGTA025, an OGTA025 fragment, an OGTA025-related polypeptide, a fragment of an OGTA025-related polypeptide or an OGTA025 fusion protein; the ability of the candidate compound to preferentially interact with OGTA025, an OGTA025 fragment, an OGTA025-related polypeptide, a fragment of an OGTA025-related polypeptide, or an OGTA025 fusion protein is then determined. Alternatively, agents that preferentially interact with (i.e., bind to) OGTA025, an OGTA025 fragment, an OGTA025-related polypeptide or fragment of an OGTA025-related polypeptide are identified in a cell-free assay system by contacting OGTA025, an OGTA025 fragment, an OGTA025-related polypeptide, a fragment of an OGTA025-related polypeptide, or an OGTA025 fusion protein with a candidate compound and a compound known to interact with OGTA025, the OGTA025-related polypeptide or the OGTA025 fusion protein. As stated above, the ability of the candidate compound to interact with OGTA025, an OGTA025 fragment, an OGTA025-related polypeptide, a fragment of an OGTA025-related polypeptide, or an OGTA025 fusion protein can be determined by methods known to those of skill in the art. These assays, whether cell-based or cell-free, can be used to screen a plurality (e.g., a library) of candidate compounds.

In another embodiment, agents that modulate (i.e., upregulate or downregulate) the expression or activity of OGTA025, or an OGTA025-related polypeptide are identified by contacting cells (e.g., cells of prokaryotic origin or eukaryotic origin) expressing OGTA025, or the OGTA025-related polypeptide with a candidate compound or a control compound (e.g., phosphate buffered saline (PBS)) and determining the expression of OGTA025, the OGTA025-related polypeptide, or the OGTA025 fusion protein, mRNA encoding OGTA025, or mRNA encoding the OGTA025-related polypeptide. The level of expression of OGTA025, the OGTA025-related polypeptide, mRNA encoding OGTA025, or mRNA encoding the OGTA025-related polypeptide in the presence of the candidate compound is compared to the level of expression of OGTA025, the OGTA025-related polypeptide, mRNA encoding OGTA025, or mRNA encoding the OGTA025-related polypeptide in the absence of the candidate compound (e.g., in the presence of a control compound). The candidate compound can then be identified as a modulator of the expression of OGTA025, or the OGTA025-related polypeptide based on this comparison. For example, when expression of OGTA025 or mRNA is significantly greater in the presence of the candidate compound than in its absence, the candidate compound is identified as a stimulator of expression of OGTA025 or mRNA. Alternatively, when expression of OGTA025 or mRNA is significantly less in the presence of the candidate compound than in its absence, the candidate compound is identified as an inhibitor of the expression of OGTA025 or mRNA. The level of expression of OGTA025 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of OGTA025 or an OGTA025-related polypeptide are identified by contacting a preparation containing OGTA025 or the OGTA025-related polypeptide or cells (e.g., prokaryotic or eukaryotic cells) expressing OGTA025 or the OGTA025-related polypeptide with a test compound or a control compound and determining the ability of the test compound to modulate (e.g., stimulate or inhibit) the activity of OGTA025 or the OGTA025-related polypeptide. The activity of OGTA025 or an OGTA025-related polypeptide can be assessed by detecting induction of a cellular signal transduction pathway of OGTA025 or the OGTA025-related polypeptide (e.g., intracellular $Ca^{2+}$, diacylglycerol, IP3, etc.), detecting catalytic or enzymatic activity of the target on a suitable substrate, detecting the induction of a reporter gene (e.g., a regulatory element that is responsive to OGTA025 or an OGTA025-related polypeptide and is operably linked to a nucleic acid encoding a detectable marker, e.g., luciferase), or detecting a cellular response, for example, cellular differentiation, or cell proliferation. Based on the present description, techniques known to those of skill in the art can be used for measuring these activities (see, e.g., U.S. Pat. No. 5,401,639, which is incorporated herein by reference). The candidate compound can then be identified as a modulator of the activity of OGTA025 or an OGTA025-related polypeptide by comparing the effects of the candidate compound to the control compound. Suitable control compounds include phosphate buffered saline (PBS) and normal saline (NS).

In another embodiment, agents that modulate (i.e., upregulate or downregulate) the expression, activity or both the expression and activity of OGTA025 or an OGTA025-related polypeptide are identified in an animal model. Examples of suitable animals include, but are not limited to, mice, rats, rabbits, monkeys, guinea pigs, dogs and cats. Preferably, the animal used represent a model of HCC, glioblastoma or lung cancer (e.g. xenografts of HCC cell lines such as MHCC97 in nude mice, Tian et al., Br J Cancer 1999 November; 81(5):814-21; xenografts of glioblastoma cell lines such as U87MG in nude mice, Abernathey et al., Neurosurgery 1988 May; 22(5):877-81 or xenografts of non small cell lung cancer cell lines such as A549 and H460 and xenografts of small cell lung cancer cell lines such as NCI-H345 or NCI-H69). These can be utilized to test compounds that modulate OGTA025 levels, since the pathology exhibited in these models is similar to that of HCC, glioblastoma and lung cancer. In accordance with this embodiment, the test compound or a control compound is administered (e.g., orally, rectally or parenterally such as intraperitoneally or intravenously) to a suitable animal and the effect on the expression, activity or both expression and activity of OGTA025 or OGTA025-related polypeptide is determined. Changes in the expression of OGTA025 or an OGTA025-related polypeptide can be assessed by the methods outlined above.

In yet another embodiment, OGTA025 or an OGTA025-related polypeptide is used as a "bait protein" in a two-hybrid assay or three hybrid assay to identify other proteins that bind to or interact with OGTA025 or an OGTA025-related polypeptide (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by OGTA025 as, for example, upstream or downstream elements of a signaling pathway involving OGTA025.

This invention further provides novel agents identified by the above-described screening assays and uses thereof for treatments as described herein. In addition, the invention also provides the use of an agent which interacts with, or modulates the activity of, OGTA025 in the manufacture of a medicament for the treatment of HCC, glioblastoma or lung cancer.

Therapeutic Use of OGTA025

The invention provides for treatment or prevention of various diseases and disorders by administration of a therapeutic compound. Such compounds include but are not limited to: OGTA025, OGTA025 analogs, OGTA025-related polypeptides and derivatives (including fragments) thereof; antibodies (or other affinity reagents such as Affibodies, Nanobodies or Unibodies) to the foregoing; nucleic acids encoding OGTA025, OGTA025 analogs, OGTA025-related polypeptides and fragments thereof; antisense nucleic acids to a gene encoding OGTA025 or an OGTA025-related polypeptide; and modulator (e.g., agonists and antagonists) of a gene encoding OGTA025 or an OGTA025-related polypeptide. An important feature of the present invention is the identification of genes encoding OGTA025 involved in HCC, glioblastoma or lung cancer. HCC, glioblastoma or lung cancer can be treated (e.g. to ameliorate symptoms or to retard onset or progression) or prevented by administration of a therapeutic compound that reduces function or expression of OGTA025 in the serum or tissue of subjects having HCC, glioblastoma or lung cancer.

In one embodiment, one or more antibodies (or other affinity reagents such as Affibodies, Nanobodies or Unibodies) each specifically binding to OGTA025 are administered alone or in combination with one or more additional therapeutic compounds or treatments.

Preferably, a biological product such as an antibody (or other affinity reagent such as an Affibody, Nanobody or Unibody) is allogeneic to the subject to which it is administered. In a preferred embodiment, a human OGTA025 or a human OGTA025-related polypeptide, a nucleotide sequence encoding a human OGTA025 or a human OGTA025-related polypeptide, or an antibody (or other affinity reagent such as an Affibody, Nanobody or Unibody) to a human OGTA025 or a human OGTA025-related polypeptide, is administered to a human subject for therapy (e.g. to ameliorate symptoms or to retard onset or progression) or prophylaxis.

Without being limited by theory, it is conceived that the therapeutic activity of antibodies (or other affinity reagents such as Affibodies, Nanobodies or Unibodies) which specifically bind to OGTA025 may be achieved through the phenomenon of Antibody-Dependent Cell-mediated Cytotoxicity (ADCC) (see e.g. Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532:p 2153-68 and Weng, W.-K. et al., Journal of Clinical Oncology, 2003, 21:p 3940-3947).

Treatment and Prevention of HCC, Glioblastoma and Lung Cancer

HCC, glioblastoma or lung cancer is treated or prevented by administration to a subject suspected of having or known to have HCC, glioblastoma or lung cancer or to be at risk of developing HCC, glioblastoma or lung cancer of a compound that modulates (i.e., increases or decreases) the level or activity (i.e., function) of OGTA025 that is differentially present in the serum or tissue of subjects having HCC, glioblastoma or lung cancer compared with serum or tissue of subjects free from HCC, glioblastoma and lung cancer. In one embodiment, HCC, glioblastoma or lung cancer is treated or prevented by administering to a subject suspected of having or known to have HCC, glioblastoma or lung cancer or to be at risk of developing HCC, glioblastoma or lung cancer a compound that upregulates (i.e., increases) the level or activity (i.e., function) of OGTA025 that are decreased in the serum or tissue of subjects having HCC, glioblastoma or lung cancer. Examples of such a compound include, but are not limited to, OGTA025 antisense oligonucleotides, ribozymes, antibodies (or other affinity reagents such as Affibodies, Nanobodies or Unibodies) directed against OGTA025, and compounds that inhibit the enzymatic activity of OGTA025. Other useful compounds e.g., OGTA025 antagonists and small molecule OGTA025 antagonists, can be identified using in vitro assays.

HCC, glioblastoma or lung cancer is also treated or prevented by administration to a subject suspected of having or known to have HCC, glioblastoma or lung cancer or to be at risk of developing HCC, glioblastoma or lung cancer of a compound that downregulates the level or activity (i.e. function) of OGTA025 that are increased in the serum or tissue of subjects having HCC, glioblastoma or lung cancer. Examples of such a compound include but are not limited to: OGTA025, OGTA025 fragments and OGTA025-related polypeptides; nucleic acids encoding OGTA025, an OGTA025 fragment and an OGTA025-related polypeptide (e.g., for use in gene therapy); and, for those OGTA025 or OGTA025-related polypeptides with enzymatic activity, compounds or molecules known to modulate that enzymatic activity. Other compounds that can be used, e.g., OGTA025 agonists, can be identified using in in vitro assays.

In a preferred embodiment, therapy or prophylaxis is tailored to the needs of an individual subject. Thus, in specific embodiments, compounds that promote the level or function of OGTA025 are therapeutically or prophylactically administered to a subject suspected of having or known to have HCC, glioblastoma or lung cancer, in whom the levels or functions of OGTA025 are absent or are decreased relative to a control or normal reference range. In further embodiments, compounds that promote the level or function of OGTA025 are therapeutically or prophylactically administered to a subject suspected of having or known to have HCC, glioblastoma or lung cancer in whom the levels or functions of OGTA025 are increased relative to a control or to a reference range. In further embodiments, compounds that decrease the level or function of OGTA025 are therapeutically or prophylactically administered to a subject suspected of having or known to have HCC, glioblastoma or lung cancer in whom the levels or functions of OGTA025 are increased relative to a control or to a reference range. In further embodiments, compounds that decrease the level or function of OGTA025 are therapeutically or prophylactically administered to a subject suspected of having or known to have HCC, glioblastoma or lung cancer in whom the levels or functions of OGTA025 are decreased relative to a control or to a reference range. The change in OGTA025 function or level due to the administration of such compounds can be readily detected, e.g., by obtaining a sample (e.g., blood or urine) and assaying in vitro the levels or activities of OGTA025, or the levels of mRNAs encoding OGTA025, or any combination of the foregoing. Such assays can be performed before and after the administration of the compound as described herein.

The compounds of the invention include but are not limited to any compound, e.g., a small organic molecule, protein, peptide, antibody (or other affinity reagent such as an Affibody, Nanobody or Unibody), nucleic acid, etc. that restores the OGTA025 profile towards normal. The compounds of the invention may be given in combination with any other chemotherapy drugs.

Vaccine Therapy

OGTA025 may be useful as antigenic material, and may be used in the production of vaccines for treatment or prophylaxis of HCC, glioblastoma and lung cancer. Such material can be “antigenic” and/or “immunogenic”. Generally, “antigenic” is taken to mean that the protein is capable of being used to raise antibodies (or other affinity reagents such as Affibodies, Nanobodies or Unibodies) or indeed is capable of inducing an antibody response in a subject or experimental animal. “Immunogenic” is taken to mean that the protein is capable of eliciting a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting eg a T-cell proliferation assay.

The skilled person will appreciate that homologues or derivatives of OGTA025 will also find use as antigenic/immunogenic material. Thus, for instance proteins which include one or more additions, deletions, substitutions or the like are encompassed by the present invention. In addition, it may be possible to replace one amino acid with another of similar "type", for instance, by replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided. Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of OGTA025, or of homologues or derivatives thereof.

OGTA025, or antigenic fragments thereof, can be provided alone, as a purified or isolated preparation. They may be provided as part of a mixture with one or more other proteins, or antigenic fragments thereof. In a further aspect, therefore, the invention provides an antigen composition comprising OGTA025 and/or one or more antigenic fragments thereof. Such a composition can be used for the detection and/or diagnosis of HCC, glioblastoma or lung cancer.

In a sixth aspect, the present invention provides a method of detecting and/or diagnosing HCC, glioblastoma or lung cancer which comprises:

bringing into contact with a sample to be tested an antigenic OGTA025, or an antigenic fragment thereof, or an antigen composition of the invention; and detecting the presence of antibodies (or other affinity reagents such as Affibodies, Nanobodies or Unibodies) to HCC, glioblastoma or lung cancer.

In particular, the protein, antigenic fragment thereof or antigen composition of the present invention can be used to detect IgA, IgM or IgG antibodies. Suitably, the sample to be tested will be a biological sample, e.g. a sample of blood or saliva.

In a further aspect, the invention provides the use of an antigenic OGTA025, antigenic fragment thereof or an antigenic composition of the present invention in detecting and/or diagnosing HCC, glioblastoma or lung cancer. Preferably, the detecting and/or diagnosing are carried out in vitro.

The antigenic OGTA025, antigenic fragments thereof or antigenic composition of the present invention can be provided as a kit for use in the in vitro detection and/or diagnosis of HCC, glioblastoma or lung cancer. Thus, in a still further aspect, the present invention provides a kit for use in the detection and/or diagnosis of HCC, glioblastoma or lung cancer, which kit comprises an antigenic OGTA025, an antigenic fragment thereof or an antigenic composition of the present invention.

In addition, the antigenic OGTA025, antigenic fragment thereof or antigen composition of the invention can be used to induce an immune response against HCC, glioblastoma or lung cancer. Thus, in a yet further aspect, the invention provides the use of an antigenic OGTA025, an antigenic fragment thereof or an antigen composition of the invention in medicine.

In a further aspect, the present invention provides a composition capable of eliciting an immune response in a subject, which composition comprises OGTA025, an antigenic fragment thereof, or an antigen composition of the invention. Suitably, the composition will be a vaccine composition, optionally comprising one or more suitable adjuvants. Such a vaccine composition may be either a prophylactic or therapeutic vaccine composition.

The vaccine compositions of the invention can include one or more adjuvants. Examples well-known in the art include inorganic gels, such as aluminium hydroxide, and water-in-oil emulsions, such as incomplete Freund's adjuvant. Other useful adjuvants will be well known to the skilled person.

In yet further aspects, the present invention provides:

(a) the use of OGTA025, an antigenic fragment thereof, or an antigen composition of the invention in the preparation of an immunogenic composition, preferably a vaccine;

(b) the use of such an immunogenic composition in inducing an immune response in a subject; and (c) a method for the treatment or prophylaxis of HCC, glioblastoma or lung cancer in a subject, or of vaccinating a subject against HCC, glioblastoma or lung cancer which comprises the step of administering to the subject an effective amount of OGTA025, at least one antigenic fragment thereof or an antigen composition of the invention, preferably as a vaccine.

In a specific embodiment, a preparation of OGTA025 or OGTA025 peptide fragments is used as a vaccine for the treatment of HCC, glioblastoma or lung cancer. Such preparations may include adjuvants or other vehicles.

In another embodiment, a preparation of oligonucleotides comprising 10 or more consecutive nucleotides complementary to a nucleotide sequence encoding OGTA025 or OGTA025 peptide fragments is used as vaccines for the treatment of HCC, glioblastoma or lung cancer. Such preparations may include adjuvants or other vehicles.

Inhibition of OGTA025 to Treat HCC, Glioblastoma and Lung Cancer

In one embodiment of the invention, HCC, glioblastoma or lung cancer is treated or prevented by administration of a compound that antagonizes (inhibits) the level(s) and/or function(s) of OGTA025 which are elevated in the serum or tissue of subjects having HCC, glioblastoma or lung cancer as compared with serum or tissue of subjects free from HCC, glioblastoma and lung cancer.

Compounds useful for this purpose include but are not limited to anti-OGTA025 antibodies (or other affinity reagents such as Affibodies, Nanobodies or Unibodies, and fragments and derivatives containing the binding region thereof), OGTA025 antisense or ribozyme nucleic acids, and nucleic acids encoding dysfunctional OGTA025 that are used to "knockout" endogenous OGTA025 function by homologous recombination (see, e.g., Capecchi, 1989, *Science* 244:1288-1292). Other compounds that inhibit OGTA025 function can be identified by use of known in vitro assays, e.g., assays for the ability of a test compound to inhibit binding of OGTA025 to another protein or a binding partner, or to inhibit a known OGTA025 function. Preferably such inhibition is assayed in vitro or in cell culture, but genetic assays may also be employed. The Preferred Technology can also be used to detect levels of OGTA025 before and after the administration of the compound. Preferably, suitable in vitro or in vivo assays are utilized to determine the effect of a specific compound and whether its administration is indicated for treatment of the affected tissue, as described in more detail below.

In a specific embodiment, a compound that inhibits OGTA025 function is administered therapeutically or prophylactically to a subject in whom an increased serum or tissue level or functional activity of OGTA025 (e.g., greater than the normal level or desired level) is detected as compared with serum or tissue of subjects free from HCC, glioblastoma and lung cancer or a predetermined reference range. Methods standard in the art can be employed to measure the increase in OGTA025 level or function, as outlined above. Preferred OGTA025 inhibitor compositions include small molecules, i.e., molecules of 1000 daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of HCC, glioblastoma and lung cancer. Test compounds can be assayed for their ability to restore OGTA025 levels in a subject having HCC, glioblastoma or lung cancer towards levels found in subjects free from HCC, glioblastoma and lung cancer or to produce similar changes in experimental animal models of HCC, glioblastoma or lung cancer. Compounds able to restore OGTA025 levels in a subject having HCC, glioblastoma or lung cancer towards levels found in subjects free from HCC, glioblastoma and lung cancer or to produce similar changes in experimental animal models of HCC, glioblastoma or lung cancer can be used as lead compounds for further drug discovery, or used therapeutically. OGTA025 expression can be assayed by the Preferred Technology, immunoassays, gel electrophoresis followed by visualization, detection of OGTA025 activity, or any other method taught herein or known to those skilled in the art. Such assays can be used to screen candidate drugs, in clinical monitoring or in drug development, where abundance of OGTA025 can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of HCC, glioblastoma and lung cancer include, but are not limited to xenografts of HCC cell lines such as MHCC97 in nude mice (Tian et al., Br J Cancer 1999 November; 81(5):814-21); xenografts of glioblastoma cell lines such as U87MG in nude mice (Abernathey et al., Neurosurgery 1988 May; 22(5):877-81) or xenografts of non small cell lung cancer cell lines such as A549 and H460 and xenografts of small cell lung cancer cell lines such as NCI-H345 or NCI-H69. These can be utilized to test compounds that modulate OGTA025 levels, since the pathology exhibited in these models is similar to that of HCC, glioblastoma and lung cancer. It is also apparent to the skilled artisan that based upon the present disclosure, transgenic animals can be produced with "knock-out" mutations of the gene or genes encoding OGTA025. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal; more preferably, the transgenic animal is a mouse.

In one embodiment, test compounds that modulate the expression of OGTA025 are identified in non-human animals (e.g., mice, rats, monkeys, rabbits, and guinea pigs), preferably non-human animal models for HCC, glioblastoma and lung cancer, expressing OGTA025. In accordance with this embodiment, a test compound or a control compound is administered to the animals, and the effect of the test compound on expression of OGTA025 is determined. A test compound that alters the expression of OGTA025 can be identified by comparing the level of OGTA025 (or mRNA encoding the same) in an animal or group of animals treated with a test compound with the level of the OGTA025 or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of OGTA025 or a biologically active portion thereof are identified in non-human animals (e.g., mice, rats, monkeys, rabbits, and guinea pigs), preferably non-human animal models for HCC, glioblastoma and lung cancer, expressing OGTA025. In accordance with this embodiment, a test compound or a control compound is administered to the animals, and the effect of a test compound on the activity of OGTA025 is determined. A test compound that alters the activity of OGTA025 can be identified by assaying animals treated with a control compound and animals treated with the test compound. The activity of OGTA025 can be assessed by detecting induction of a cellular second messenger of OGTA025 (e.g., intracellular $Ca^{2+}$, diacylglycerol, IP3, etc.), detecting catalytic or enzymatic activity of OGTA025 or binding partner thereof, detecting the induction of a reporter gene (e.g., a regulatory element that is responsive to OGTA025 operably linked to a nucleic acid encoding a detectable marker, such as luciferase or green fluorescent protein), or detecting a cellular response (e.g., cellular differentiation or cell proliferation). Techniques known to those of skill in the art can be utilized to detect changes in the activity of OGTA025 (see, e.g., U.S. Pat. No. 5,401,639, which is incorporated herein by reference).

In yet another embodiment, test compounds that modulate the level or expression of OGTA025 are identified in human subjects having HCC, glioblastoma or lung cancer, preferably those having severe HCC, glioblastoma or lung cancer. In accordance with this embodiment, a test compound or a control compound is administered to the human subject, and the effect of a test compound on OGTA025 expression is determined by analyzing the expression of OGTA025 or the mRNA encoding the same in a biological sample (e.g., serum, plasma, or urine). A test compound that alters the expression of OGTA025 can be identified by comparing the level of OGTA025 or mRNA encoding the same in a subject or group of subjects treated with a control compound to that in a subject or group of subjects treated with a test compound. Alternatively, alterations in the expression of OGTA025 can be identified by comparing the level of OGTA025 or mRNA encoding the same in a subject or group of subjects before and after the administration of a test compound. Techniques known to those of skill in the art can be used to obtain the biological sample and analyze the mRNA or protein expression. For example, the Preferred Technology described herein can be used to assess changes in the level of OGTA025.

In another embodiment, test compounds that modulate the activity of OGTA025 are identified in human subjects having HCC, glioblastoma or lung cancer, (preferably those with severe HCC, glioblastoma or lung cancer). In this embodiment, a test compound or a control compound is administered to the human subject, and the effect of a test compound on the activity of OGTA025 is determined. A test compound that alters the activity of OGTA025 can be identified by comparing biological samples from subjects treated with a control compound to samples from subjects treated with the test compound. Alternatively, alterations in the activity of OGTA025 can be identified by comparing the activity of OGTA025 in a subject or group of subjects before and after the administration of a test compound. The activity of OGTA025 can be assessed by detecting in a biological sample (e.g., serum, plasma, or urine) induction of a cellular signal transduction pathway of OGTA025 (e.g., intracellular $Ca^{2+}$, diacylglycerol, IP3, etc.), catalytic or enzymatic activity of OGTA025 or a binding partner thereof, or a cellular response, for example, cellular differentiation, or cell proliferation. Techniques known to those of skill in the art can be used to detect changes in the induction of a second messenger of OGTA025 or changes in a cellular response. For example, RT-PCR can be used to detect changes in the induction of a cellular second messenger.

In a preferred embodiment, a test compound that changes the level or expression of OGTA025 towards levels detected in control subjects (e.g., humans free from HCC, glioblastoma and lung cancer) is selected for further testing or therapeutic use. In another preferred embodiment, a test compound that changes the activity of OGTA025 towards the activity found in control subjects (e.g., humans free from HCC, glioblastoma and lung cancer) is selected for further testing or therapeutic use.

In another embodiment, test compounds that reduce the severity of one or more symptoms associated with HCC, glioblastoma or lung cancer are identified in human subjects having HCC, glioblastoma or lung cancer, preferably subjects with severe HCC, glioblastoma or lung cancer. In accordance with this embodiment, a test compound or a control compound is administered to the subjects, and the effect of a test compound on one or more symptoms of HCC, glioblastoma or lung cancer is determined. A test compound that reduces one or more symptoms can be identified by comparing the subjects treated with a control compound to the subjects treated with the test compound. Techniques known to physicians familiar with HCC, glioblastoma or lung cancer can be used to determine whether a test compound reduces one or more symptoms associated with HCC, glioblastoma or lung cancer. For example, a test compound that reduces tumour burden in a subject having HCC, glioblastoma or lung cancer will be beneficial for subjects having HCC, glioblastoma or lung cancer.

In a preferred embodiment, a test compound that reduces the severity of one or more symptoms associated with HCC, glioblastoma or lung cancer in a human having HCC, glioblastoma or lung cancer is selected for further testing or therapeutic use.

Therapeutic and Prophylactic Compositions and their Use

The invention provides methods of treatment (and prophylaxis) comprising administering to a subject an effective amount of a compound of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection;

intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection into liver, glioblastoma or lung tissue or at the site (or former site) of a malignant tumor or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the liver, brain or lung, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of HCC, glioblastoma or lung cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Determining Abundance of OGTA025 by Imaging Technology

An advantage of determining abundance of OGTA025 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of OGTA025 using such techniques requires incorporation or binding of a suitable label e.g. a radiotracer such as $^{18}F$, or $^{123}I$ (see e.g. NeuroRx—The Journal of the American Society for Experimental NeuroTherapeutics (2005) 2(2), 348-360 and idem pages 361-371 for further details of the techniques). Radiotracers or other labels may be incorporated into OGTA025 by administration to the subject (e.g. by injection) of a suitably labelled specific ligand. Alternatively they may be incorporated into a binding affinity reagent (antibody, Affibody, Nanobody, Unibody etc.) specific for OGTA025 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding affibody molecule, Cancer Res. 2006 Apr. 15; 66(8):4339-48).

Diagnosis and Treatment of HCC, Glioblastoma or Lung Cancer Using Immunohistochemistry Immunohistochemistry is an excellent detection technique and may therefore be very useful in the diagnosis and treatment of HCC, glioblastoma or lung cancer. Immunohistochemistry may be used to detect, diagnose, or monitor HCC, glioblastoma or lung cancer through the localization of OGTA025 antigens in tissue sections by the use of labeled antibodies (or other affinity reagents such as Affibodies, Nanobodies or Unibodies), derivatives and analogs thereof, which specifically bind to OGTA025, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

Preferred features of each aspect of the invention are as for each of the other aspects mutatis mutandis. The prior art documents mentioned herein are incorporated to the fullest extent permitted by law.

Example 1: Identification of Membrane Proteins Expressed in HCC and Glioblastoma Blood and Tissue Samples Using 1D Gel Electrophoresis Using the following Reference Protocol, membrane proteins extracted from HCC and glioblastoma tissue samples were separated by 1D gel and analysed.

1.1 Materials and Methods 1.1.1—Plasma Membrane Fractionation

The cells recovered from a glioblastoma or from the epithelium of a hepatocellular carcinoma were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was either run directly on 1D gels (see section 1.1.4 below), or further fractionated into heparin binding and nucleotide binding fractions as described below.

1.1.2—Plasma Membrane Heparin-Binding Fraction

The pooled solution from 1.1.1 above was applied to a Heparin column, eluted from column and run on 1D gels (see section 1.1.4 below).

1.1.3—Plasma Nucleotide-Binding Fraction

The pooled solution from 1.1.1 above was applied to a Cibacrom Blue 3GA column, eluted from column and run on 1D gels (see section 1.1.4 below).

1.1.4—1D Gel Technology

Protein or membrane pellets were solubilised in 1D sample buffer (1-2 μg/μl). The sample buffer and protein mixture was then heated to 95° C. for 3 min.

A 9-16% acrylamide gradient gel was cast with a stacking gel and a stacking comb according to the procedure described in Ausubel F. M. et al., eds., 1989, Current Protocols in Molecular Biology, Vol. II, Green Publishing Associates, Inc., and John Wiley & Sons, Inc., New York, section 10.2, incorporated herein by reference in its entirety.

30-50 micrograms of the protein mixtures obtained from detergent and the molecular weight standards (66, 45, 31, 21.14 kDa) were added to the stacking gel wells using a 10 microliter pipette tip and the samples run at 40 mA for 5 hours.

The plates were then prised open, the gel placed in a tray of fixer (10% acetic acid, 40% ethanol, 50% water) and shaken overnight. Following this, the gel was primed by 30 minutes shaking in a primer solution (7.5% acetic acid (75 ml), 0.05% SDS (5 ml of 10%)). The gel was then incubated with a fluorescent dye (7.5% acetic acid, 0.06% OGS in-house dye (600 μl)) with shaking for 3 hrs. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

A computer-readable output was produced by imaging the fluorescently stained gels with an Apollo 3 scanner (Oxford Glycosciences, Oxford, UK). This scanner is developed from the scanner described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. The latest embodiment of this instrument includes the following improvements: The gel is transported through the scanner on a precision lead-screw drive system. This is preferable to laying the glass plate on the belt-driven system that is defined in the Basiji thesis as it provides a reproducible means of accurately transporting the gel past the imaging optics.

The gel is secured into the scanner against three alignment stops that rigidly hold the glass plate in a known position. By doing this in conjunction with the above precision transport system and the fact that the gel is bound to the glass plate, the absolute position of the gel can be predicted and recorded. This ensures that accurate co-ordinates of each feature on the gel can be communicated to the cutting robot for excision. This cutting robot has an identical mounting arrangement for the glass plate to preserve the positional accuracy.

The carrier that holds the gel in place has integral fluorescent markers (Designated M1, M2, M3) that are used to correct the image geometry and are a quality control feature to confirm that the scanning has been performed correctly.

The optical components of the system have been inverted. The laser, mirror, waveguide and other optical components are now above the glass plate being scanned. The embodiment of the Basiji thesis has these underneath. The glass plate is therefore mounted onto the scanner gel side down, so that the optical path remains through the glass plate. By doing this, any particles of gel that may break away from the glass plate will fall onto the base of the instrument rather than into the optics.

In scanning the gels, they were removed from the stain, rinsed with water and allowed to air dry briefly and imaged on the Apollo 3. After imaging, the gels were sealed in polyethylene bags containing a small volume of staining solution, and then stored at 4° C.

Apparent molecular weights were calculated by interpolation from a set of known molecular weight markers run alongside the samples.

1.1.5—Recovery and Analysis of Selected Proteins

Proteins were robotically excised from the gels by the process described in U.S. Pat. No. 6,064,754, Sections 5.4 and 5.6, 5.7, 5.8 (incorporated herein by reference), as is applicable to 1D-electrophoresis, with modification to the robotic cutter as follows: the cutter begins at the top of the lane, and cuts a gel disc 1.7 mm in diameter from the left edge of the lane. The cutter then moves 2 mm to the right, and 0.7 mm down and cuts a further disc. This is then repeated. The cutter then moves back to a position directly underneath the first gel cut, but offset by 2.2 mm downwards, and the pattern of three diagonal cuts are repeated. This is continued for the whole length of the gel.

NOTE: If the lane is observed to broaden significantly then a correction can be made also sideways i.e. instead of returning to a position directly underneath a previous gel cut, the cut can be offset slightly to the left (on the left of the lane) and/or the right (on the right of the lane). The proteins contained within the gel fragments were processed to generate tryptic peptides; partial amino acid sequences of these peptides were determined by mass spectroscopy as described in WO98/53323 and application Ser. No. 09/094,996, filed Jun. 15, 1998.

Proteins were processed to generate tryptic digest peptides. Tryptic peptides were analyzed by mass spectrometry using a PerSeptive Biosystems Voyager-DETM STR Matrix-Assisted Laser Desorption Ionization Time-of-Flight (MALDI-TOF) mass spectrometer, and selected tryptic peptides were analyzed by tandem mass spectrometry (MS/MS) using a Micromass Quadrupole Time-of-Flight (Q-TOF) mass spectrometer (Micromass, Altrincham, U.K.) equipped with a Nanoflow™ electrospray Z-spray source. For partial amino acid sequencing and identification of OGTA025, uninterpreted tandem mass spectra of tryptic peptides were searched using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. The database searched was a database constructed of protein entries in the non-redundant database held by the National Centre for Biotechnology Information (NCBI). Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, Rapid Commun. Mass Spectrom. 6:658-662).

1.1.6—Discrimination of HCC and Glioblastoma Associated Proteins

The process to identify OGTA025 uses the peptide sequences obtained experimentally by mass spectrometry described above of naturally occurring human proteins to identify and organize coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001). Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a 'gene' is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to Form OGAP® Database Discrete genetic units (exons, transcripts and genes) were identified using the following sequential steps:

1. A 'virtual transcriptome' is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.
2. All tandem spectra in the OGeS Mass Spectrometry Database are interpreted in order to produce a peptide that can be mapped to one in the virtual transcriptome. A set of automated spectral interpretation algorithms were used to produce the peptide identifications.
3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.
4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.
5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome. Various elimination rules, based on cluster observation scoring and multiple mapping to the genome are used to refine the output. The resulting 'confirmed genes' are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display and search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 57 diseases including 506 genes in Bladder cancer, 4,713 genes in Breast cancer, 766 genes in Burkitt's lymphoma, 1,371 genes in Cervical cancer, 949 genes in Colorectal cancer, 1,544 genes in Glioblastoma, 1,782 genes in Hepatocellular carcinoma, 2,424 genes in CLL, 978 genes in Lung cancer, 1,764 genes in Melanoma, 1,033 genes in Ovarian Cancer, 2,961 genes in Pancreatic cancer and 3,307 genes in Prostate cancer, illustrated here by OGTA025 isolated and identified from HCC and glioblastoma samples. Following comparison of the experimentally determined sequences with sequences in the OGAP® database, OGTA025 showed a high degree of specificity to HCC and glioblastoma indicative of the prognostic and diagnostic nature.

1.2 Results

These experiments identified OGTA025, in its two different isoforms, as further described herein. The full-length OGTA025 was detected in the plasma membrane of HCC and glioblastoma samples and was not detected in the cytosol.

FIG. 2 shows the Protein Index for OGTA025. For each gene, the protein index uses the mass spectrometry data to assign a score to each disease, relative to the global database. The Protein Index can then be used to identify cancer specific genes with a high score in cancer indications and low/negligible scores in normal and other diseases. The index contains ~1 million peptides sequenced via mass spectrometry from 56 diseases. For each gene, this yields a score for each disease and subcellular location. The results are summarized below:

Protein Index Report for OGTA025

Indications Positive:

Hepatocellular carcinoma

Glioblastoma

Prostate cancer

Disease Controls

| |
|---|
| Acute monocytic leukaemia |
| Acute T-cell leukaemia |
| Alzheimer's Disease |
| Arthritis |
| Asthma |
| Atherosclerosis |
| B-cell non-Hodgkin's lymphoma |
| Bladder carcinoma |
| Breast cancer |
| Breast diseases, benign |
| Burkitt's lymphoma |
| Bursitis |
| Cancer, unspecified |
| Cervical cancer |
| Chronic lymphocytic leukaemia |
| Chronic obstructive pulmonary disease |
| Colorectal cancer |
| Dementia, vascular |
| Depression |
| Diabetes and Obesity |
| Diverticulitis |
| Dyslipidaemia |
| Emphysema |
| Focal apocrine metaplasia |
| Gastric cancer |
| Gaucher disease |
| Glioblastoma |
| Hepatoblastoma |
| Hepatocellular carcinoma |
| Hypertension |
| Lactational foci |
| Leukaemia, unspecified |
| Liver cirrhosis |
| Lung cancer |
| Lymphoma, histiocytic |
| Melanoma |

-continued

| |
|---|
| Metabolic syndrome X |
| Migraine, acute |
| Multiple sclerosis |
| Neuroblastoma |
| Normal |
| Obesity |
| Osteoarthritis |
| Osteosarcoma |
| Ovarian cancer |
| Pancreatic cancer |
| Prostate cancer |
| Prostatic diseases, benign |
| Prostatitis |
| Renal cell cancer |
| Retinoblastoma |
| Schizophrenia |
| Skin ulcer |
| Smoker |
| Teratocarcinoma |

Subcellular Location

| |
|---|
| Birbeck Granules |
| Cell surface digest |
| Cerebral Cortex Membrane |
| Cerebral Meninges Membrane |
| Chromatin Fraction |
| Crude Cell Membrane |
| Cytosol |
| Golgi/Mitochondrial |
| Hippocampus Membrane |
| Membrane |
| Membrane Glycoprotein Binding Fraction |
| Mitochondria |
| Nucleus |
| Peripheral Nervous Membrane |
| Peroxisomes |
| Pituitary Membrane |
| Plasma Membrane |
| Secreted |
| Soluble Fraction |
| Supernatant |
| Whole Cell |

FIG. 2 shows the Protein Index for OGTA025 is high in hepatocellular carcinoma plasma membrane and medium in glioblastoma plasma membrane. It was also detected as low in normal cerebral cortex membrane, low in normal cerebral meninges membrane, low in normal hippocampus membrane, low in normal peripheral nervous membrane, low in normal pituitary membrane and low in prostate cancer supernatant. OGTA025 was not detected in any other diseases. This indicates that OGTA025 is potentially a good marker for hepatocellular carcinoma and glioblastoma.

Example 2: Identification of Membrane Proteins Expressed in Lung Cancer Blood and Tissue Samples Using Isotope Tagging for Absolute and Relative Quantitation (iTRAQ)

Using the following Reference Protocol, membrane proteins extracted from lung cancer tissue and normal adjacent lung tissue samples were digested, labelled with Isotope Tagging for Absolute & Relative Quantitation reagents (iTRAQ; Applied Biosystems, Foster City, Calif., USA) and resulting peptides sequenced by tandem mass spectrometry.

2.1 Materials and Methods 2.1.1—Plasma Membrane Fractionation

The cells recovered from a lung cancer or normal adjacent tissue were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was then analysed directly by iTRAQ (see section 2.1.2 below).

2.1.2—iTRAQ Methodology

Membrane protein pellets from colorectal cancer and normal adjacent tissue were solubilised in sample buffer (2-4 μg/μl in 0.5% SDS) by the addition of buffer and then heating to 95° C. for 3 min.

To a volume of each protein solution equating to 50 μg, 150 μl of 0.5M triethylammonium bicarbonate (TEAB) solution was added. To each sample, 3 μl of 50 mM tris-(2-carboxyethyl)phosphine was added and the mixture was incubated at 60° C. for 1 hour. 1 μl of cysteine blocking reagent, 200 mM methyl methanethiosulphonate (MMTS) in isopropanol, was then added. After incubation at room temperature for 10 minutes, 15 μl of 1 μg/μl trypsin was added to each sample followed by incubation at 37° C. overnight.

The digested samples were dried under a vacuum and re-constituted with 30 μl of 0.5M TEAB solution. 70 μl ethanol was added to each of the four iTRAQ reagents (114/115/116/117) and one reagent added to each of the four samples analysed (two lung cancer samples and two corresponding normal adjacent tissue samples) and left at room temperature for 1 hour. The specific reagent added to each sample was recorded. The four labeled samples were combined & vortexed.

The combined sample was reduced to dryness under a vacuum and de-salted by loading onto a C18 spin column, washing with aqueous solvent and then eluting with 70% acetontrile. The sample fraction was again reduced to dryness and then re-dissolved in 40 μl of solvent A (97.9 water, 2% acetonitrile, 0.1% formic acid) prior to ion exchange fractionation.

2.1.3—Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 μl m; 50×0.8 mm) using a 20 μl/min gradient of 0-100 mM sodium acetate over 20 minutes and then to 1M over 10 minutes. 1 minute fractions were collected over the 30 minute run.

Each fraction was analysed by liquid chromatography/mass spectrometry using an Agilent 1200 chromatograph fitted with a Zorbax 300SB-C18 (150 mm×75 μl m) and an Agilent 6510 quadrupole-time-of-flight instrument (Agilent, Santa Clara, Calif., USA). Peptides were eluted with a 300 nl/min gradient increasing from 15% to 45% acetonitrile in 60 minutes. Data was acquired in auto MS/MS mode such that up to 3 precursor ions above the intensity threshold were selected and product ion spectra accumulated to facilitate the sequencing of the labeled peptides. Raw data was processed to create peak lists using Spectrum Mill software (Agilent, Santa Clara, Calif., USA).

2.1.4—Amino Acid Sequence Analysis of Labeled Peptides

For partial amino acid sequencing and identification of OGTA025, uninterpreted tandem mass spectra of tryptic peptides were searched using the SEQUEST search program (Eng et al., 1994, J. Am. Soc. Mass Spectrom. 5:976-989). Criteria for database identification included: the cleavage specificity of trypsin; the detection of a suite of a, b and y ions in peptides returned from the database, and a mass increment for all cysteine residues to account for modification with methyl methanethiosulphonate and the addition of iTRAQ labels to free amines (N-terminus & lysine). The data was searched through IPI Human v3.23.

2.1.5—Discrimination of Lung Cancer Associated Proteins

The process described in Example 1 section 1.1.6 was employed to discriminate the lung cancer associated proteins in the experimental samples.

2.2 Results

These experiments identified OGTA025, in its two different isoforms, as further described herein. The full-length OGTA025 was detected in the plasma membrane of lung cancer samples. The iTRAQ analysis showed that levels of OGTA025 in the lung cancer samples were higher than in the matched normal adjacent tissue samples.

FIG. 2 shows the Protein Index for OGTA025. See Example 1 section 1.2 for a description of the Protein Index for OGTA025.

Example 3: Screening for mRNA Expression Using Quantitative Reverse Transcriptase Polymerase Chain Reaction (RT-PCR)

Using the following Reference Protocol, various normal and cancerous tissues were screened for OGTA025 mRNA expression using quantitative reverse transcriptase polymerase chain reaction (RT-PCR).

3.1 Materials and Methods

For quantitative RT-PCR, the following OGTA025 primers were used: IGSF4.3: CTCTTTGCTGCTGCCCATGTTTCA (SEQ ID No: 10); IGSF4.4: AAACCTTTCTGGACAGCGTAGGGT (SEQ ID No: 11) as provided by Operon Biotechnologies (Huntsville, Ala.). Standard reaction conditions were used (5 μl cDNA template at 1 ng/μl, 0.1 μl upstream primer at 40 μl M, 0.1 μl downstream primer at 40 μl M, 6 μl 2×SYBR Green PCR mix (Applied Biosystems #4367659), and 0.8 μl water). The cDNA was amplified for 40 cycles using standard PCR conditions in an ABI Prism 7900HT (Applied Biosystems; Foster City, Calif.).

3.2 Results

Figure 3:
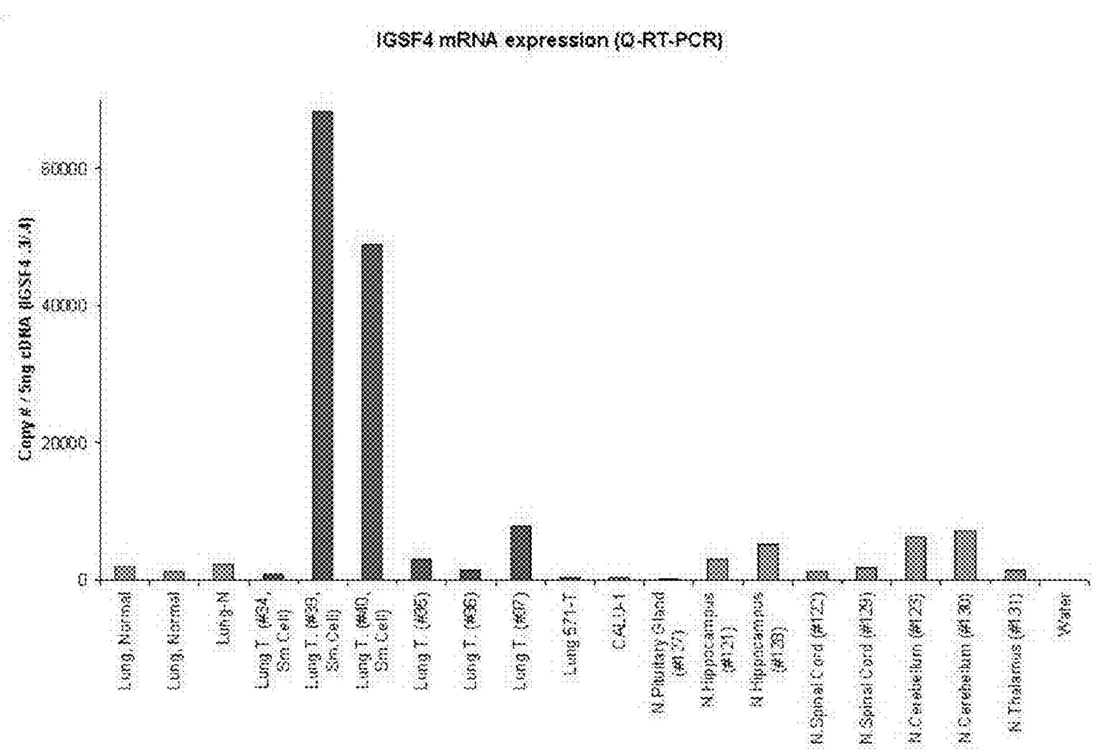
FIG. 3 shows the quantitative reverse transcriptase polymerase chain reaction (RT-PCR) data for the protein of the invention.

FIG. 3 shows the RT-PCR results for OGTA025 for a variety of normal and cancerous tissues. The vertical axis shows the copy #/5 ng cDNA of OGTA025. This graph indicates high mRNA expression of OGTA025 in lung cancer, particularly small cell lung cancer. Expression of mRNA is indicative of OGTA025 protein expression.

Example 4: Generation of Antibodies to OGTA025

Using the following Reference Protocol, the ECD portion of OGTA025 was generated as a recombinant protein and used for immunisation and generation of antibodies to OGTA025.

4.1 Materials and Methods

The ECD portion of OGTA025 was generated as a recombinant protein fused to a 6 His tag in CHO-S cells.

The Sp2/0 myeloma cell line (ATCC CRL 1581) was used for the fusions. The original ATCC vial was thawed and expanded in culture. A seed stock of frozen vials was prepared from this expansion. Cells were maintained in culture for 1 month, passed twice a week. Supernatant from P388D1 (ATCC, TIB-63 FL) cells was used as conditioned media for the hybridomas. Briefly, cells were grown and expanded to 200 mL. Stationary cultures were grown for ~7 days. The exhausted supernatant was spun down and filtered through a 0.2 μm sterile filter. This cell line was passed for 1 month and then a new vial thawed and cultured.

The antibodies generated were from fusions of Sp2/0 cells with lymphocytes extracted from the spleen/lymph nodes of mice (Hco27, Hco7(JK) and KM) immunised with rh OGTA025-ECD-his protein at 5-25 μg dose in Ribi adjuvant by footpad (3-5 day intervals) or ip/sc at 2-4 week intervals for a total of 5-8 immunisations. The OGTA025 sequence used for immunization is shown in FIG. 4 (SEQ ID No: 3). This sequence includes the synthetic signal sequence for secretion.

4.2 Results

A number of OGTA025 antibodies were generated from the above protocol including 1C7, 2G7 and 6G11.

Example 5: Screening Antigen Specific Human Antibodies Using Enzyme-Linked Immunosorbent Assay (ELISA)

Using the following Reference Protocol, the specificity of the antibodies generated in Example 4 was determined by Enzyme-Linked Immunosorbent Assay (ELISA).

5.1 Materials and Methods

The plate was coated overnight with rhOGTA025-ECD-his (or an irrelevant rh Protein-his) 1-2 μg/mL in 1×PBS, 50 μL/well. It was stored in the refrigerator. The plate was emptied and blocked in 1×PBST+5% chicken serum for 30 min-1 hour at room temperature (200 μL/well). The plate was emptied and washed manually with a wash bottle (3×) or plate washer (3×) using 1×PBST. If a wash bottle was used, plates were drained on paper towels.

50 μL/well of blocking buffer was added into the plate and then 50 μL/well of hybridoma supernatant was added. It was incubated at room temperature for 1 hour. A positive control was used when available. The plate was emptied and washed manually with a wash bottle (3×) or plate washer (3×) using 1×PBST. If a wash bottle was used, plates were drained on paper towels.

The secondary, HRP anti-human-IgG Fc (1:3000) or HRP anti-human κ (1:2000) was diluted in 1×PBST+5% chicken serum. 100 μL/well was added and it was incubated for 1 hour at room temperature. The plate was emptied and washed manually with a wash bottle (3×) or plate washer (3×) using 1×PBST. If a wash bottle was used, plates were drained on paper towels.

The plate was developed using 10 mL ABTS substrate. It was incubated for 15-30 minutes at room temperature. The plate was read with Molecular Devices software (415-490 nM).

Reagents and Equipment:

Phosphate buffered saline (PBS), DPBS without Ca and Mg (Hyclone SH30013.03 or Sigma P 3813).

PBS-T (wash buffer), PBS containing 0.05% Tween 20 (Sigma P-1379).

PBS-T plus 1% BSA (Sigma A 9647) or 5% chicken serum. This serves as the blocking buffer and sample buffer.

ELISA plates (Nunc, Imuno-plate F96 Maxisorp 442404 or Falcon, 353912 flex plates or Costar EIA/RIA Plates, 96-well flat bottom, #9018).

rhOGTA025-ECD-his and an irrelevant rh protein-his

HRP anti-human g-chain specific antibody (Jackson, 109-036-098), HRP anti-human k (Bethyl, A80-115P).

ABTS substrate (Moss Inc, product: ABTS-1000).

ELISA plate reader with 405 nm filter.

Automated ELISA plate washer.

5.2 Results

Results showed that the antibodies generated in Example 4 are highly specific to OGTA025.

Example 6: Screening of Human Antibodies Using Fluorescence-Activated Cell Sorting (FACs)

Using the following Reference Protocol, the OGTA025 antibodies generated in Example 4 were screened on NCI-H69 lung cancer cells using fluorescence-activated cell sorting (FACS).

6.1 Materials and Methods

The cells were prepared by counting the NCI-H69 cells and calculating the viability for the cell line. Enough cells for a $0.25\times10^5$/sample were transferred to a 50 ml tube and washed twice with PBS.

The cells were re-suspended in cold FACS buffer (2% FBS in PBS with 0.02% azide) at $2.5\times10^5$ cells/ml. 1004/well was added to a U-bottom 96-well plate (Falcon Non-Tissue Culture Treated #35-1177) and centrifuged at 2500 RPM for 1 minute. The buffer was discarded in one quick motion and the plate was gently patted on paper towels to remove excess buffer.

100 μL of supernatant samples and controls were added to the wells and the pellets were resuspended. It was incubated for 30-40 min on ice. It was then washed once with 200 μL/well of the FACS buffer and centrifuged at 2500 RPM at 4° C. for 1 minute. The buffer was discarded.

50 μL/well of secondary FITC-labeled goat anti human IgG Fc specific (Jackson, #109-095-098) was added at 1:100 dilution. It was incubated for 20-30 min at 4° C. in the dark and then washed twice with 200 μL/well of the FACS buffer and centrifuged at 2500 RPM at 4° C. for 1 minute.

The samples were resuspended in 80 μL/well FACS buffer containing propidium iodide (Roche, Cat. 1 348 639) diluted 1:100. The 96-well plate was directly read on FACS Caliber. The data were analysed using CellQuest software.

FACS Reagents:

FACS buffer: Phosphate buffered saline (PBS) plus 2% FBS (Hyclone, # SH30071.03) and 0.02% of NaN3 (Sigma # S-8032). This served as the blocking buffer as well as the wash buffer.

ELISA plates (Becton Dickinson, Falcon, U-bottom 96 well-plate, #351177).

FACS tubes (Becton Dickinson, Falcon, #352052).

FITC labeled Anti-human γ-chain specific antibody (Jackson, #109-095-098).

Propidium Iodide (Roche #1348639)

FACScalibur (Becton Dickinson)

Eppendorf centrifuge (Eppendorf #581012)

6.2 Results

Figure 5:
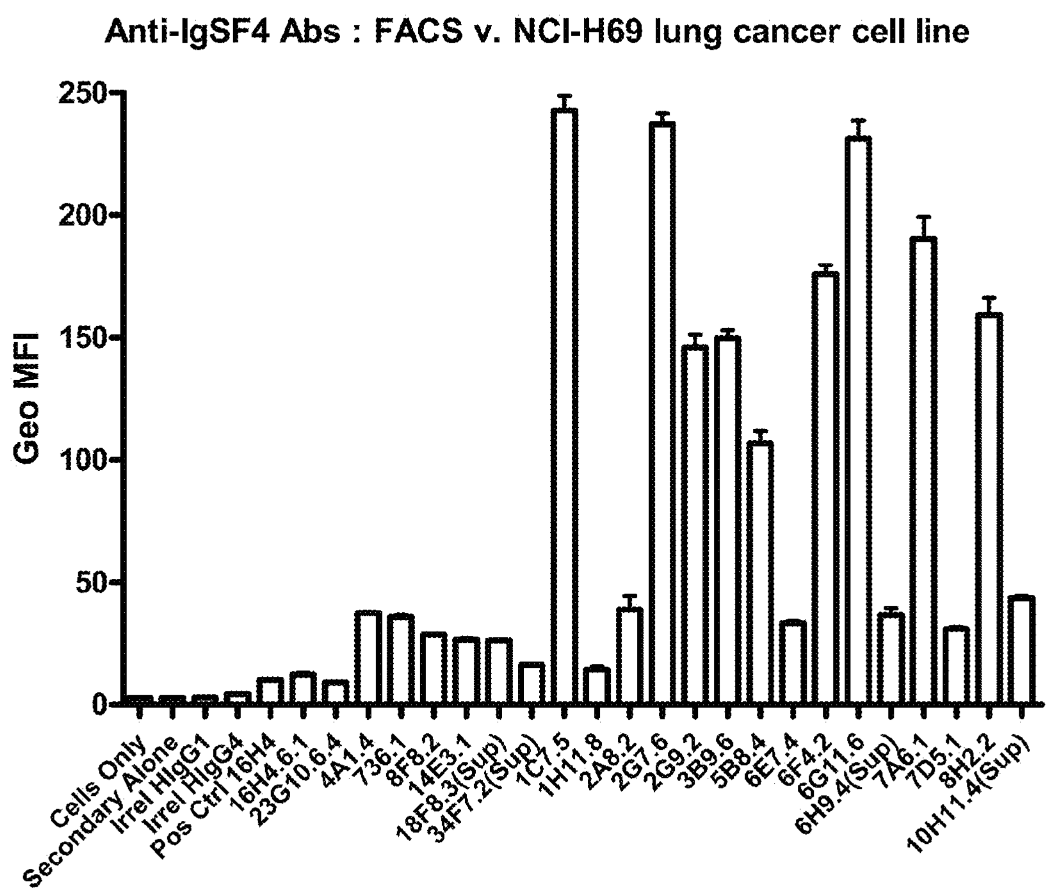
FIG. 5 shows the fluorescence-activated cell sorting (FACS) data for antibodies to the protein of the invention on the NCI-H69 lung cancer cell line.

FIG. 5 shows a graph of the FACS analysis with the samples and controls on the horizontal axis and the geometric mean fluorescence intensity on the vertical axis. This graph shows that there are very good antibodies to OGTA025 which bind well to the NCI-H69 lung cancer cells. Examples of such antibodies are 1C7, 2G7 and 6G11.

Example 7: Immunohistochemistry Using OGTA025 Antibodies

Using the following Reference Protocol, immunohistochemistry was performed on frozen FDA normal tissues and tumour tissues using the OGTA025 antibodies generated in Example 4.

7.1 Materials and Methods 7.1.1—Fixing Slides

The slides were taken from the −80° C. freezer and placed on a tray (with paper towel) in a laminar flow hood to thaw for 30 minutes. The thawed slides were placed in Acetone (Sigma Cat#154598-1L) for 5 minutes. The slides were then placed in 1×PBS for 1 minute.

7.1.2—Preparing Primary Antibody Complex

The primary OGTA025 antibodies (2G7 and 6G11) were diluted using Serum-Free Protein Block (Dako X0909). The final concentration was 100 μg/mL. The Goat anti-Human IgG Fab FITC (Jackson #109-097-003) was diluted; the final concentration was 200 μg/mL (40 μl in 200 μl of Serum-Free Protein Block). Calculated quantities of primary and Human IgG were mixed and incubated for 1-2 minutes and then the diluent (Serum-Free Protein Block) was added. It was then incubated for a further 30 minutes.

7.1.3—Peroxidase Blocking of Slides

A couple of drops of peroxidase blocker (Dako S2001) were placed to cover each section of the slides. The slides were incubated at room temperature for 5 minutes.

7.1.3—Blocking

The slides were rinsed with PBS-Tween20 solution from a squirt bottle. The slides were then dipped in PBS. Each section was covered with Serum-Free Protein Block and incubated for 30 minutes.

The Post Complex Blocking volume of 1% gamma globulin (Jackson #009-000-003) was added to the antibody complex and incubated for 30 minutes.

7.1.4 Antibody Binding

The blocking agent was removed and the primary antibody complex was added to cover each section (~100 μL). The cover slip was placed on the section and it was incubated for 45 minutes. The slides were rinsed with PBS-Tween20 solution from a squirt bottle and washed in 3 PBS baths×4 minutes.

The secondary antibody (1:100 Mouse-anti-FITC or Rabbit-anti-FITC, depending on tissue) was added. The cover slip was placed on the section and it was incubated for 20 minutes. The slides were rinsed with PBS-Tween20 solution from a squirt bottle and washed in 3 PBS baths×4 minutes.

The Polymer-Labeled HRP (Dako K4063/K4002 either mouse/rabbit or just rabbit, depending on the tissue) was added. The cover slip was placed on the section and it was incubated for 20 minutes. The slides were rinsed with PBS-Tween20 solution from a squirt bottle and washed in 2 PBS baths×4 minutes.

The AEC substrate chromogen (Dako K3464) was added and it was incubated for up to 10 minutes while watching for colour change. It was rinsed with dH2O into 10% bleach solution. A couple of drops of hematoxylin were added to the cover section and it was incubated for 2 minutes. It was then rinsed with $H_2O$, dried and mounted.

7.2 Results

OGTA025 antigen was screened across 30 normal tissues in triplicate (3 separate donors per tissue)—these tissues are listed below in Table 3.

TABLE 3

| FDA normal tissue array |
|---|
| Adrenal |
| Brain, Cerebellum |
| Brain, Cerebrum |
| Brain, pituitary |
| Breast |
| Colon |
| Esophagus |
| Heart |

TABLE 3-continued

| FDA normal tissue array |
|---|
| Kidney |
| Liver |
| Lung |
| Skeletal Muscle |
| Pericardial mesothelium |
| Peripheral nerves |
| Ovary |
| Pancreas |
| Placenta |
| Prostate |
| Salivary gland |
| Skin |
| Small intestine |
| Spleen |
| Stomach |
| Testis |
| Thymus |
| Thyroid |
| Tonsil |
| Uterus |
| Uterus, Cervix |
| Bone Marrow |

Immunohistochemistry using OGTA025 antibodies 2G7 and 6G11 on these normal tissues showed no staining in brain or peripheral nerves, minimal staining in pancreas and adrenal (<50% of cells) and strong staining in salivary gland and testis. This confirms that expression of OGTA025 is highly restricted in normal tissues of the human adult.

Immunohistochemistry using OGTA025 antibodies 2G7 and 6G11 on a variety of tumour tissues demonstrated strong staining of tumour cells in brain cancer samples and strong staining in a vast majority of tumour cells in 5/7 small cell lung cancer samples. This is consistent with the hypothesis that antibodies targeting OGTA025 can be used to target cancer cells of brain cancer and lung cancer in a therapeutic setting.

All references referred to in this application, including patent and patent applications, are incorporated herein by reference to the fullest extent possible.

Throughout the specification and the claims which follow, unless the context requires otherwise, the word ‘comprise’, and variations such as ‘comprises’ and ‘comprising’, will be understood to imply the inclusion of a stated integer, step, group of integers or group of steps but not to the exclusion of any other integer, step, group of integers or group of steps.

The invention claimed is:

1. A method of treating small cell lung cancer expressing at the cell surface an OGTA025 polypeptide comprising the amino acid sequence of SEQ ID NO: 1 or SEQ ID NO: 2 in a subject, said method comprising administering to a subject having said small cell lung cancer an effective amount of a conjugated affinity reagent comprising an antibody or antigen binding fragment thereof that specifically binds to said polypeptide, which is conjugated to a therapeutic moiety that is toxic to said cancer.

2. The method according to claim 1, wherein the antibody is a monoclonal antibody or a fragment of the monoclonal antibody.

3. The method according to claim 1, wherein the therapeutic moiety is a cytotoxic agent.

4. The method according to claim 3, wherein the cytotoxic agent is abrin, ricin A, *pseudomonas* exotoxin, or diphtheria toxin.

* * * * *

SEQUENCE LISTING

```
<160> NUMBER OF SEQ ID NOS: 11

<210> SEQ ID NO 1
<211> LENGTH: 443
<212> TYPE: PRT
<213> ORGANISM: Homo Sapiens
<220> FEATURE:
<221> NAME/KEY: MISC_FEATURE
<222> LOCATION: (1)..(443)
<223> OTHER INFORMATION: Swisprot: Q8N2F4; Q9BY67; Ensembl:
      ENSG00000182985 IGSF4 (isoform 1)

<400> SEQUENCE: 1

Met Ala Ser Val Val Leu Pro Ser Gly Ser Gln Cys Ala Ala Ala Ala
1               5                   10                  15

Ala Ala Ala Ala Pro Pro Gly Leu Arg Leu Arg Leu Leu Leu Leu Leu
            20                  25                  30

Phe Ser Ala Ala Ala Leu Ile Pro Thr Gly Asp Gly Gln Asn Leu Phe
        35                  40                  45

Thr Lys Asp Val Thr Val Ile Glu Gly Glu Val Ala Thr Ile Ser Cys
    50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                85                  90                  95

Phe Gln Leu Leu Asn Phe Ser Ser Ser Glu Leu Lys Val Ser Leu Thr
            100                 105                 110

Asn Val Ser Ile Ser Asp Glu Gly Arg Tyr Phe Cys Gln Leu Tyr Thr
        115                 120                 125

Asp Pro Pro Gln Glu Ser Tyr Thr Thr Ile Thr Val Leu Val Pro Pro
    130                 135                 140

Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
```

```
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Thr Thr Ala Thr
                325                 330                 335

Thr Glu Pro Ala Val His Gly Leu Thr Gln Leu Pro Asn Ser Ala Glu
            340                 345                 350

Glu Leu Asp Ser Glu Asp Leu Ser Asp Ser Arg Ala Gly Glu Glu Gly
        355                 360                 365

Ser Ile Arg Ala Val Asp His Ala Val Ile Gly Gly Val Val Ala Val
    370                 375                 380

Val Val Phe Ala Met Leu Cys Leu Leu Ile Ile Leu Gly Arg Tyr Phe
385                 390                 395                 400

Ala Arg His Lys Gly Thr Tyr Phe Thr His Glu Ala Lys Gly Ala Asp
                405                 410                 415

Asp Ala Ala Asp Ala Asp Thr Ala Ile Ile Asn Ala Glu Gly Gly Gln
            420                 425                 430

Asn Asn Ser Glu Glu Lys Lys Glu Tyr Phe Ile
        435                 440


<210> SEQ ID NO 2
<211> LENGTH: 442
<212> TYPE: PRT
<213> ORGANISM: Homo Sapiens
<220> FEATURE:
<221> NAME/KEY: MISC_FEATURE
<222> LOCATION: (1)..(442)
<223> OTHER INFORMATION: SwissProt: Q8N2F4; Q9BY67; Ensembl:
      ENSG00000182985 IGSF4 (isoform 2)

<400> SEQUENCE: 2

Met Ala Ser Val Val Leu Pro Ser Gly Ser Gln Cys Ala Ala Ala Ala
1               5                   10                  15

Ala Ala Ala Ala Pro Pro Gly Leu Arg Leu Arg Leu Leu Leu Leu Leu
            20                  25                  30

Phe Ser Ala Ala Ala Leu Ile Pro Thr Gly Asp Gly Gln Asn Leu Phe
        35                  40                  45

Thr Lys Asp Val Thr Val Ile Glu Gly Glu Val Ala Thr Ile Ser Cys
    50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
```

```
                85                  90                  95

Phe Gln Leu Leu Asn Phe Ser Ser Ser Glu Leu Lys Val Ser Leu Thr
            100                 105                 110

Asn Val Ser Ile Ser Asp Glu Gly Arg Tyr Phe Cys Gln Leu Tyr Thr
        115                 120                 125

Asp Pro Pro Gln Glu Ser Tyr Thr Thr Ile Thr Val Leu Val Pro Pro
    130                 135                 140

Arg Asn Leu Met Ile Asp Ile Gln Arg Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr Thr Thr
            340                 345                 350

Thr Ile Leu Thr Ile Ile Thr Asp Ser Arg Ala Gly Glu Glu Gly Ser
        355                 360                 365

Ile Arg Ala Val Asp His Ala Val Ile Gly Gly Val Val Ala Val Val
    370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415

Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
        435                 440
```

<210> SEQ ID NO 3
<211> LENGTH: 326
<212> TYPE: PRT
<213> ORGANISM: Artificial Sequence
<220> FEATURE:
<223> OTHER INFORMATION: recombinant protein: extracellular domain portion of IGSF4 fused to a 6-His tag

<400> SEQUENCE: 3

```
Met Arg Ala Trp Ile Phe Phe Leu Leu Cys Leu Ala Gly Arg Ala Leu
1               5                   10                  15

Thr Gln Asn Leu Phe Thr Lys Asp Val Thr Val Ile Glu Gly Glu Val
            20                  25                  30

Ala Thr Ile Ser Cys Gln Val Asn Lys Ser Asp Asp Ser Val Ile Gln
        35                  40                  45

Leu Leu Asn Pro Asn Arg Gln Thr Ile Tyr Phe Arg Asp Phe Arg Pro
    50                  55                  60

Leu Lys Asp Ser Arg Phe Gln Leu Leu Asn Phe Ser Ser Ser Glu Leu
65                  70                  75                  80

Lys Val Ser Leu Thr Asn Val Ser Ile Ser Asp Glu Gly Arg Tyr Phe
                85                  90                  95

Cys Gln Leu Tyr Thr Asp Pro Pro Gln Glu Ser Tyr Thr Thr Ile Thr
            100                 105                 110

Val Leu Val Pro Pro Arg Asn Leu Met Ile Asp Ile Gln Arg Asp Thr
        115                 120                 125

Ala Val Glu Gly Glu Glu Ile Glu Val Asn Cys Thr Ala Met Ala Ser
    130                 135                 140

Lys Pro Ala Thr Thr Ile Arg Trp Phe Lys Gly Asn Thr Glu Leu Lys
145                 150                 155                 160

Gly Lys Ser Glu Val Glu Glu Trp Ser Asp Met Tyr Thr Val Thr Ser
                165                 170                 175

Gln Leu Met Leu Lys Val His Lys Glu Asp Asp Gly Val Pro Val Ile
            180                 185                 190

Cys Gln Val Glu His Pro Ala Val Thr Gly Asn Leu Gln Thr Gln Arg
        195                 200                 205

Tyr Leu Glu Val Gln Tyr Lys Pro Gln Val His Ile Gln Met Thr Tyr
    210                 215                 220

Pro Leu Gln Gly Leu Thr Arg Glu Gly Asp Ala Leu Glu Leu Thr Cys
225                 230                 235                 240

Glu Ala Ile Gly Lys Pro Gln Pro Val Met Val Thr Trp Val Arg Val
                245                 250                 255

Asp Asp Glu Met Pro Gln His Ala Val Leu Ser Gly Pro Asn Leu Phe
            260                 265                 270

Ile Asn Asn Leu Asn Lys Thr Asp Asn Gly Thr Tyr Arg Cys Glu Ala
        275                 280                 285

Ser Asn Ile Val Gly Lys Ala His Ser Asp Tyr Met Leu Tyr Val Tyr
    290                 295                 300

Asp Ser Arg Ala Gly Glu Glu Gly Ser Ile Arg Ala Val Asp Ala Ser
305                 310                 315                 320

His His His His His His
                325
```

<210> SEQ ID NO 4
<211> LENGTH: 8
<212> TYPE: PRT
<213> ORGANISM: Homo Sapiens

<400> SEQUENCE: 4

```
Ala Gly Glu Glu Gly Ser Ile Arg
1               5
```

<210> SEQ ID NO 5
<211> LENGTH: 9
<212> TYPE: PRT
<213> ORGANISM: Homo Sapiens

```
<400> SEQUENCE: 5

Cys Glu Ala Ser Asn Ile Val Gly Lys
1               5


<210> SEQ ID NO 6
<211> LENGTH: 6
<212> TYPE: PRT
<213> ORGANISM: Homo Sapiens

<400> SEQUENCE: 6

Asp Phe Arg Pro Leu Lys
1               5


<210> SEQ ID NO 7
<211> LENGTH: 9
<212> TYPE: PRT
<213> ORGANISM: Homo Sapiens

<400> SEQUENCE: 7

Gly Thr Tyr Phe Thr His Glu Ala Lys
1               5


<210> SEQ ID NO 8
<211> LENGTH: 6
<212> TYPE: PRT
<213> ORGANISM: Homo Sapiens

<400> SEQUENCE: 8

Gln Thr Ile Tyr Phe Arg
1               5


<210> SEQ ID NO 9
<211> LENGTH: 13
<212> TYPE: PRT
<213> ORGANISM: Homo Sapiens

<400> SEQUENCE: 9

Ser Asp Asp Ser Val Ile Gln Leu Leu Asn Pro Asn Arg
1               5                   10


<210> SEQ ID NO 10
<211> LENGTH: 24
<212> TYPE: DNA
<213> ORGANISM: Artificial Sequence
<220> FEATURE:
<223> OTHER INFORMATION: upstream primer for RT-PCR

<400> SEQUENCE: 10

ctctttgctg ctgcccatgt ttca                                            24


<210> SEQ ID NO 11
<211> LENGTH: 24
<212> TYPE: DNA
<213> ORGANISM: Artificial Sequence
<220> FEATURE:
<223> OTHER INFORMATION: downstream primer for RT-PCR

<400> SEQUENCE: 11

aaacctttct ggacagcgta gggt                                            24
```